(12) United States Patent
Yamasaki et al.

(10) Patent No.: US 7,691,367 B2
(45) Date of Patent: Apr. 6, 2010

(54) BRANCHED POLYALKYLENE GLYCOLS

(75) Inventors: Motoo Yamasaki, Tokyo (JP);
Toshiyuki Suzuwa, Tokyo (JP); Tatsuya Murakami, Tokyo (JP); Noriko Sakurai, Tokyo (JP); Kinya Yamashita, Shizuoka (JP); Mayumi Mukai, Shizuoka (JP); Takashi Kuwabara, Shizuoka (JP); So Ohta, Tokyo (JP); Ichiro Miki, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 551 days.

(21) Appl. No.: 10/168,956

(22) PCT Filed: Dec. 22, 2000

(86) PCT No.: PCT/JP00/09159

§ 371 (c)(1),
(2), (4) Date: Jun. 24, 2002

(87) PCT Pub. No.: WO01/48052

PCT Pub. Date: Jul. 5, 2001

(65) Prior Publication Data

US 2003/0219404 A1     Nov. 27, 2003

(30) Foreign Application Priority Data

Dec. 24, 1999   (JP)   ................. 11/366312

(51) Int. Cl.
*A81K 38/21* (2006.01)
(52) U.S. Cl. ............... 424/85.4; 435/183; 514/12; 530/399; 548/960
(58) Field of Classification Search ........... 568/852; 424/85.4, 85.3; 435/183; 514/12; 530/399; 548/960
See application file for complete search history.

(56) References Cited

U.S. PATENT DOCUMENTS 4,157,384 A * 6/1979 Watson et al. ............ 424/45
5,183,660 A * 2/1993 Ikeda et al. ............. 424/94.3
5,229,366 A * 7/1993 Tsukada et al. ............ 514/12
5,264,209 A * 11/1993 Mikayama et al. ......... 424/85.2
5,359,030 A * 10/1994 Ekwuribe .................. 530/303
5,643,575 A * 7/1997 Martinez et al. ........ 424/194.1
5,807,971 A * 9/1998 Gozzini et al. ............ 528/332

FOREIGN PATENT DOCUMENTS

| JP | 9-504299 | | 4/1997 |
| WO | WO 94/26778 | * | 11/1994 |
| WO | WO 95/11924 | | 5/1995 |
| WO | WO 96/41813 | | 12/1996 |
| WO | WO 97/10281 | * | 3/1997 |
| WO | WO 98/13025 | * | 4/1998 |
| WO | WO 99/55377 | | 11/1999 |

OTHER PUBLICATIONS

Knauf, et al., "Relationship of Effective Molecular Size to Systemic Clearance in Rats of Recombinant Interleukin-2 Chemically Modified with Water-soluable Polymers", The Journal of Biological Chemistry, vol. 263, No. 29 (1988), 15864-70.
Francis, et al., "PEG-Modified Proteins", Pharmaceutical Biotechnology, vol. 3 (1992), 235-63.
Pettit, et al., "Structure-Function Studies of Interleukin 15 using Site-specific Mutagenesis, Polyethylene Glycol Conjugation, and Homology Modeling", The Journal of Biological Chemistry, vol. 272, No. 4 (1997), 2312-18.

* cited by examiner

*Primary Examiner*—Sikarl A Witherspoon
*Assistant Examiner*—Chukwuma O Nwaonicha
(74) *Attorney, Agent, or Firm*—Fitzpatrick, Cella, Harper & Scinto

(57) ABSTRACT

The present invention provides branched polyalkylene glycols useful as a chemically modifying agent for physiologically active polypeptides, wherein two single-chain polyalkylene glycols are linked to a group having a cyclic structure other than a plane structure, and wherein a group having reactivity with an amino acid side chain, an N-terminal amino group or a C-terminal carboxyl group in a polypeptide or a group convertible into the group having reactivity is linked to the group having a structure other than a plane structure.

17 Claims, 2 Drawing Sheets

```
SEQUENCE LISTING

<160> NUMBER OF SEQ ID NOS: 3

<210> SEQ ID NO 1
<211> LENGTH: 166
<212> TYPE: PRT
<213> ORGANISM: Hominidae

<400> SEQUENCE: 1

Met Ser Tyr Asn Leu Leu Gly Phe Leu Gln Arg Ser Ser Asn Phe
 1               5                   10                  15

Gln Cys Gln Lys Leu Leu Trp Gln Leu Asn Gly Arg Leu Glu Tyr
                 20                  25                  30

Cys Leu Lys Asp Arg Met Asn Phe Asp Ile Pro Glu Glu Ile Lys
                 35                  40                  45

Gln Leu Gln Gln Phe Gln Lys Glu Asp Ala Ala Leu Thr Ile Tyr
                 50                  55                  60

Glu Met Leu Gln Asn Ile Phe Ala Leu Phe Arg Gln Asp Ser Ser
                 65                  70                  75

Ser Thr Gly Trp Asn Glu Thr Ile Val Glu Asn Leu Leu Ala Asn
                 80                  85                  90

Val Tyr His Gln Ile Asn His Leu Lys Thr Val Leu Glu Glu Lys
                 95                  100                 105

Leu Glu Lys Glu Asp Phe Thr Arg Gly Lys Leu Met Ser Ser Leu
                 110                 115                 120

His Leu Lys Arg Tyr Thr Gly Arg Ile Leu His Tyr Leu Lys Ala
                 125                 130                 135

Lys Glu Tyr Ser His Cys Ala Trp Thr Ile Val Arg Val Glu Ile
                 140                 145                 150

Leu Arg Asn Phe Tyr Phe Ile Asn Arg Leu Thr Gly Tyr Leu Arg Asn
                 155                 160                 165 166

<210> SEQ ID NO 2
```

<211> LENGTH: 146
<212> TYPE: PRT
<213> ORGANISM: Hominidae

<400> SEQUENCE: 2

```
Cys Tyr Cys Gln Asp Pro Tyr Val Lys Glu Ala Glu Asn Leu Lys
 1               5                  10                  15

Lys Tyr Phe Asn Ala Gly His Ser Asp Val Ala Asp Asn Gly Thr
            20                  25                  30

Leu Phe Leu Gly Ile Leu Lys Asn Trp Lys Glu Ser Asp Arg
        35                  40                  45

Lys Ile Met Gln Ser Gln Ile Val Ser Phe Tyr Phe Lys Leu Phe
        50                  55                  60

Lys Asn Phe Lys Asp Asp Gln Ser Ile Gln Lys Ser Val Glu Thr
        65                  70                  75

Ile Lys Glu Asp Met Asn Val Lys Phe Phe Asn Ser Asn Lys Lys
        80                  85                  90

Lys Arg Arg Asp Phe Glu Lys Leu Thr Asn Tyr Ser Val Thr Asp
        95                  100                 105

Leu Asn Val Gln Arg Lys Ala Ile His Glu Leu Ile Gln Val Met
        110                 115                 120

Ala Glu Leu Ser Pro Ala Ala Lys Thr Gly Lys Arg Lys Arg Ser
        125                 130                 135

Gln Met Leu Phe Arg Gly Arg Arg Ala Ser Gln
        140                 145 146
```

<210> SEQ ID NO 3
<211> LENGTH: 175
<212> TYPE: PRT
<213> ORGANISM: Hominidae

<400> SEQUENCE: 3

```
Met Thr Pro Leu Gly Pro Ala Ser Ser Leu Pro Gln Ser Phe Leu Leu
 -1  1               5                  10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Leu His
 65                  70                  75

Ser Gly Leu Phe Leu Tyr Gln Gly Leu Leu Gln Ala Leu Glu Gly Ile
 80                  85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
        145                 150                 155

Phe Leu Glu Val Ser Tyr Arg Val Leu Arg His Leu Ala Gln Pro
 160                 165                 170         174
```

BRANCHED POLYALKYLENE GLYCOLS

TECHNICAL FIELD

The present invention relates to polyalkylene glycols having a branched structure, which are useful as modifying agents for a polypeptide having a physiological activity (physiologically active polypeptide), and physiologically active polypeptides modified with the polyalkylene glycol. Furthermore, the present invention relates to pharmaceutical compositions comprising a physiologically active polypeptide modified with the polyalkylene glycol.

BACKGROUND ART

Physiologically active polypeptides are useful as therapeutic agents for specific diseases but when they are administered into the blood, they are unstable and thus a sufficient pharmacological effect cannot be expected in many cases. For example, when a polypeptide having a molecular weight of about 60,000 or less is administered into the blood, it is filtered through glomerulus of the kidney and most of them is secreted into the urine, so that a remarkable therapeutic effect cannot be obtained even if it is used as a therapeutic agent. Thus, a repeated administration is frequently required. Moreover, other polypeptides may be decomposed by a hydrolase or the like existing in the blood to lose the physiological activity. Furthermore, even in the exogenous physiologically active polypeptides, the physiological activity may sometimes be effective for treating diseases. However, since the exogenous physiologically active polypeptides, polypeptides produced by genetic recombination and the like have a structure different from that of an endogenous polypeptide, it is known that the exogenous polypeptides may induce immunoreactions to cause serious side effects such as anaphylactic shock and the like. In addition, some physiologically active polypeptides may frequently be accompanied by the problem of physical properties such as poor solubility and the like when they are used as therapeutic agents.

As one method for solving the problems when physiologically active polypeptides are used as therapeutic agents, a method is known wherein at least one molecule of an inactive polymer chain is chemically linked to the polypeptides. In most cases, a desired property is imparted to the polypeptides or proteins by chemically linking a polyalkylene glycol such as polyethylene glycol or the like to the polypeptides. For example, in superoxide dismutase (SOD) modified with polyethylene glycol, the half-life in the blood is markedly prolonged and thus duration of the activity is found [*Pharm. Research Commun.*, 19: 287 (1987)]. Moreover, the modification of granulocyte colony-stimulating factor (G-CSF) with polyethylene glycol is also known [*J. Biochem.*, 115: 814 (1994)]. Furthermore, examples of polyethylene glycol-modified polypeptides such as asparaginase, glutaminase, adenosinedeaminase, uricase and the like are summarized by Gillian E. Francis et al. [*Pharmaceutical Biotechnology*, vol. 3, *Stability of Protein Pharmaceuticals*, Part B, p. 235 (1992), Plenum Press, New York]. Additionally, as the effect obtained by modifying physiologically active polypeptides with a polyalkylene glycol, increase of thermal stability [*Biophysics* (Seibutsubutsuri), 38: 208 (1998)], solubilization in an organic solvent [*Biochem. Biophys. Res. Commun.* (BBRC), 122: 845 (1984)] and the like are known.

On the other hand, examples of the method of linking a peptide or protein to a polyalkylene glycol include a method wherein an active ester of a carboxylic acid, a maleimido group, carbonate, cyanuric chloride, a formyl group, an oxiranyl group or the like is introduced into the terminal end of the polyalkylene glycol and then the product is linked to an amino group or a thiol group of a polypeptide [*Bioconjugate Chem.*, 6: 150 (1995)]. These techniques include an example wherein the stability in the blood is enhanced by linking polyethylene glycol specifically to a particular amino acid residue in a polypeptide without decreasing the physiological activity of the peptide or protein. As modification with polyethylene glycol which is specific to a particular amino acid residue in a polypeptide, there are an example wherein polyethylene glycol is linked to the carboxy-terminal of a growth hormone-releasing factor through a spacer of norleucine [*J. Peptide Res.*, 49: 527 (1997)], an example wherein cysteine is introduced into the 3-position of interleukin-2 by genetic recombinantion and then polyethylene glycol is specifically linked to the position [*BIO/TECHNOLOGY*, 8: 343 (1990)] and the like.

Most of the above polyalkylene glycol-modified polypeptides are obtained by the method of linking a linear polyalkylene glycol, but it has been found that a method of linking a branched polyalkylene glycol is excellent as a method for obtaining chemically modified polypeptides having a potent activity. It is known that a larger molecular weight of a polyalkylene glycol or a higher modification degree generally results in that duration in the blood is prolonged [*The Journal of Biological Chemistry*, 263: 15064 (1988)], but a high modification degree sometimes causes decrease of the physiological activity of the polypeptide. One reason of the decrease is that a particular amino group, a thiol group or the like necessary for the physiological activity in the polypeptide is modified with a chemically modifying agent. Interleukin-15 is known as an example wherein the physiological activity decreases depending on the modification degree [*J. Biol. Chem.*, 272: 2312 (1997)]. On the other hand, with regard to polyalkylene glycols having a large molecular weight, it is difficult to synthesize those having a homogeneous molecular weight distribution and high purity. For example, in monomethoxy polyethylene glycol, contamination of a diol component as an impurity is known. Thus, it has been attempted to produce a modifying agent having a large molecular weight by branching highly pure polyalkylene glycols having a narrow molecular weight distribution available at present through a spacer. Thus, a chemically modified polypeptide having a potent physiological activity can be obtained with retaining durability even when the modification degree is reduced. Also, it is considered that the surface of a physiologically active polypeptide can be covered more efficiently by branching a polyalkylene glycol. For example, a double-chain polyethylene glycol derivative is known wherein cyanuric chloride is used as a group having a branched structure (Japanese Published Unexamined Patent Application Nos. 72469/91 and 95200/91). In this case, methoxy polyethylene glycol having an average molecular weight of 5,000 is used but there is fear of toxicity derived from a triazine ring in the compound. Moreover, Japanese Published Unexamined Patent Application No. 153088/89 discloses that a chemically modified polypeptide having a more potent activity can be obtained with a lower modification degree by using a comb-shaped polyethylene glycol which is a copolymer of polyethylene glycol and maleic anhydride as compared to a linear polyethylene glycol. However, a number of reaction sites with a polypeptide are present and the molecular weight distribution is not uniform in the compound. In addition, an example wherein polyethylene glycols are branched through a benzene ring using cinnamic acid as a starting material (Japanese Published Unexamined Patent Application No. 88822/91) is also known. In the above branched polyalkylene glycols through a triazine ring or a benzene ring, the structure at the branching point is plane, so that spatial movement of the polyalkylene glycol chain is restricted and thus they are considered to be disadvantageous for the effect of increasing the molecular size. As another example, a compound wherein two polyethylene glycol are branched using lysine as a branching point (WO 96/21469, U.S. Pat. No. 5,643,575) and the like are known, but the compound having branches at a cyclic structure of the present invention is unknown. Furthermore, the above conventional branched polyalkylene glycols achieve the increase of the molecular weight by linking at least two molecules of a polyalkylene glycol, but it is not known that the molecular size can be increased more effectively when physiologically active polypeptides are modified with a branched polyalkylene glycol than the case when they are modified with a linear polyalkylene glycol having the same molecular weight.

The branched polyalkylene glycols as a modifying agent which overcome the problems of the above conventional polyalkylene glycols, have a low toxicity and an improved stability and are excellent in the effect of increasing the molecular size have been desired.

Recently, an interferon-β preparation has been paid attention to as a therapeutic agent for multiple scleroses [*The Lancet*, 352(7): 1491 (1998) and the like]. Multiple scleroses are demyelinating autoimmune diseases of unknown etiology and are characterized in the infiltration of perivascular cell of central nerve white matter and successive destruction of myelin sheath. The mechanism of the outbreak is unknown but it is considered that a nerve conduction disorder occurs as a result of demyelination spots which are caused through the destruction of myelin sheath covering the axon of a central nerve by immunocyte and thereby various disorders of neural functions may be exhibited. In Western countries, interferon-β (IFN-β) becomes a mainstream therapeutic agent for multiple scleroses but the IFN-β1b preparation clinically used at present has problems that subcutaneous injection on alternate days is required and the like, so that a therapeutic agent which has an increased activity and is effective even at less number of dose frequency has been desired. Moreover, interferons are effective for viral hepatitis such as hepatitis C, hepatitis B and the like, and treatment of various cancers such as leukemia, lymphoma, myeloma, osteosarcoma, breast cancer, kidney cancer, brain tumor and the like, viral or inflammatory skin diseases, and eye diseases in addition to multiple scleroses [*Pharmacy* (Yakkyoku), 41(6): 769 (1990)], and the possibility as a therapeutic agent for diseases relating to vascularization is suggested [*Tissue Culture* (Soshikibaiyo), 22(7): 278 (1996)]. For these diseases, an effective therapeutic agent having a high duration at a low dose and a low dose frequency has been desired as well.

DISCLOSURE OF THE INVENTION

An object of the present invention is firstly to provide branched polyalkylene glycols which overcome the defects of the conventional branched polyalkylene glycols as a modifying agent for physiologically active polypeptides and are excellent in the effect of increasing the molecular size. Secondly, it is to provide physiologically active polypeptides modified with the branched polyalkylene glycol.

The present inventors have extensively studied branched polyalkylene glycol type modifying agents having a novel structure for modifying physiologically active polypeptides. As a result, it has been found that a modifying agent excellent in the effect of increasing the molecular size and in the stability can be obtained by branching polyalkylene glycols using a compound having a three-dimensional or motile cyclic structure such as a cycloalkane or the like. Moreover, it has also been found that the modification of physiologically active polypeptides with the above branched polyalkylene glycol increases the activity. Furthermore, it has been found that, when the physiologically active polypeptides are modified with the above branched polyalkylene glycol, the duration in the blood is remarkably prolonged through the suppression of filtration in glomeruli of the kidney while maintaining the physiological activity in the modified physiologically active polypeptides.

As described above, it has been found that the above branched polyalkylene glycols are excellent as a chemically modifying agent, and thus the present invention has been accomplished.

Namely, the present invention provides a branched polyalkylene glycol wherein two single-chain polyalkylene glycols which are linked to a group having a cyclic structure other than a plane structure, and wherein a group having reactivity with an amino acid side chain, an N-terminal amino group or a C-terminal carboxyl group in a polypeptide or a group convertible into the group having reactivity is linked to the group having a structure other than a plane structure; a physiologically active polypeptide or a derivative thereof modified with the polyalkylene glycol; and a pharmaceutical composition or a therapeutic agent comprising the physiologically active polypeptide or the derivatives thereof modified with the polyalkylene glycol. Among these, it is preferable that the group having a cyclic structure other than a plane structure is a group formed by removing 3 to 5 hydrogen atoms from a compound represented by formula (II):

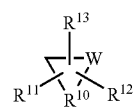

(II)

wherein $R^{10}$ represents $(CH_2)_u$ in which u represents an integer of 1 to 10, or $CH=CH-(CH_2)_{ua}$ in which ua represents an integer of 0 to 8, $R^{11}$, $R^{12}$ and $R^{13}$ are the same or different and each represents a hydrogen atom, a hydroxyl group, substituted or unsubstituted lower alkyl, lower alkoxy, amino, carboxy, cyano or formyl, W represents O, S, $CH_2$ or $NR^{14}$ in which $R^{14}$ represents a hydrogen atom or lower alkyl.

In the above, it is more preferable that W is $CH_2$ and u is 4 in formula (II). Moreover, in another aspect, the present invention relates to a chemically modified polypeptide wherein a physiologically active polypeptide or derivative thereof is modified with at least one of the above branched polyalkylene glycols directly or through a spacer, and a pharmaceutical composition or a therapeutic agent comprising the chemically modified polypeptide.

The present invention will be explained below in detail.

The group having a cyclic structure other than a plane structure includes any of groups containing a cyclic structure other than a plane structure, but a group having a cyclic structure other than a plane structure and being capable of having 3 or more branches is preferable, and a group having a cyclic structure other than a plane structure and being capable of having 3 to 5 branches is more preferable.

The single-chain polyalkylene glycols linked to the group having a cyclic structure other than a plane structure include any of single-chain polyalkylene glycols capable of linking to the group having a cyclic structure other than a plane structure, but $R^1$-$M_n$-$X^1$ wherein M, n, $R^1$, and $X^1$ have the same meanings as described below is preferred.

The group having reactivity with an amino acid side chain, an N-terminal amino group or a C-terminal carboxyl group in a polypeptide or the group convertible into the group having reactivity includes any of groups having reactivity with an amino acid side chain, an N-terminal amino group or a C-terminal carboxyl group in a polypeptide or groups convertible into the group having reactivity.

The preferable branched polyalkylene glycol of the present invention is a compound (hereinafter referred to as "Compound (I)"; the same shall apply to the compounds having other formula number) represented by formula (I):

$$(R^1\text{-}M_n\text{-}X^1)_2 L(X^2\text{—}X^3\text{—}R^2)_q \qquad (I)$$

wherein L represents a group having a cyclic structure other than a plane structure and being capable of having 3 to 5 branches, M represents $OCH_2CH_2$, $OCH_2CH_2CH_2$, $OCH(CH_3)CH_2$, $(OCH_2CH_2)_r$—$(OCH_2CH_2CH_2)_s$ in which r and s are the same or different and each represents any positive integer, or $(OCH_2CH_2)_{ra}$—$(OCH(CH_3)CH_2)_{sa}$ in which ra and sa have the same meanings as the above r and s, respectively, n represents any positive integer, q represents an integer of 1 to 3, $R^1$ represents a hydrogen atom, lower alkyl or lower alkanoyl, $R^2$ represents a group having reactivity with an amino acid side chain, an N-terminal amino group or a C-terminal carboxyl group in a polypeptide or a group convertible into the group having reactivity, $X^1$ represents a bond; O; S; alkylene; $O(CH_2)_{ta}$ in which ta represents an integer of 1 to 8; $(CH_2)_{tb}O$ in which tb has the same meaning as the above ta; $NR^3$ in which $R^3$ represents a hydrogen atom or lower alkyl; $R^4$—NH—C(=O)—$R^5$ wherein $R^4$ represents a bond, alkylene or $O(CH_2)_{tc}$ in which tc has the same meaning as the above ta, and $R^5$ represents a bond, alkylene or $OR^{5a}$ in which $R^{5a}$ represents a bond or alkylene; $R^6$—C(=O)—NH—$R^7$ wherein $R^6$ represents a bond, alkylene or $R^{6a}O$ in which $R^{6a}$ has the same meaning as the above $R^{5a}$, and $R^7$ represents a bond, alkylene or $(CH_2)_{td}O$ in which td has the same meaning as the above ta; $R^8$—C(=O)—O in which $R^8$ has the same meaning as the above $R^{5a}$; or O—C(=O)—$R^9$ in which $R^9$ has the same meaning as the above $R^{5a}$, $X^2$ represents a bond, O or $(CH_2)_{te}O$ in which te has the same meaning as the above ta, $X^3$ represents a bond or alkylene, and 2 $R^1$-$M_n$-$X^1$'s and 1 to 3 $X^2$—$X^3$—$R^2$'s are independently the same or different.

In the definition of each group in formula (I), the lower alkyl and the lower alkyl moiety of the lower alkanoyl include linear or branched lower aklyls having 1 to 8 carbon atoms, such as methyl, ethyl, n-propyl, isopropyl, n-butyl, isobutyl, sec-butyl, tert-butyl, pentyl, neopentyl, hexyl, heptyl, octyl and the like. The alkylene includes alkylenes having 1 to 8 carbon atoms, such as methylene, ethylene, n-propylene, isopropylene, n-butylene, isobutylene, sec-butylene, tert-butylene, pentylene, neopentylene, hexylene, heptylene, octylene and the like.

In formula (I), M represents $OCH_2CH_2$, $OCH_2CH_2CH_2$, $OCH(CH_3)CH_2$, $(OCH_2CH_2)_r$—$(OCH_2CH_2CH_2)_s$ wherein r and s are the same or different and each represents any positive integer, or $(OCH_2CH_2)_{ra}$—$(OCH(CH_3)CH_2)_{sa}$ wherein ra and sa have the same meanings as the above r and s, respectively. When M is $(OCH_2CH_2)_r$—$(OCH_2CH_2CH_2)_s$ wherein r and s have the same meanings as described above, or $(OCH_2CH_2)_{ra}$—$(OCH(CH_3)CH_2)_{sa}$ wherein ra and sa have the same meanings as described above, r and s, and ra and sa are preferably from 1 to 100,000 and more preferably from 1 to 1,000.

In formula (I), n represents any positive integer, is preferably from 10 to 100,000, and more preferably from 100 to 1,000.

The average molecular weight of the polyalkylene glycol moiety represented by $M_n$ is preferably from about 1,000 to 1,000,000 and more preferably from 5,000 to 100,000. When $M_n$ is —$(OCH_2CH_2)_n$—, it is preferable the starting material, i.e., polyethylene glycol has a monodispersed molecular weight distribution of 1.1 or less, in which the molecular weight distribution is represented by Mw (weight-average molecular weight)/Mn (number-average molecular weight), and commercially available one can be used when the average molecular weight is 30,000 or less. For example, monomethoxy polyethylene glycol having an average molecular weight of 2,000, 5,000, 10,000, 12,000, 20,000 or the like can be used.

The molecular weight of the branched polyalkylene glycol wherein two single-chain polyalkylene glycols are linked to a group having a cyclic structure other than a plane structure and a group having reactivity with an amino acid side chain, an N-terminal amino group or an C-terminal carboxyl group in a polypeptide or a group convertible into the group having reactivity is further linked to the group having a structure other than a plane structure or the molecular weight of the branched polyalkylene glycol represented by formula (1) is preferably from 500 to 1,000,000.

In formula (I), q represents an integer of 1 to 3, and is preferably 1.

In formula (I), L represents a group having a cyclic structure other than a plane structure and being capable of having 3 to 5 branches, which may have a hydroxyl group, substituted or unsubstituted lower alkyl, lower alkoxy, amino, carboxy, cyano, formyl or the like as a substituent on the cyclic structure. The lower alkyl and the lower alkyl moiety of the lower alkoxy has the same meaning as the above lower alkyl, and the substituent in the substituted lower alkyl includes a hydroxyl group, amino, lower alkanoyloxy, lower alkanoylamino, lower alkoxy, lower alkoxyalkoxy, lower alkanoyl, lower alkoxycarbonyl, lower alkylcarbamoyl, lower alkylcarbamoyloxy and the like. The alkyl moiety of the lower alkanoyloxy, the lower alkanoylamino, the lower alkoxy, the lower alkoxyalkoxy, the lower alkanoyl, the lower alkoxycarbonyl, the lower alkylcarbamoyl and the lower alkylcarbamoyloxy has the same meaning as the above lower alkyl. Examples of L include groups formed by removing 3 to 5 hydrogen atoms from cyclohexanes, cyclohexenes, monosaccharides or the like. Specific examples of the cyclohexanes, the cyclohexenes or the monosaccharides include cyclohexanetricarboxylic acid, cyclohexanetriol, 1,3,5-trimethyl-1,3,5-cyclohexanetricarboxylic acid (Kemp's triacid), quinic acid, diaminocyclohexane, 2,4,10-trioxaadamantane, inositol, shikimic acid, D,L-sorbitol, ribose, erythritol and the like and stereoisomers thereof. L is preferably a group formed by removing 3 to 5 hydrogen atoms from a compound represented by formula (II):

wherein $R^{10}$ has the same meaning as described above, $R^{11}$, $R^{12}$ and $R^{13}$ have the same meanings as described above, respectively, and W has the same meaning as described above.

In formula (II), it is preferred that W is $CH_2$ and u is 4.

The lower alkyl and the lower alkyl moiety of the lower alkoxy has the same meaning as the above lower alkyl, and the substituent in the substituted lower alkyl has the same meaning as the substituent of the above substituted alkyl.

The structure of the L moiety can be constructed by using a commercially available compound as it is, using the compound through conversion into a derivative suitable for the linkage to a polyalkylene glycol according to a common organic synthetic method, or using the compound after the protection of a functional group [Edited by The Chemical Society of Japan, *Experimental Chemistry Course*, Fourth edition (1992), Organic synthesis I to V, Maruzen, *PROTECTIVE GROUPS IN ORGANIC SYNTHSIS*, Second edition, JOHN WILEY & SONS, INC. (1991), etc.]

Cyclohexanes other than those listed in the above can be synthesized according to the method of Kihi et al. [*Great Organic Chemistry* (Daiyukikagaku), 6: 183 (1958), Asakura Shoten] or G. E. McCasland and E. Clide Horswill [*Journal of American Chemical Society*, 76: 2373 (1954)], or the like.

Moreover, for example, the structure of the L moiety can also be constructed by converting a compound having a benzene ring into a compound having a cyclic structure other than a plane structure and being capable of having 3 to 5 branches according to the method of S. Isoda and H. Yamaguchi [*Chem. Pharm. Bull.*, 28(8): 2337 (1980)], the method of K. Prasad and O. Repic [*Tetrahedron Letters*, 25(23): 2435 (1984)] or the like.

In Compound (I), the linkage of a polyalkylene glycol to L through $X^1$ can be carried out by easily combining the reactions known in the common organic synthesis [Edited by The Chemical Society of Japan, *Experimental Chemistry Course*, Fourth edition (1992), pp. 19-23, Organic synthesis, I to V, Maruzen].

In formula (I), $R^2$ represents a group having reactivity with an amino acid side chain, an N-terminal amino group or a C-terminal carboxyl group in a polypeptide or a group convertible into the group having reactivity.

Namely, the group having reactivity includes groups reactive with at least of each side chain of lysine, cysteine, arginine, histidine, serine, threonine, tryptophan, aspartic acid, glutamic acid, glutamine and the like; an N-terminal amino group; and a C-terminal carboxyl group, in a polypeptide. Specific examples include a hydroxyl group, carboxy, formyl, amino, vinylsulfonyl, mercapto, cyano, carbamoyl, halogenated carbonyl, halogenated lower alkyl, isocyanato, isothiocyanato, oxiranyl, lower alkanoyloxy, maleimido, succinimidooxycarbonyl, substituted or unsubstituted aryloxycarbonyl, benzotriazolyloxycarbonyl, phthalimidooxycarbonyl, imidazolylcarbonyl, substituted or unsubstituted lower alkoxycarbonyloxy, substituted or unsubstituted aryloxycarbonyloxy, tresyl, lower alkanoyloxycarbonyl, substituted or unsubstituted aroyloxycarbonyl, substituted or unsubstituted aryl disulfido, azido and the like.

In the above definition of each group, the lower alkyl moiety of the lower alkoxycarbonyloxy, the halogenated lower alkyl, the lower alkanoyloxy and the lower alkanoyloxycarbonyl has the same meaning as the above lower alkyl. The aryl moiety of the aryloxycarbonyl, the aryloxycarbonyloxy and the aryl disulfido includes aryls having 6 to 14 carbon atoms, such as phenyl, naphthyl, biphenyl, anthryl and the like. The aroyl moiety of the aroyloxycarbonyl includes aroyls having 7 to 13 carbon atoms, such as benzoyl, naphthoyl, phthaloyl and the like. The halogen moiety of the halogenated carbonyl and the halogenated lower alkyl includes atoms of fluorine, chlorine, bromine and iodine.

The substituent in the substituted lower alkoxycarbonyloxy includes 1 to 3 substituents which are the same or different. Examples include a hydroxyl group, carboxy, halogen and the like. The halogen has the same meaning as described above.

The substituent in the substituted aryloxycarbonyl, the substituted aryloxycarbonyloxy, the substituted aryl disulfido and the substituted aroyloxycarbonyl includes 1 to 3 substituents which are the same or different. Examples include a hydroxyl group, carboxy, halogen, cyano, lower alkyl and the like. The halogen and the lower alkyl have the same meanings as described above, respectively.

The group represented by $R^2$ may be contained in the starting material which constructs the structure of the L moiety or may be formed by protecting a necessary functional group in the starting material with an appropriate protective group in advance [*PROTECTIVE GROUPS IN ORGANIC SYNTHSIS*, Second edition, JOHN WILEY & SONS, INC. (1991), etc.], removing the protective group after branching polyalkylene glycols by linking them to L through $X^1$'s, and converting it, if necessary. Furthermore, after polyalkylene glycols are branched from L through $X^1$'s, the above $R^2$ can be introduced into L through $X^2$ or $X^3$ by a usual organic synthetic method.

More specifically, the branched polyalkylene glycols of the present invention can be produced, for example, by the following production methods. But, the production methods of the branched polyalkylene glycols of the present invention are not limited thereto.

PRODUCTION METHOD 1

Production of the Compound Wherein $X^1$ is a Bond, O, Alkylene, $O(CH_2)_{ta}$ or $(CH_2)_{tb}O$ Among Compounds (I), Compound (Ia) wherein $X^1$ is a bond, O, alkylene, $O(CH_2)_{ta}$ in which ta has the same meaning as described above, or $(CH_2)_{tb}O$ in which tb has the same meaning as described above, can be produced, for example, by the following method.

A cyclic polyol having at least two hydroxyl groups (hereinafter, the cyclic polyol herein includes also the compounds having hydroxy-lower alkyl or the like as well as a hydroxyl group as a substituent on the cyclic structure) is dissolved or suspended into an appropriate solvent such as N,N-dimethylformamide, dimethyl sulfoxide, toluene, tetrahydrofuran, acetonitrile, pyridine or the like in anhydrous conditions, 1 to 3 molar equivalents of a halide or tosylate of a polyalkylene glycol or a monoalkyl ether or monocarboxylate ester thereof (hereinafter, they are collectively referred to as "Polyalkylene Glycol A") is added thereto in the presence of 1 to 30 mol of an appropriate base such as sodium hydride, zinc oxide, sodium hydroxide, triethylamine or the like, and allowed to react at −20 to 150° C. for 1 hour to 10 days to obtain a mixture containing a double-chain branched polyalkylene glycol.

The cyclic polyol is selected from commercially available compounds such as cyclohexanetriol, quinic acid, shikimic acid, glucose, sorbitol, ribose, erythritol and the like, and compounds derived from the commercially available compounds. Examples of the compounds derived from the commercially available compounds include cyclic polyols obtained by reducing cyclic polycarboxylic acid selected from cyclohexanetricarboxylic acid, Kemp's triacid and the like with an appropriate reducing agent according to a usual organic synthetic method [Edited by The Chemical Society of Japan, *Experimental Chemistry Course*, Fourth edition (1992), vols. 19-21, Maruzen]. The reducing agent includes lithium aluminum hydride, sodium borohydride, sodium cyanoborohydride, hydrogen and the like.

The hydroxyl groups in the cyclic polyol may be arranged at any position, and the compound can be used in the reaction after a functional group unnecessary for the reaction is suitably protected or converted into a derivative by the method described in *PROTECTIVE GROUPS IN ORGANIC SYNTHSIS*, Second edition, JOHN WILEY & SONS, INC. (1991) or the like.

The halide or tosylate of Polyalkylene Glycol A can easily be produced by various methods disclosed in a summary of Samuel Zalipsky [*Bioconjugate Chem.*, 6: 150 (1995)] and the like. As the halide or tosylate of Polyalkylene Glycol A for the linking, the compound having any average molecular weight can be used, so long as the molecular weight distribution is uniform (preferably Mw/Mn is 1.1 or less).

The obtained mixture containing a double-chain branched polyalkylene glycol can be used in the next step at the purity as it is or after purifying and isolating the double-chain branched polyalkylene glycol having any purity according to a known method such as ion-exchange chromatography, reversed phase chromatography, hydrophobic chromatography, two-phase partition, recrystallization or the like. By the above steps, among Compounds (Ia), some of Compounds (Iaj) wherein $R^2$ is a hydroxyl group are obtained.

On the other hand, an objective double-chain branched polyalkylene glycol can also be prepared using a cyclic polyhalide or a cyclic polytosyl and Polyalkylene Glycol A. In this case, an objective product is obtained by dissolving or suspending 1 to 3 molar equivalents of Polyalkylene Glycol A in an appropriate solvent such as N,N-dimethylformamide, dimethyl sulfoxide, toluene, tetrahydrofuran or the like, adding 1 molar equivalent of a cyclic polyhalide or cyclic polytosyl thereto in the presence of 1 to 30 mol of an appropriate base such as sodium hydride, zinc oxide, sodium hydroxide, triethylamine or the like, and reacting them at −20 to 150° C. for 1 hour to 10 days.

The cyclic polyhalide may be a commercially available compound or obtained by converting the above cyclic polyol into a halide compound [Edited by The Chemical Society of Japan, *Experimental Chemistry Course*, Fourth edition (1992), vol. 19, Maruzen]. The cyclic polytosyl can be obtained by dissolving or suspending a cyclic polyol in an appropriate solvent such as N,N-dimethylformamide, dimethyl sulfoxide, toluene, tetrahydrofuran, acetonitrile, pyridine or the like, 1 to 3 molar equivalents of a tosyl halide is added thereto in the presence of 1 to 30 mol of an appropriate base such as sodium hydride, zinc oxide, sodium hydroxide, triethylamine, potassium naphthalene or the like, and reacting them at −20 to 150° C. for 1 hour to several days.

Next, $R^2$ is introduced into a mixture containing a double-chain branched polyalkylene glycol or a purified compound thereof. As $R^2$, a functional group remaining in a cyclic polyol, a cyclic polyhalide or a cyclic polytosyl is used as it is after Polyalkylene Glycol A or a halide or tosylate thereof is linked to the cyclic polyol, the cyclic polyhalide or the cyclic polytosyl, or a group obtained by protecting a functional group linked to a cyclic polyol in advance, linking Polyalkylene Glycol A or a halide or tosylate thereof, and removing the protecting group of the functional group can be used. In this case, after at least one hydroxyl group or other functional group in the cyclic polyol, the cyclic polyhalide or the cyclic polytosyl is protected with an appropriate protective group, Polyalkylene Glycol A or a halide or tosylate thereof is introduced into the remaining hydroxyl group, halogen or tosyl group moiety by the same method as above to synthesize a compound to which two polyalkylene glycols are linked, and then the functional group from which the protective group is removed is used as it is, or at least one of the functional groups is converted to $R^2$ according to the method described below. The functional group present in the cyclic polyol, the cyclic polyhalide or the cyclic polytosyl before or after the linking of Polyalkylene Glycol A or a halide or tosylate thereof includes carboxy, amino, halogen, cyano, formyl, carbonyl and the like, in addition to a hydroxyl group. The appropriate protective group of the functional group for a hydroxyl group includes benzyl, tert-butyl, acetyl, benzyloxycarbonyl, tert-butyloxycarbonyl, dimethyl-tert-butylsilyl, diphenyl-tert-butylsilyl, trimethylsilyl, triphenylsilyl, tosyl, tetrahydropyranyl and the like; the group for amino includes methyl, ethyl, 9-fluorenylmethyloxycarbonyl, benzyloxycarbonyl, nitrobenzyloxycarbonyl, N-phthalimido, acetyl, tert-butyloxycarbonyl and the like; the group for carboxy includes benzyl, methyl, ethyl, tert-butyl, 9-fluorenylmethyl, methoxyethoxymethyl, 2,2,2-trichloroethyl, 2-(trimethylsilyl) ethyl, cinnamoyl, allyl, nitrophenyl and the like; and the group for formyl includes dimethyl acetal, diethyl acetal, dibenzyl acetal, 1,3-dioxanyl and the like [*PROTECTIVE GROUPS IN ORGANIC SYNTHSIS*, Second edition, JOHN WILEY & SONS, INC. (1991)].

The functional group present in advance may be used as $R^2$, as it is or after protection and deprotection. Examples of the cyclic polyol, the cyclic polyhalide or the cyclic polytosyl which may be used as a starting material for constructing the structure of the L moiety include shikimic acid, quinic acid, Kemp's triacid and the like.

Among Compounds (I), a compound obtained by newly introducing substituent $R^2$ into a compound containing L can be easily produced, for example, by the following production method.

Production Method 1-1

Among Compounds (Ia),
a compound wherein $R^2$ is carboxy, i.e., a compound represented by formula (Iaa):

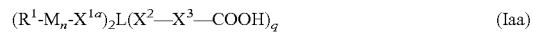

(Iaa)

wherein $X^{1a}$ represents a bond, O, S, alkylene, $O(CH_2)_{ta}$ or $(CH_2)_{tb}O$, and $R^1$, L, M, n, q, $X^2$ and $X^3$ have the same meanings as described above, respectively;

a compound wherein $R^2$ is carbamoyl, i.e., a compound represented by formula (Iab):

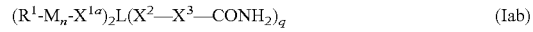

(Iab)

wherein $R^1$, L, M, n, q, $X^{1a}$, $X^2$ and $X^3$ have the same meanings as described above, respectively; and a compound wherein $R^2$ is cyano, i.e., a compound represented by the formula (Iac):

(Iac)

wherein $R^1$, L, M, n, q, $X^{1a}$, $X^2$ and $X^3$ have the same meanings as described above, respectively, can be synthesized, for example, as follows.

Compound (Iaa), Compound (Iab) and Compound (Iac) can be obtained by reacting a reaction mixture containing Compound (Iaj) having a hydroxyl group as $R^2$ or purified compound among Compounds (Ia) obtained in accordance with Production Method 1 using a cyclic polyol with 1 to 30 molar equivalents of acrylic acid, acrylamide, acrylonitrile or the like in an appropriate solvent such as water, methylene chloride, toluene, tetrahydrofuran or the like in the presence of a catalytic amount or 1 to 20% of a base at −20 to 150° C.

for 1 hour to several days. The base includes potassium hydroxide, sodium hydroxide, sodium hydride and the like.

Moreover, Compound (Iaa) can also be obtained by dissolving or suspending a reaction mixture containing Compound (Iaj) or purified compound obtained in Production Method 1 in an appropriate solvent such as N,N-dimethylformamide, dimethyl sulfoxide, toluene, tetrahydrofuran or the like in anhydrous conditions, and reacting the compound with 1 to 50 molar equivalents of α-halogenated acetic acid ester in the presence of 1 to 50 mol of an appropriate base such as sodium hydride, zinc oxide, sodium hydroxide, triethylamine or the like at −20 to 150° C. for 1 hour to several days, followed by hydrolysis.

Furthermore, Compound (Iaa) can also be obtained by dissolving or suspending a reaction mixture containing Compound (Iaj) obtained, for example, in Production Method 1 in an appropriate solvent such as N,N-dimethylformamide, dimethyl sulfoxide, toluene, tetrahydrofuran or the like, and reacting the compound with 1 to 50 mol of an activating agent such as succinimidyl carbonate, p-nitrophenyl chloroformate, carbonyldiimidazole or the like in the presence of 1 to 50 mol of an appropriate base such as sodium hydride, zinc oxide, sodium hydroxide, triethylamine or the like at −20 to 100° C. for 1 hour to 10 days to activate the compound, followed by reacting it with an amino acid such as γ-aminobutyric acid, glycine, β-alanine or the like or derivatives thereof.

Also, Compound (Iaa) can be produced by reacting Compound (Iaj) obtained in Production Method 1 with an acid anhydride such as succinic anhydride or glutamic anhydride in the presence of the same base as above.

Moreover, after producing Compound (Iai) wherein $R^2$ is halogenated lower alkyl among Compounds (Ia) in accordance with Production Method 1, using, for example, a cyclic polyhalide, Compound (Iaa) can also be obtained by dissolving or suspending hydroxycarboxylate, malonate, γ-aminobutyrate, an ester of β-alanine, an ester of glycine or the like in an appropriate solvent such as N,N-dimethylformamide, dimethyl sulfoxide, toluene, tetrahydrofuran or the like, adding Compound (Iai) thereto in the presence of 1 to 50 mol of an appropriate base such as sodium hydride, zinc oxide, sodium hydroxide, triethylamine or the like, and reacting them at −20 to 150° C. for 1 hour to several days, followed by hydrolysis.

Furthermore, Compound (Iaa) can also be obtained by replacing at least one hydroxyl group or halogen of the cyclic polyol or the cyclic polyhalide with a residue containing carboxylic acid or a protected form of carboxylic acid in advance, and then, using the compound, replacing remaining two hydroxyl groups or halogens of the cyclic polyol or cyclic polyhalide with Polyalkylene Glycol A or a halide or tosylate thereof according to the method shown in Production Method 1. In this case, the introduction of the residue containing carboxylic acid or a protected form of carboxylic acid can be carried out in a similar manner to the above. When carboxylic acid is protected, free carboxylic acid is formed by deprotection after the introduction of Polyalkylene Glycol A or a halide or tosylate thereof into the cyclic polyol or cyclic polyhalide.

The compound converted into carboxylic acid can be purified or isolated at any purity according to a known method such as anion-exchange chromatography, hydrophobic chromatography, reversed phase chromatography, two-phase partition, recrystallization or the like.

Production Method 1-2

Among Compounds (Ia), a compound wherein $R^2$ is amino, i.e., a compound represented by formula (Iad):

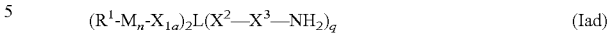

$$(R^1\text{-}M_n\text{-}X_{1a})_2 L(X^2\text{—}X^3\text{—}NH_2)_q \qquad (Iad)$$

wherein $R^1$, L, M, n, q, $X^{1a}$, $X^2$ and $X^3$ have the same meanings as described above, respectively, can be synthesized, for example, by treating Compound (Iac) obtained in Production Method 1-1 with an appropriate reducing agent. The reducing agent includes lithium aluminum hydride, sodium borohydride, sodium cyanoborohydride, hydrogen and the like.

Moreover, Compound (Iad) is also obtained by reacting Compound (Iai) obtained by Production Method 1 or a compound wherein the halogen moiety in Compound (Iai) is substituted with a tosyl group, with 5 equivalents to an excess amount of an diamine such as ethylenediamine, propylenediamine or the like in the presence of an appropriate base.

Furthermore, as shown in Production Method 1-1, Compound (Iad) can also be obtained by dissolving or suspending Compound (Iaj) in an appropriate solvent such as N,N-dimethylformamide, dimethyl sulfoxide, toluene, tetrahydrofuran or the like, reacting the compound with 1 to 50 mol of an activating agent such as succinimidyl carbonate, p-nitrophenyl chloroformate, carbonyldiimidazole or the like in the presence of 1 to 50 mol of an appropriate base such as sodium hydride, zinc oxide, sodium hydroxide, triethylamine or the like at −20 to 100° C. for 1 hour to 10 days to activate the compound, and reacting it with 1 equivalent to an excess amount of an diamine such as ethylenediamine, propylenediamine or the like in the presence of an appropriate base.

Also, Compound (Iad) can also be obtained, in accordance with the method shown in Production Method 1, by introducing at least one amino or protected form of amino into a compound such as a cyclic polyol or the like for forming L in advance, and replacing remaining two hydroxyl groups or halogen moieties of the compound with Polyalkylene Glycol A or a halide or tosylate thereof.

Among Compounds (Ia), a compound wherein $R^2$ is maleimido, i.e., a compound represented by formula (Iae):

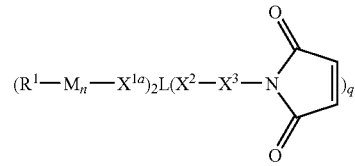

(Iae)

wherein $R^1$, L, M, n, q, $X^{1a}$, $X^2$ and $X^3$ have the same meanings as described above, respectively, can be obtained, for example, by reacting Compound (Iad) with N-alkoxycarbonylmaleimide in an aqueous saturated sodium hydrogen carbonate solution in accordance with the method of Oskar Keller, et al. [*Helv. Chim. Acta*, 58: 531 (1975)] or the method of Timothy P. Kogan [*Synthetic Commun.*, 22: 2417 (1992)]. As the N-alkoxycarbonylmaleimide, N-ethoxycarbonylmaleimide and N-methoxycarbonylmaleimide can be used.

Moreover, Compound (Iae) can also be obtained, in accordance with the method shown in Production Method 1, by introducing at least one maleimido into a compound such as a cyclic polyol or the like for forming L in advance, and replacing remaining two hydroxyl groups or halogen moieties of the compound with Polyalkylene Glycol A or a halide or tosylate thereof.

Compound (Iad), Compound (Iae) and synthetic intermediates thereof can be isolated or purified at any purity in a similar manner to the above.

Production Method 1-3

Among Compounds (Ia), a compound wherein $R^2$ is formyl, i.e., a compound represented by formula (Iaf):

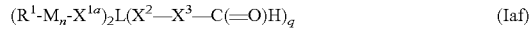

wherein $R^1$, L, M, n, q, $X^{1a}$, $X^2$ and $X^3$ have the same meanings as described above, respectively, can be obtained, for example, by oxidizing Compound (Iag) having hydroxymethyl as $R^2$ of Compounds (Ia) obtained in Production Method 1 with an appropriate oxidizing agent. The oxidizing agent includes pyridinium chlorochromate, chromic acid, silver ion, dimethyl sulfoxide and the like. Compound (Iaf) can also be obtained by reducing Compound (Iaa) with an appropriate reducing agent in a similar manner to the above.

Moreover, formyl can also be introduced by linking aminoethyl acetal, hydroxyethyl acetal, halogenated ethyl acetal, halogenated methyl acetal or the like to Compound (Iaj), Compound (Iai) or a compound wherein a halogen moiety in Compound (Iai) is substituted by a tosyl group, and then removing the acetal moiety.

Similarly, using Compound (Iaj) obtained in Production Method 1, formyl can also be introduced by activating a hydroxyl group in accordance with the method shown in Production Method 1-1, successively linking aminoethyl acetal, hydroxyethyl acetal or the like, and removing the acetal moiety.

Moreover, Compound (Iaf) can also be obtained, in accordance with the method shown in Production Method 1, by introducing at least one aldehyde or protected form of aldehyde into a compound such as a cyclic polyol or the like for forming L in advance, and replacing remaining two hydroxyl groups or halogen moieties of the compound with Polyalkylene Glycol A or a halide or tosylate thereof.

Compound (Iaf) and synthetic intermediates thereof can be isolated or purified at any purity in a similar manner to the above.

Production Method 1-4

Among Compounds (Ia), a compound wherein $R^2$ is halogenated carbonyl, i.e., a compound represented by formula (Iah):

(R$^1$-M$_n$-X$^{1a}$)$_2$L(X$^2$—X$^3$—C(=O)—Z$^1$)$_q$ (Iah)

wherein $Z^1$ represents a halogen; and $R^1$, L, M, n, q, $X^{1a}$, $X^2$ and $X^3$ have the same meanings as described above, respectively, can be obtained, for example, by heating Compound (Iaa) wherein $R^2$ is carboxy with a thionyl halide or in an appropriate mixed solvent of a thionyl halide and toluene, dimethylformamide or the like in the presence of an appropriate catalyst such as pyridine, triethylamine or the like at 0 to 150° C. for 1 to 24 hours.

The halogen in the halogenated carbonyl has the same meaning as the above halogen.

Production Method 1-5

Among Compounds (Ia), a compound wherein $R^2$ is halogenated lower alkyl, i.e., a compound represented by formula (Iai):

(R$^1$-M$_n$-X$^{1a}$)$_2$L(X$^2$—X$^3$—Z$^2$)$_q$ (Iai)

wherein $Z^2$ represents halogenated lower alkyl; and $R^1$, L, M, n, q, $X^{1a}$, $X^2$ and $X^3$ have the same meanings as described above, respectively, can be obtained, for example, by heating Compound (Iaj) wherein $R^2$ is a hydroxyl group with a thionyl halide or in an appropriate mixed solvent of a thionyl halide and toluene, dimethylformamide or the like in the presence of an appropriate catalyst such as pyridine or triethylamine at 0 to 150° C. for 1 to 24 hours. The halogen and the lower alkyl moiety in the halogenated lower alkyl have the same meanings as described above, respectively.

Moreover, Compound (Iai) is also obtained by reacting Compound (Iaj) obtained by Production Method 1 or Compound (Iad) wherein $R^2$ is amino with 5 equivalents to an excess amount of a dihalogenated alkyl such as dibromoethane, dibromopropane or the like in the presence of an appropriate base as described above.

Moreover, Compound (Iai) can also be obtained, in accordance with the method shown in Production Method 1, by introducing at least one halogenated lower alkyl into a compound such as a cyclic polyol or the like for forming L in advance, and replacing remaining two hydroxyl groups or halogen moieties of the compound with Polyalkylene Glycol A or a halide or tosylate thereof.

Compound (Iai) and synthetic intermediates thereof can be isolated or purified at any purity in a similar manner to the above.

Production Method 1-6

Among Compounds (Ia), a compound wherein $R^2$ is isocyanato, i.e., a compound represented by formula (Iak):

(R$^1$-M$_n$-X$^{1a}$)$_2$L(X$^2$—X$^3$—N=C=O)$_q$ (Iak)

wherein $R^1$, L, M, n, q, $X^{1a}$, $X^2$ and $X^3$ have the same meanings as described above, respectively, can be obtained, for example, by reacting Compound (Iad) with phosgene or oxalyl chloride in an appropriate solvent such as toluene, tetrahydrofuran, methylene chloride or the like at 0 to 150° C. for 1 to 24 hours, or by reacting the compound with N,N'-carbonyldiimidazole, followed by decomposition at room temperature.

Among Compounds (Ia), Compound (Iap) wherein $R^2$ is isothiocyanato can be produced in accordance with the above method with the exception that thiophosgene is used instead of phosgene.

Production Method 1-7

Among Compounds (Ia), a compound wherein $R^2$ is succinimidooxycarbonyl, substituted or unsubstituted aryloxycarbonyl, benzotriazolyloxycarbonyl or phthalimidooxycarbonyl, i.e., a compound represented by formula (Ial):

(R$^1$-M$_n$-X$^{1a}$)$_2$L(X$^2$—X$^3$—R$^{2a}$)$_q$ (Ial)

wherein $R^{2a}$ represents succinimidooxycarbonyl, substituted or unsubstituted aryloxycarbonyl, benzotriazolyloxycarbonyl, or phthalimidooxycarbonyl; and $R^1$, L, M, n, q, $X^{1a}$, $X^2$ and $X^3$ have the same meanings as described above, respectively, can be obtained, for example, in accordance with the usual synthetic method for esters. For example, an objective compound can be obtained by reacting 1 to 10 mol of N-hydroxysuccinimide, substituted or unsubstituted hydroxyaryl, N-hydroxybenzotriazole, N-hydroxyphthalimide or the like with 1 mol of Compound (Iaa) in the presence of 1 to 10 mol of a condensing agent such as N,N'-dicyclohexylcarbodiimide or the like in an appropriate solvent such as dimethylformamide, methylene chloride, dimethyl sulfoxide or the like at −20 to 100° C. for 1 to 24 hours. More specifically, an objective compound can be obtained in accordance with the method of introducing a carboxyl group into the terminal of a polyalkylene glycol, the method of producing N-hydroxysuccinimide ester of carboxymethylpolyalkylene glycol or the like by A. Fradet, et al. [*Polym. Bull*, 4: 205 (1981)] or K. Geckeler, et al. [*Polym. Bull.*, 1: 691 (1979)].

The substituted or unsubstituted aryloxycarbonyl has the same meaning as described above. The aryl has the same meaning as described above, and the substituent of the substituted aryl has the same meaning as each substituent in the substituted aryloxycarbonyl, substituted aryloxycarbonyloxy, substituted aryl disulfide and substituted aroyloxycarbonyl.

Production Method 1-8

Among Compounds (Ia), a compound wherein $R^2$ is vinylsulfonyl, i.e., a compound represented by formula (Iam):

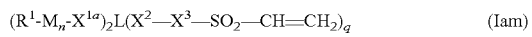

(Iam)

wherein $R^1$, L, M, n, q, $X^{1a}$, $X^2$ and $X^3$ have the same meanings as described above, respectively, can be produced, for example, according to the method of Margherita Morpurgo, et al. [*Bioconjugate Chem.*, 7: 363 (1996)] using Compound (Iaj).

Production Method 1-9

Among Compounds (Ia), a compound wherein $R^2$ is substituted or unsubstituted lower alkoxycarbonyloxy or substituted or unsubstituted aryloxycarbonyloxy, i.e., a compound represented by formula (Ian):

(Ian)

wherein $R^{2b}$ represents substituted or unsubstituted lower alkoxycarbonyloxy or substituted or unsubstituted aryloxycarbonyloxy; and $R^1$, L, M, n, q, $X^{1a}$, $X^2$ and $X^3$ have the same meanings as described above, respectively, can be obtained, for example, by reacting Compound (Iaj) wherein $R^2$ is a hydroxyl group with an excess amount of p-nitrophenyl chloroformate, ethyl chloroformate or the like in the presence of an appropriate base such as demethylaminopyridine, triethylamine or the like in accordance with the method of Talia Miron and Meir Wilcheck [*Bioconjugate Chem.*, 4: 568 (1993)].

Moreover, Compound (Ian) can also be obtained, in accordance with the method shown in Production Method 1, by introducing at least one substituted or unsubstituted lower alkoxycarbonyloxy or substituted or unsubstituted aryloxycarbonyloxy into a compound such as a cyclic polyol or the like for forming L in advance, and replacing remaining two hydroxyl groups or halogen moieties of the compound with Polyalkylene Glycol A or a halide or tosylate thereof.

Compound (Ian) and synthetic intermediates thereof can be isolated or purified at any purity in a similar manner to the above.

The substituted or unsubstituted lower alkoxycarbonyloxy or substituted or unsubstituted aryloxycarbonyloxy has the same meaning as described above.

PRODUCTION METHOD 2

Compound Wherein $X^1$ is S

Among Compounds (I), Compound (Ib) wherein $X^1$ is S, can be obtained, for example, as Production Method 1, by reacting a compound obtained by converting a cyclic polyol into a cyclic polyhalide [Edited by The Chemical Society of Japan, *Experimental Chemistry Course*, Fourth edition (1992), vol. 19, Maruzen] or a commercially available cyclic polyhalide with a thiol derivative of Polyalkylene Glycol A in an appropriate solvent in the presence of an appropriate base.

Moreover, Compound (Ib) can also be obtained by reacting a halide or tosylate of Polyalkylene Glycol A with a cyclic polythiol, which is the reverse of the above process.

The thiol derivative of Polyalkylene Glycol A is commercially available or can be prepared by the methods summarized by Samuel Zalipsky [*Bioconjugate Chem.*, 6: 150 (1995)].

The reaction conditions and purification conditions of each step are determined in accordance with Production Method 1.

Production Method 2-1

Among Compounds (Ib), a compound wherein $R^2$ is carboxy, carbamoyl, cyano, amino, maleimido, formyl, halogenated carbonyl, halogenated lower alkyl, isocyanato, isothiocyanato, succinimidooxycarbonyl, substituted or unsubstituted aryloxycarbonyl, benzotriazolyloxycarbonyl, phthalimidooxycarbonyl, vinylsulfonyl, substituted or unsubstituted lower alkoxycarbonyloxy or substituted or unsubstituted aryloxycarbonyloxy can be obtained by combining the methods described in Production Methods 1-1 to 1-9 after the compound wherein $X^1$ is —S— is produced according to Production Method 2.

PRODUCTION METHOD 3

Compound Wherein $X^1$ is $NR^3$

Among Compounds (I), Compound (Ic) wherein $X^1$ is $NR^3$ in which $R^3$ has the same meaning as described above can be obtained, for example, as Production Method 1, by reacting a compound obtained by converting a cyclic polyol into a cyclic polyamine or a commercially available cyclic polyamine with a halide or tosylate of Polyalkylene Glycol A in an appropriate solvent in the presence of an appropriate base.

Compound (Ic) can also be obtained by reacting an amino derivative of Polyalkylene Glycol A with a cyclic polyhalide.

Moreover, Compound (Ic) can also be obtained by dissolving or suspending 1 equivalent of a cyclic polyaldehyde and 1 to 10 equivalents of an amino derivative of Polyalkylene Glycol A in an appropriate solvent such as methanol, ethanol, dimethyl formamide, acetonitrile, dimethyl sulfoxide, water, buffer or the like and reacting them in the presence of 1 to 100 equivalents of a reducing agent such as sodium cyanoborohydride, sodium borohydride or the like at −20 to 100° C.

Furthermore, Compound (Ic) can also be produced using a cyclic polyamine and an aldehyde derivative of Polyalkylene Glycol A.

As the above cyclic polyaldehyde, a commercially available one may be used as it is, a compound obtained by oxidizing a cyclic polyalcohol may be used, or a compound obtained by reducing a cyclic polycarboxylic acid may be used. Moreover, as the aldehyde derivative of Polyalkylene Glycol A, a commercially available one may be used or a compound obtained by oxidizing alcohol present at the terminal of Polyalkylene Glycol A may be used.

The reaction conditions and purification conditions of each step are determined in accordance with Production Method 1.

Production Method 3-1

Among Compounds (Ic), a compound wherein $R^2$ is carboxy, carbamoyl, cyano, amino, maleimido, formyl, halogenated carbonyl, halogenated lower alkyl, isocyanato, isothiocyanato, succinimidooxycarbonyl, substituted or unsubstituted aryloxycarbonyl, benzotriazolyloxycarbonyl, phthalimidooxycarbonyl, vinylsulfonyl, substituted or unsubstituted lower alkoxycarbonyloxy or substituted or unsubstituted aryloxycarbonyloxy, can be obtained by combining the methods described in Production Methods 1-1 to 1-9 after Compound (Ic) is produced according to Production Method 3.

PRODUCTION METHOD 4

Compound Wherein $X^1$ is $R^4$—NH—C(=O)—$R^5$ or $R^6$—C(=O)—NH—$R^7$

Among Compounds (I), Compound (Ida) wherein $X^1$ is $R^4$—NH—C(=O)—$R^5$ in which $R^4$ and $R^5$ have the same meanings as described above, respectively, can be obtained, for example, by dissolving or suspending a cyclic polycarboxylic acid compound selected from cyclohexanetricarboxylic acid, Kemp's triacid and the like in an appropriate solvent such as N,N-dimethylformamide, dimethyl sulfoxide or the like, adding 1 to 30 equivalents of an alcohol compound such as N-hydroxysuccinimide, N-hydroxyphthalimide, N-hydroxybenzotriazole, p-nitorophenol or the like and 1 to 30 equivalents of a condensing agent such as N,N'-dicyclohexylcarbodiimide, benzotriazol-1-yloxytripyrrolidinophosphonium hexafluorophosphate or the like, and then adding 1 to 3 equivalents of an amino derivative of Polyalkylene Glycol A, and reacting them according to a peptide synthetic method [Izumiya, et al., *Basis and Experiment of Peptide Synthesis* (Peptide gosei no kiso to jikken), (1985), Maruzen]. The reaction is carried out under anhydrous conditions at −20 to 100° C. for 1 hour to 10 days.

Moreover, a reaction liquid containing a double-chain branched polyethylene glycol derivative wherein $R^2$ is carboxy at a high purity, can also be obtained by protecting at least one carboxy group in a cyclic polycarboxylic acid molecule with an appropriate protective group such as methyl, ethyl, benzyl, tert-butyl or the like, introducing an amino derivative of Polyalkylene Glycol A into remaining two carboxy groups according to the above method, and successively removing the protective group of the carboxy group according to a usual deprotection method. In this case, a method used in usual peptide synthesis [Izumiya, et al., *Basis and Experiment of Peptide Synthesis* (Peptide gosei no kiso to jikken) (1985), Maruzen] can be used for the introduction of the protective group of carboxylic acid and the removal of the protective group. The configuration of the carboxy in the cyclic polycarboxylic acid may include the steric configuration, and an amino derivative of Polyalkylene Glycol A having any average molecular weight may be used, so long as the molecular weight distribution is uniform (preferably Mw/Mn is 1.1 or less).

Furthermore, among Compounds (I), Compound (Idb) wherein $X^1$ is $R^6$—C(=O)—NH—$R^7$ in which $R^6$ and $R^7$ have the same meanings as described above, respectively, can also be obtained by the method of reacting a cyclic polyamine with an active ester of a carboxylic acid derivative of Polyalkylene Glycol A or an acid halide derivative of Polyalkylene Glycol A, which is a reverse to the above process. The acid halide derivative of Polyalkylene Glycol A can be obtained by heating a carboxylic acid derivative of Polyalkylene Glycol A with a thionyl halide or in an appropriate mixed solvent of a thionyl halide and toluene, dimethylformamide or the like in the presence of an appropriate catalyst such as pyridine, triethylamine or the like at 0 to 150° C. for 1 to 24 hours.

The reaction conditions and purification conditions of each step are determined in accordance with the above production methods.

Production Method 4-1

Among Compounds (Ida) and (Idb), a compound wherein $R^2$ is carboxy, carbamoyl, cyano, amino, maleimido, formyl, halogenated carbonyl, halogenated lower alkyl, isocyanato, isothiocyanato, succinimidooxycarbonyl, substituted or unsubstituted aryloxycarbonyl, benzotriazolyloxycarbonyl, phthalimidooxycarbonyl, vinylsulfonyl, substituted or unsubstituted lower alkoxycarbonyloxy or substituted or unsubstituted aryloxycarbonyloxy can be obtained by combining the methods described in Production Methods 1-1 to 1-9 after Compound (Ida) or Compound (Idb) is produced according to Production Method 4.

PRODUCTION METHOD 5

Compound Wherein $X^1$ is $R^8$—C(=O)—O or O—C(=O)—$R^9$

Among Compounds (I), Compound (Ie) wherein $X^1$ is $R^8$—C(=O)—O in which $R^8$ has the same meaning as described above, or O—C(=O)—$R^9$ in which $R^9$ has the same meaning as described above, can be obtained, for example, by dehydrative condensation using a combination of Polyalkylene Glycol A and a cyclic polycarboxylic acid or a carboxylic acid derivative of Polyalkylene Glycol A and a cyclic polyol. As a method for the dehydrative condensation, a method for dehydration in the presence of an acid or base catalyst as is used in a usual ester synthesis or a method of condensing a corresponding alcohol compound and carboxylic acid using a condensing agent such as N,N'-dicyclohexylcarbodiimide or the like in an appropriate solvent such as dimethylformamide, dimethyl sulfoxide, acetonitrile, pyridine, methylene chloride or the like may be used. Furthermore, an objective compound can also be synthesized by reacting an acid halide with a corresponding alcohol compound in the above process.

The reaction conditions and purification conditions of each step are determined in accordance with the above production methods.

Production Method 5-1

Among Compounds (Ie), a compound wherein $R^2$ is carboxy, carbamoyl, cyano, amino, maleimido, formyl, halogenated carbonyl, halogenated lower alkyl, isocyanato, isothiocyanato, succinimidooxycarbonyl, substituted or unsubstituted aryloxycarbonyl, benzotriazolyloxycarbonyl, phthalimidooxycarbonyl, vinylsulfonyl, substituted or unsubstituted lower alkoxycarbonyloxy or substituted or unsubstituted aryloxycarbonyloxy can be obtained by combining the methods described in Production Methods 1-1 to 1-9 after Compound (Ie) is produced according to Production Method 5.

PRODUCTION METHOD 6

Compound Wherein $X^1$ is $R^{6a}$—O—C(=O)—NH— or $R^4$—NH—C(=O)—O

Among Compounds (I), Compound (Ifa) wherein $X^1$ is $R^{6a}$—O—C(=O)—NH— in which $R^{6a}$ has the same meaning as described above, can be produced, for example, as follows.

A crude product containing Compound (Ifa) is obtained by reacting a commercially available cyclic polyamine or a cyclic polyamine prepared from a cyclic polyol by combining the above production methods with 1 to 3 mol excess of a carbonate derivative of Polyalkylene Glycol A. Also, the carbonate derivative of Polyalkylene Glycol A can be produced according to the method of Talia Miron, et al. [*Bioconjugate Chem.*, 4: 568 (1993)]. In addition, as the carbonate derivative of Polyalkylene Glycol A, N-hydroxysuccinimidyl carbonate, p-nitrophenyl carbonate, an imidazolylcarbonyloxy derivative or the like may be used.

Among Compounds (I), Compound (Ifb) wherein $X^1$ is $R^4$—NH—C(=O)—O in which $R^4$ has the same meaning as described above, can be produced, for example, as follows.

Compound (Ifb) can be obtained by reacting a carbonate derivative of a cyclic polyol with an amino derivative of Polyalkylene Glycol A in a similar manner to the above.

By combining protection and deprotection of a functional group in accordance with other production methods, Compound (Ifa) or Compound (Ifb) can be selectively formed.

The reaction conditions and purification conditions of each step are determined in accordance with the above production methods.

Production Method 6-1

Among Compounds (If), a compound wherein $R^2$ is carboxy, carbamoyl, cyano, amino, maleimido, formyl, halogenated carbonyl, halogenated lower alkyl, isocyanato, isothiocyanato, succinimidooxycarbonyl, substituted or unsubstituted aryloxycarbonyl, benzotriazolyloxycarbonyl, phthalimidooxycarbonyl, vinylsulfonyl, substituted or unsubstituted lower alkoxycarbonyloxy or substituted or unsubstituted aryloxycarbonyloxy can be obtained by combining the methods described in Production Methods 1-1 to 1-9 after Compound (If) is produced according to Production Method 6.

It is possible that a single-chain compound is obtained by linking $R^1$-$M_n$-$X^1$ to L and then a double-chain compound is obtained by linking $R^1$-$M_n$-$X^1$ which is the same or different from the above to L through the same reaction. For example, a polyalkylene glycol is linked to one functional group in L to obtain a single-chain compound using any of the reactions of the methods shown in Production Methods 1 to 6. The content of the single-chain compound formed can be controlled by changing the ratio of the polyalkylene glycol to the starting material constructing the structure of L moiety, and thus it is possible to produce the single-chain compound as a main component. The obtained single-chain compound can be used in the next step at a purity as it is or after purifying it at any purity or a high purity in accordance with the method shown in Production Method 1.

The single-chain compound thus obtained is linked to a polyalkylene glycol which is the same as or different from the above in accordance with any of the method shown in Production methods 1 to 6 to prepare a double-chain compound. Also, the second polyalkylene glycol may be subjected to the same reaction as the reaction from which the single-chain compound has been obtained but may also be subjected to a different reaction so as to have a different linking form. For example, when a compound having at least two functional groups such as a hydroxyl group, amino, carboxy and the like is used as a starting material for constructing the structure of L moiety, it is possible that a single-chain compound wherein $X^1$ is O is first obtained by the method shown in Production Method 1 and then a second polyalkylene glycol may be allowed to react so that $X^1$ becomes $R^4$—NH—C(=O)—$R^5$ according to the Production Method 4. As described above, a double-chain compound wherein two polyalkylene glycols are linked to L in the same or different linking form can be obtained. Furthermore, the molecular weights of the first and second polyalkylene glycols may be different from each other, and an objective compound can be easily obtained using a polyalkylene glycol having a different average molecular weight in the reaction of linking each polyalkylene glycol to L.

Moreover, in the reaction of introducing a polyalkylene glycol into L, it is possible that at least one functional group in L (for example, in Production Method 1, at least one hydroxyl group) is left intact and, after other functional groups are protected with an appropriate protective group, L is allowed to react with a polyalkylene glycol for linking, and then the protective group is removed.

The branched polyalkylene glycols of the present invention can be obtained in accordance with the above production methods even if they are compounds other than the compounds specifically shown in the above production method.

As described above, the polyalkylene glycols as starting materials in Production Methods 1 to 6 are commercially available but can also be easily produced by various methods summarized by Samuel Zalipsky [*Bioconjugate Chem.*, 6: 150 (1995)].

The obtained branched polyalkylene glycols can be purified as branched polyalkylene glycols having any purity by the method such as silica gel chromatography, reversed phase chromatography, hydrophobic chromatography, ion-exchange chromatography, gel filtration chromatography, recrystallization, extraction or the like.

The resulting branched polyalkylene glycols can be linked to an amino acid side chain, an N-terminal amino group or a C-terminal carboxyl group of the above physiologically active polypeptide directly or through a spacer.

As the spacer, an amino acid or peptide is preferable but other compound may be used, so long as it can link to the polyalkylene glycol. A natural amino acid such as lysine, cysteine or the like may be used and also ornithine, diaminopropionic acid, homocysteine or the like may be used. Cysteine is more preferable. As the peptide, a peptide of 2 to 10 amino acid residues is preferred. The spacer other than an amino acid or peptide includes glycerol, ethylene glycol, sugar and the like. The sugar includes monosaccharides such as glucose, galactose, sorbose, galactosamine, lactose, etc., disaccharides, and the like.

The spacer is linked to a side chain of the residue of lysine, cysteine, arginine, histidine, serine, threonine and the like in a physiologically active polypeptide molecule through an amide bond, a thioester bond, an ester bond, etc., a C-terminal carboxyl group of the polypeptide through an amide bond or an ester bond, or an N-terminal amino group of the polypeptide through an amide bond. These linkages can be carried out using usual peptide synthesis [Izumiya, et al., *Fundamentals and Experiments of Peptide Synthesis* (1985), Maruzen] or gene recombination.

In this case, it is preferable to introduce an amino acid, a peptide or the like into the C-terminal carboxylic acid as a spacer at the same time when a physiologically active polypeptide is synthesized, but the spacer may be linked after the synthesis of the physiologically active polypeptide. Moreover, the C-terminal carboxylic acid or the like of the polypeptide may be activated in a chemical synthetic manner and then linked to a spacer. Also, a spacer to which a polyalkylene glycol is linked in advance may be linked to a physiologically active polypeptide according to the above method.

The physiologically active polypeptide used in the present invention includes a polypeptide, an antibody, derivatives thereof and the like. Examples of the polypeptide include enzymes such as asparaginase, glutaminase, arginase, uricase, superoxide dismutase, lactoferin, streptokinase, plasmin, adenosine deaminase, plasminogen activator, plasminogen, etc.; cytokine such as interleukin-1 to 18, interferon-α, interferon-β, interferon-γ, interferon-ω, interferon-τ, granulocyte-colony stimulating factor, thrombopoietin, erythropoietin, tumor necrosis factor, fibrobrast growth factor-1 to 18, midkine, epidermal growth factor, osteogenic protein 1, stem cell factor, vascular endothelial growth factor, transforming growth factor, hepatocyte growth factor, etc.; hormones such as glucagon, parathyroid hormone, glucagon like peptide, etc.; klotho protein; angiopoietin; angiostatin; leptin; calcitonine; amylin; insulin like growth factor 1; endostatin; and the like.

The antibody used in the present invention can be obtained as a polyclonal antibody or a monoclonal antibody using a known method [*Antibodies-A Laboratory Manual*, Cold Spring Harbor Laboratory (1988)].

As the antibody used in the present invention, any of a polyclonal antibody or a monoclonal antibody can be used but a monoclonal antibody is preferred.

The monoclonal antibody used in the present invention includes an antibody produced by a hybridoma, a humanized antibody, the antibody fragment thereof and the like.

The humanized antibody includes a human chimeric antibody, a human CDR-grafted antibody and the like.

A human chimeric antibody is an antibody comprising a heavy chain variable region (hereinafter, also referred to as "HV" or "VH", the heavy chain being referred to as "H chain" and the variable region as "V region") and a light chain valuable region (hereinafter, also referred to as "LV" or "VL", the light chain being referred to as "L chain") of an antibody derived from an animal other than human and a heavy chain constant region (hereinafter, also referred to as CH, the constant region being referred to as C region) of an human antibody and a light chain valuable region (hereinafter, also referred to as "CL") of an human antibody. As the animal other than human, any animal such as mouse, rat, hamster, rabbit or the like may be used, so long as it is capable of preparing a hybridoma cell.

A human CDR-grafted antibody is an antibody wherein amino acid sequences of CDRs of V regions of H chain and L chain of an antibody derived from an animal other than human are grafted at an appropriate positions of V regions of H chain and L chain of a human antibody.

The antibody fragment includes Fab, Fab', F(ab')$_2$, a single chain antibody, a disulfide-stabilized V region fragment, a peptide comprising a complementarity determining region, and the like.

An Fab is a fragment having about 50,000 molecular weight and an antigen binding activity, which is constituted by about half of the N-terminal side of H chain obtained by digesting the upper peptide side of two disulfide bonds crosslinking two H chains in the hinge regions of IgG with papain, and the full L chain.

An Fab' is an antibody fragment having about 50,000 molecular weight and an antigen binding activity, which is obtained by cutting a disulfide bond of the hinge regions of the above F(ab')$_2$.

An F(ab')$_2$ is a fragment having about 100,000 molecular weight and an antigen binding activity, which is constituted by two Fab regions bound at the hinge regions which are obtained by digesting the lower side of two disulfide bonds in the hinge regions of IgG with trypsin.

A single chain antibody (hereinafter also referred to as "scFv") is a VH—P—VL or VL—P—VH polypeptide in which one VH and one VL are linked using an appropriate peptide linker (hereinafter referred to as "P"). The VH and VL comprised in the scFv of the present invention may be any of the monoclonal antibody or the human CDR-grafted antibody of the present invention.

A disulfide-stabilized V region fragment (hereinafter referred to as "dsFv") is an antibody in which polypeptides prepared by substituting one amino acid residue in each of VH and VL with a cysteine residue are linked via a disulfide bond. The amino acid residue substituted with a cysteine residue can be selected based on the three-dimensional structure estimation of the antibody in accordance with the method shown by Reiter et al. (*Protein Engineering*, 7, 697 (1994)). As the VH or VL comprised in the dsFv of the present invention, any of the monoclonal antibody or the human CDR-grafted antibody can be used.

The derivatives of a physiologically active polypeptide include amino acid-replaced derivatives, amino acid-deleted derivatives, sugar chain-added derivatives, sugar chain-deleted derivatives, partial peptides and the like.

As the above physiologically active polypeptide, an enzyme, a cytokine, a hormone and the like are preferred. More preferred examples include interferon such as interferon-β, interferon-α, interferon-γ, etc.; granulocyte-colony stimulating factor; superoxide dismutase; and the like. Chemically modified polypeptides thereof are also preferred.

As the chemically modified polypeptide obtained by chemical modification of the above physiologically active polypeptide, a chemically modified polypeptide obtained by chemical modification of interferon is preferred and a medicament comprising the chemically modified polypeptide is also preferred. Moreover, the medicament comprising the chemically modified polypeptide obtained by chemical modification of interferon includes a therapeutic agent for multiple scleroses, a therapeutic agent for hepatitis, a therapeutic agent for diseases involving blood vessel angiogenesis, a therapeutic agent for malignant tumors, a therapeutic agent for eye diseases, a therapeutic agent for skin diseases and the like comprising a chemically modified polypeptide obtained by chemical modification of interferon, but a therapeutic agent for multiple scleroses is preferred.

The physiologically active polypeptides can be obtained by the method of extraction from animal organs and tissues but can also be produced by usual peptide synthesis or gene recombination. Furthermore, commercially available polypeptides can also be used.

Moreover, as the polypeptide used in the reaction, a roughly purified polypeptides can be used, and a polypeptide purified at a purity suitable for chemical modification according to a purification method such as gel filtration chromatography, ion-exchange chromatography, hydrophobic chromatography, reversed phase chromatography, extraction or the like can also be used.

The polypeptide is produced in a buffer such as a phosphate buffer, a borate buffer, an acetate buffer, a citrate buffer or the like, water, an appropriate organic solvent such as N,N-dimethylformamide, dimethyl sulfoxide, dioxane, tetrahydrofuran or the like, or in a mixed solvent of the organic solvent and an aqueous solution, and then used in a chemical modification reaction.

The branched polyalkylene glycols of the present invention can also be used for site-specific covalent modification of polypeptides, more specifically and preferably all natural or recombinant polypeptides having a free cysteine residue, such as granulocyte-colony stimulating factor, erythropoietin, interferons, interleukins and the like.

The physiologically active polypeptide modified with a branched polyalkylene glycol of the present invention is produced by reacting a branched polyalkylene glycol in an amount of about 1 to 1000 mol, preferably about 1 to 50 mol per mol of a physiologically active polypeptide. The degree of modification of the physiologically active polypeptide with the branched polyalkylene glycol can be arbitrarily selected by controlling the molar ratio of the branched polyalkylene glycol to the physiologically active polypeptide, reaction temperature, pH, reaction time or the like. Moreover, the solvent used in the reaction is not limited, so long as it does not inhibit the reaction, and can be selected from any solvents, for example, a phosphate buffer, a borate buffer, a tris-hydrochloride buffer, an aqueous sodium hydrogen carbonate solution, a sodium acetate buffer, N,N-dimethylformamide, dimethyl sulfoxide, methanol, acetonitrile, dioxane or the like. The temperature, pH and time of the reaction are not limited, so long as the conditions do not damage the activity of the physiologically active polypeptide, and, for example, they are preferably at 0 to 50° C. and pH 4 to 10 for 10 minutes to 100 hours.

The physiologically active polypeptide modified with a branched polyalkylene glycol of the present invention can be purified by gel filtration, ion-exchange chromatography, reversed phase high performance liquid chromatography, affinity chromatography, ultrafiltration or the like according to a usual method. The confirmation of the polypeptide structure in the synthesized or purified physiologically active polypeptide or the physiologically active polypeptide modified with a branched polyalkylene glycol of the present invention can be carried out by mass spectrometry, nuclear magnetic resonance (NMR), and amino acid composition analysis on an amino acid analyzer, and also by amino acid sequence analysis using reversed phase HPLC by analyzing phenylthiohydantoin (PTH) amino acid, which is obtained from Edman degradation by means of a gas phase protein sequencer or the like.

The chemically modified polypeptide of the present invention can be administered in a form of a pharmaceutical composition for human or animals, and the composition can be produced by a usual method for preparing pharmaceuticals.

For the method for administration oral, intravenous, subrcutaneous, submuscular, intraperitoneal, or percutaneous administration, other acceptable method or the like are possible, and a composition suitable for the administration can be used. Common additives, such as an isotonicity, a buffering agent, an excipient, a pH regulator, a stabilizing agent, an antiseptic, a solubilizing agent, a wetting agent, an emulsifier, a lubricant, a sweetener, a coloring agent, an antioxidant and the like can be added to the formulations.

Examples of Compound (I) are shown in Table 1.

TABLE 1

| Compound No. Abbreviation | $X^1$ | $[CH_3-(OCH_2CH_2)_n-X^1]_2L(X^2-X^3-R^2)_q$ (I)<br>q | L | $X^2-X^3-R^2$ |
|---|---|---|---|---|
| 1<br>5CHTO(2UU) | $-CH_2-\overset{H}{N}-\overset{O}{\overset{\|}{C}}-O-$ | 1 | (cyclohexane with three substituents) | $-O-\overset{O}{\overset{\|}{C}}-O-N\overset{O}{\underset{O}{\diagup}}$ |
| 2<br>5CHTC(2AA) | $-CH_2-\overset{H}{N}-\overset{O}{\overset{\|}{C}}-$ | 1 | (cyclohexane with three substituents) | $-\overset{O}{\overset{\|}{C}}-OH$ |
| 3<br>5CHTO(2EA) | $-O-$ | 1 | (cyclohexane with three substituents) | $-O-(CH_2)_2COOH$ |
| 4<br>5CHTM(2EA) | $-O-CH_2-$ | 1 | (cyclohexane with three substituents) | $-CH_2-O-(CH_2)_2COOH$ |

TABLE 1-continued $[CH_3—(OCH_2CH_2)_n—X^1]_2L(X^2—X^3—R^2)_q$ (I)

| Compound No. | $X^1$ | q | L | $X^2—X^3—R^2$ |
|---|---|---|---|---|
| 5 5CHTM(2EU) | —O—CH$_2$— | 1 | (cyclohexane) | —H$_2$C—O—C(=O)—O—N(succinimide) |
| 6 5QNA(2UA) | —NH—C(=O)—O— | 2 | (cyclohexane with COOH) | —(OH)$_2$ |
| 7 5SKA(2UA) | —NH—C(=O)—O— | 1 | (cyclohexene with COOH) | —OH |
| 8 5CHTM(2URa) | —NH—C(=O)—O—CH$_2$— | 1 | (cyclohexane) | —CH$_2$—O—(CH$_2$)$_2$—CHO |
| 9 5CHTM(2UM) | —CH$_2$—NH—C(=O)—O—CH$_2$— | 1 | (cyclohexane-CH$_2$—O—C(=O)—NH—butyl) | —N(maleimide) |
| 10 5CHTM(2EA2) | —O—CH$_2$— | 1 | (cyclohexane) | —CH$_2$—O—CH$_2$COOH |
| 37 5CHTM(2UA) | —CH$_2$—NH—C(=O)—O— | 1 | (cyclohexane) | —O—CH$_2$—COOH |
| 11 | —O— | 1 | (cyclohexane) | —O—(CH$_2$)$_3$NH$_2$ |
| 12 | —O—CH$_2$— | 1 | (cyclohexane) | —CH$_2$—OH |

TABLE 1-continued

| Compound No. | $X^1$ | $[CH_3-(OCH_2CH_2)_n-X^1]_2L(X^2-X^3-R^2)_q$ q | L | $X^2-X^3-R^2$ (I) |
|---|---|---|---|---|
| 13 | —O—CH$_2$— | 1 | 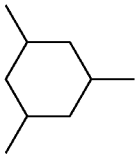 |  |
| 14 | —O— | 1 | | —O—(CH$_2$)$_2$C(=O)Cl |
| 15 | —O—CH$_2$— | 1 | | —CH$_2$—Br |
| 16 | —O— | 1 | | —O—(CH$_2$)$_3$N=C=O |
| 17 | —O—C(=O)—NH—(CH$_2$)$_3$—O— | 1 | | —O—(CH$_2$)$_3$NH$_2$ |
| 18 | —CH$_2$—NH—C(=O)— | 1 | | —C(=O)—OH |

The activities of the physiologically active polypeptides and chemically modified physiologically active polypeptides are explained below.

TEST EXAMPLE 1

Antiviral Activity of Chemically Modified Interferon-β

The antiviral activities of chemically modified rhIFN-β and chemically modified naturally occurring-type rhIFN-β obtained in Examples 11 to 15 and Example 33, unmodified rhIFN-β and unmodified naturally occurring-type hIFN-β were examined by the following neutral red-uptake method.

<NR-uptake Method>

An antiviral activity was measured with reference to the method of Kohase et al. [*Protein, Nucleic acid, Enzyme* (additional volume), p. 355 (1981)].

Namely, 5% fetal bovine serum (FBS)-added eagle MEM medium was added to a sterilized transfer plate. Then, each 50 μl of IFN domestic standard [α(manufactured by The Green Cross) and β (manufactured by Toray)] solution was dispensed into the well and stepwise dilution was carried out twice by twice. On the other hand, each 50 μl of a chemically modified IFN or unmodified IFN solution prepared with a medium at a predetermined concentration was similarly dispensed to the well. The solutions were transferred into a 96-well plate in which a predetermined cell number of an established cell line (FL cell) derived from human amnion had been placed, followed by mixing for several seconds. The mixture was cultured in a CO$_2$ incubator at 37° C. for overnight to form antiviral conditions.

Then, after the culture liquid was removed, a viral solution was added, followed by culturing in a CO$_2$ incubator at 37° C. for 2 days to be infected with the virus. The antiviral state of the cell was changed by IFN and a cytopathy occurred. Thereafter, the culture liquid was removed and an NR solution was added thereto. The mixture was incubated at 37° C. for 1 hour in a $CO_2$ incubator and the NR solution was removed. The well was washed with an isotonic phosphate buffer and an extracting liquid (0.01 mol/L hydrochloric acid-30% ethanol) was added thereto, followed by mixing for 2 to 3 minutes.

The surviving cells were stained with NR. After extraction, the absorbance at 492 nm was measured and a standard curve was plotted. A relative activity of a chemically modified IFN was calculated by defining the activity of unmodified IFN calculated from the standard curve as 100%.

The specific activity of each IFN-β is shown in Tables 2, 3 and 4.

TABLE 2

Antiviral activity of chemically modified recombinant hIFN-β

| Compound abbreviation | Example | Relative activity (%) |
|---|---|---|
| Unmodified rhIFN-β | — | 100 |
| 5CHTO(2UU)-rhIFN-β | 11 | 96 |
| 5CHTC(2AA)-rhIFN-β | 12 | 122 |
| 5CHTO(2EA)-rhIFN-β | 13 | 90 |
| 5CHTM(2EA)-rhIFN-β | 14 | 116 |

TABLE 3

Antiviral activity of chemically modified natural hIFN-β

| Compound abbreviation | Example | Relative activity (%) |
|---|---|---|
| Unmodified natural hIFN-β | — | 100 |
| 5CHTM(2EA)-natural hIFN-β | 15 | 104 |

TABLE 4

Antiviral activity of chemically modified recombinant human [17]Ser IFN-β

| Compound abbreviation | Example | Relative activity (%) |
|---|---|---|
| Unmodified [17]Ser rhIFN-β | — | 100 |
| 5CHTM(2EA)-[17]Ser rhIFN-β | 33 | 70 |

It was confirmed that all the chemically modified rhIFN-β of the present invention retained antiviral activity.

TEST EXAMPLE 2

Antiviral Activity of Chemically Modified Interferon-α

The antiviral activities of chemically modified rhIFN-α obtained in Examples 16 to 17 and unmodified rhIFN-α were examined by the NR-uptake method described in Test Example 1.

Table 5 shows the activity at the time when each IFN-α was allowed to act at a concentration of 1 µg/ml (designated by defining the activity of unmodified IFN as 100%).

TABLE 5

Antiviral activity of chemically modified IFN-α

| Compound Abbreviation | Example | Concentration (µg/ml) | Relative activity (%) |
|---|---|---|---|
| 5CHTC(2AA)-rhIFN-α | 16 | 1 | 100 |
| 5CHTM(2EA)-rhIFN-α | 17 | 1 | 100 |
| Unmodified rhIFN-α | — | 1 | 100 |

It was confirmed that all the chemically modified rhIFN-α retained antiviral activity.

TEST EXAMPLE 3

Growth-accelerating Activity of Chemically Modified Recombinant Human Granulocyte-colony Stimulating Factor on Mouse Leukemia Cell NFS60 :

The growth-accelerating activities of the compounds of Examples 20 to 23, Example 25 and Example 26, unmodified rhG-CSF derivative and unmodified rhG-CSF against mouse leukemia cell NFS60 [Proc. Natl, Acad, Sci. USA, 82: 6687 (1985)] were measured according to the method of Asano et al. [Japanese Pharmacology & Therapeutics, 19: 2767 (1991)].

Tables 6 and 7 shows the results when each compound was allowed to act at a concentration of 100 ng/ml by defining the activity of unmodified peptide as 100%.

TABLE 6

NFS60 cell growth-accelerating activity of chemically modified rhG-CSF derivatives

| Compound Abbreviation | Example | Concentration (ng/ml) | Relative activity (%) |
|---|---|---|---|
| Unmodified rhG-CSF derivative | — | 100 | 100 |
| 5CHTO(2UU)-rhG-CSF derivative | 20 | 100 | 100 |
| 5CHTC(2AA)-rhG-CSF derivative | 21 | 100 | 100 |
| 5CHTO(2EA)-rhG-CSF derivative | 22 | 100 | 100 |
| 5CHTM(2EA)-rhG-CSF derivative | 23 | 100 | 100 |

TABLE 7

NFS60 cell growth-accelerating activity
of chemically modified rhG-CSF

| Compound Abbreviation | Example | Concentration (ng/ml) | Relative activity (%) |
|---|---|---|---|
| Unmodified rhG-CSF | — | 100 | 100 |
| 5CHTM(2EA)-rhG-CSF | 25 | 100 | 100 |
| 5CHTC(2AA)-rhG-CSF | 26 | 100 | 100 |

TEST EXAMPLE 4

Enzyme Activity of Chemically Modified Superoxide Dismutase

The enzyme activities of chemically modified superoxide dismutases prepared in Example 27, Examples 30 to 32 and Example 34 were measured by the xanthine-xanthin oxydase-cytochrome C system of Mccord, J. M. and Fridovichi, I. [*J. Biol. Chem.*, 244: 6049 (1969)]. One unit (U) of SOD activity is an enzyme amount of SOD which inhibits a reducing rate of cytochrome C at an extent of 50%, and was calculated according to the following equation:

$$\text{Specific activity } (U/\text{mg}) = \left(\frac{\text{blank}}{\Delta A/\min} - 1\right) \times \frac{1}{0.000256}$$

Tables 8 and 9 show the enzyme activity of chemically modified bovine SOD and chemically modified human SOD, respectively.

SOD 50 U/mg=0.000256 mg (at 3900 U/mg)

ΔA/minute: Test result

TABLE 8

Enzyme activity of chemically modified
bovine Cu/Zn superoxide dismutase

| Compound abbreviation | Example | Relative activity (%) |
|---|---|---|
| Unmodified bSOD | — | 100 |
| 5CHTC(2AA)-bSOD | 27 | 72 |
| 5CHTM(2EA)-bSOD | 30 | 90 |
| 5CHTM(2EA)-bSOD (purified one) | 31 | 114 |

*The activity was designated by relative activity when the enzyme activity of unmodified bovine SOD was defined as 100%.

TABLE 9

Enzyme activity of chemically modified
human Cu/Zn superoxide dismutase

| Compound abbreviation | Example | Relative activity (%) |
|---|---|---|
| Unmodified hSOD | — | 100 |
| 5CHTM(2EA)-hSOD | 32 | 101 |
| 5CHTM(2UM)-hSOD | 34 | 92 |

*The activity was designated by relative activity when the enzyme activity of unmodified human SOD was defined as 100%.

TEST EXAMPLE 5

Effect for Prolonging Serum Half-life of Chemically Modified Interferon-β

Each of 5CHTO(2UU)-rhIFN-β obtained in Example 11, 5CHTC(2AA)-rhIFN-β obtained in Example 12, 5CHTM(2EA)-rhIFN-β obtained in Example 14, 10SCM-rhIFN-β obtained in Reference Example 2 and unmodified rhIFN-β obtained in Reference Example 6 was prepared with an isotonic phosphate buffer at a concentration of 12.5 μg/ml, and 200 μl of each of the resulting solution was injected intravenously into 8 to 10 week-old BALB/c male mice (Japan Charles liver). The mice were killed with time, the serum was collected, and the concentration of IFN-β in the blood was calculated by ELISA (Enzyme-linked Immunosorbent Assay).

The results are shown in FIG. 1.

The unmodified IFN-β decreased to the detection limit or less 1 hour after the administration but, in chemically modified IFN-β, the concentration in the blood was maintained even after several hours and thus a remarkable durability was provided.

Moreover, it was found that the compounds in the present invention, i.e., the rhIFN-β modified with a branched polyethylene glycol having a molecular weight of about 10,000 was more excellent in durability in the blood than the rhIFN-β modified with a linear polyethylene glycol having a molecular weight of about 10,000.

TEST EXAMPLE 6

Effect for Prolonging Serum Half-life of Chemically Modified rhG-CSF

Each of the chemically modified compounds obtained in Examples 23 and 25, and Reference Example 3 and unmodified compound obtained in Reference Examples 5 and 9 was injected intravenously into male mice at a dose of 0.1 mg/kg, the blood was collected from caudal vein after 24 hours and suitably diluted, and then the concentration of each compound in the blood was measured by ELISA. Table 10 shows the average value of two experiments.

TABLE 10

Serum half-life extending effect
of chemically modified rhG-CSF

| Compound name | Example | Concentration in blood after 24 hours (ng/mL) |
|---|---|---|
| 5CHTM(2EA)-rhG-CSF derivative | 23 | 105 |
| 5CHTM(2EA)-rhG-CSF | 25 | 269 |
| 10SCM-rhG-CSF derivative | Reference Example 3 | 72 |
| rhG-CSF derivative | Reference Example 5 | Lower than detection limit |
| rhG-CSF | Reference Example 9 | Lower than detection limit |

The unmodified compound decreased to the detection limit or less after 24 hours but, in the chemically modified rhG-CSF and the chemically modified rhG-CSF derivative, the concentration in the blood was maintained and thus a remarkable durability in the blood was provided.

Moreover, it was found that the compounds in the present invention, i.e., the rhG-CSF and rhG-CSF derivative modified with a branched polyethylene glycol having a molecular weight of about 10,000 were more excellent in durability in the blood than the rhG-CSF derivative modified with a linear polyethylene glycol having a molecular weight of about 10,000.

TEST EXAMPLE 7

Comparison of Molecular Size by Electrophoresis of Chemically Modified rhIFN-β

SDS-PAGE of each of the branched polyethylene glycol-modified rhIFN-β obtained in Examples 11 and 14 and the linear polyethylene glycol-modified rhIFN-β obtained in Reference Example 2 was carried out and the apparent molecular weight of each component was calculated from molecular weight markers using the resulting dry gel.

TABLE 11

Apparent molecular weight of chemically modified rhIFN-β calculated on SDS-PAGE

| Abbreviation of modifying reagent<br>Referred Example | 5CHTO(2UU)<br>11 | 5CHTM(2EA)<br>14 | 10SCM<br>Reference Example 2 |
|---|---|---|---|
| Molecular weight of 1 molecule-bound component* | 40.8 kDa | 44.6 kDa | 36.6 kDa |
| Molecular weight of 2 molecule-bound component* | 66.5 kDa | 75.6 kDa | 64.5 kDa |

*Apparent molecular weight calculated from calibration curve of molecular markers using a PDI scanner (Model SM3 manufactured by Howtek, Inc.). As molecular weight standards for calibration curve, lysozyme (14,400), trypsin inhibitor (21,500), carbonic anhydrase (31,000), ovalbumin (45,000), serum albumin (66,200) and phosphorypase b (97,400) were used.

As compared with the linear polyethylene glycol-modified compound, the branched polyethylene glycol-modified compounds have almost the same molecular weight but the apparent molecular weight on electrophoresis increased, so that it was found that the molecular size was larger.

TEST EXAMPLE 8

Comparison of Molecular Size by Electrophoresis of Chemically Modified rhG-CSF Derivatives SDS-PAGE of each of the double-chain branched polyethylene glycol-modified rhG-CSF derivatives obtained in Examples 21 and 23 and the linear polyethylene glycol-modified rhG-CSF derivative obtained in Reference Example 3 was carried out and the apparent molecular weight of each component was calculated from molecular weight markers using the resulting dry gel. Table 12 shows one example of the apparent molecular weight obtained by electrophoresis of each chemically modified rhG-CSF derivative.

TABLE 12

Apparent molecular weight of chemically modified rhG-CSF calculated on SDS-PAGE

| Abbreviation of modifying reagent<br>Referred Example | 5CHTC(2AA)<br>21 | 5CHTM(2EA)<br>23 | 10SCM<br>Reference Example 3 |
|---|---|---|---|
| Molecular weight of 1 molecule-bound component* | 45.1 kDa | 48.0 kDa | 33.3 kDa |
| Molecular weight of 2 molecule-bound component* | 76.1 kDa | 80.1 kDa | 60.4 kDa |

*Apparent molecular weight calculated from calibration curve of molecular markers using a PDI scanner (Model SM3 manufactured by Howtek, Inc.). As molecular weight standards for calibration curve, lysozyme (14,400), trypsin inhibitor (21,500), carbonic anhydrase (31,000), ovalbumin (45,000), serum albumin (66,200) and phosphorypase b (97,400) were used.

As compared with the linear polyethylene glycol-modified compound, the branched polyethylene glycol-modified compounds have almost the same molecular weight but the apparent molecular weight on electrophoresis increased, so that it was found that the molecular size was larger.

TEST EXAMPLE 9

Comparison of Molecular Size by Electrophoresis of Chemically Modified SOD

SDS-PAGE of each of the double-chain branched polyethylene glycol-modified SOD obtained in Examples 27 and 30 and the linear polyethylene glycol-modified SOD obtained in Reference Example 4 was carried out and the apparent molecular weight of each component was calculated from molecular weight markers using the resulting dry gel. Table 13 shows one example of the apparent molecular weight obtained by electrophoresis of each chemically modified SOD.

TABLE 13

Apparent molecular weight of chemically modified SOD calculated on SDS-PAGE

| Abbreviation of modifying reagent | 5CHTC(2AA) | 5CHTM(2EA) | 10SCM Reference |
|---|---|---|---|
| Referred Example | 27 | 30 | Example 4 |
| Molecular weight of 1 molecule-bound component* | 41.4 kDa | 45.7 kDa | 36.3 kDa |
| Molecular weight of 2 molecule-bound component* | 66.7 kDa | 81.5 kDa | 62.1 kDa |

*Apparent molecular weight calculated from calibration curve of molecular markers using a PDI scanner (Model SM3 manufactured by Howtek, Inc.). As molecular weight standards for calibration curve, Lysozyme (14,400), trypsin inhibitor (21,500), carbonic anhydrase (31,000), ovalbumin (45,000), serum albumin (66,200) and phosphorypase b (97,400) were used.

As compared with the linear polyethylene glycol-modified compound, the branched polyethylene glycol-modified compounds have almost the same molecular weight but the apparent molecular weight on electrophoresis increased, so that it was found that the molecular size was larger.

TEST EXAMPLE 10

Comparison of Molecular Size With Conventional Double-chain Branched PEG Derivative by Light Scattering Measurement The comparison of molecular sizes of the double-chain branched polyethylene glycol derivative [5CHTM(2EA2)] obtained in Example 10 and the conventional double-chain branched polyethylene glycol derivative (5PEG$_2$GABA) obtained in Reference Example 8 in an aqueous solution was carried out by the measurement under the following conditions using a light scattering photometer.

<Measuring Conditions>
Light scattering photometer: DLS-7000 (Otsuka Denshi)
Differential refractometer: DRM-1021 (Otsuka Denshi)
Light source: argon laser 75 mW (632.8 nm)
Measuring temperature: 25° C.
Buffer solution: isotonic phosphate buffer
Sample concentration: 1.4 mg/ml to 3.3 mg/ml
Pre-treatment: filtration through a 0.22 μm filter As a result, it was suggested that the compound of Example 10 had an inertial square radius about 1.9 times larger than the compound of Reference Example 8. As compared with the conventional polyethylene glycol derivative branched through triazine ring having a plane structure, it was found that the polyethylene glycol chain linked to cyclohexane has longer volume in the aqueous solution, and thus the polyethylene glycol of the present invention have the same molecular weight but are excellent in a molecular weight increasing effect.

TEST EXAMPLE 11

Comparison of Conversion Into Chemically Modified Compound With Conventional Double-chain Branched Polyethylene Glycol Derivative As the double-chain branched polyethylene glycol derivative of the present invention, the compound obtained by converting the compound 5CHTM(2EA2) obtained in Example 10 into the NHS ester in a similar manner to Example 36 was used.

As a reference, the conventional polyethylene glycol derivative PEG2-NHS having a molecular weight of about 10,000 [lysine derivative, abbreviation: 5LYS(2UA), manufactured by Shearwater Polymers, Inc.]

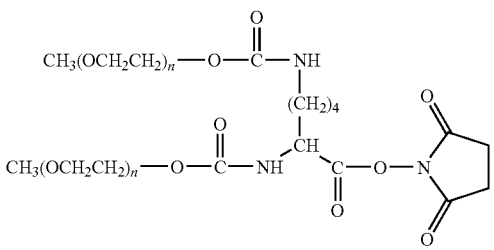

was used.

To 3.68 mg/ml of the rhG-CSF derivative obtained in Reference Example 5 prepared with a 50 mmol/L phosphate buffer (pH 7) was added the NHS ester in an amount of 1.6, 2.7, 3.8, 4.8, or 5.8 mg per mg of the protein, and the mixture was allowed to react at 4° C. The reaction liquid after 20 minutes was analyzed by gel filtration HPLC using TSK gel G-4000SW$_{XL}$ column in a similar manner to Example 11. The conversion into the chemically modified compound was calculated from the peak area of the resulting chromatogram.

Table 14 shows the results.

TABLE 14

Conversion (%) of G-CSF derivative into chemically modified compound

| Compound abbreviation | Produced amount of modified compound (%) Reagent amount (mg) per mg of protein | | | | |
|---|---|---|---|---|---|
| | 1.6 | 2.7 | 3.8 | 4.8 | 5.8 |
| 5CHTM(2EA2) | 34.0 | 48.6 | 56.1 | 55.6 | 63.8 |
| 5LYS(2UA) | 26.5 | 36.6 | 38.2 | 39.7 | 46.2 |

From Table 14, it was confirmed that, as compared with the conventional double-chain branched polyethylene glycol derivative, the double-chain branched polyalkylene glycol of the present invention could realize increased conversion of the protein into the chemically modified compound under neutral conditions in which the protein was more stable.

TEST EXAMPLE 12

Comparison of Stability in an Aqueous Solution With Conventional Double-chain Branched Polyethylene Glycol Derivative The double-chain branched polyethylene glycol derivative [5CHTM(2EA2)] of the present invention obtained in Example 10 was used. As a reference, a terminal carboxylic acid type of the conventional polyethylene glycol derivative PEG2-NHS [lysine derivative, abbreviation: 5LYS(2UA), manufactured by Shearwater Polymers, Inc.] was used.

The stability of both compounds was evaluated according to the following manner.

Both reagents were prepared to be 2 mg/ml using neutral (50 mmol/L phosphate buffer, pH 7.5) and alkaline (50 mmol/L borate buffer, pH 10.0) buffers, and the resulting aqueous solutions were left at 37° C. The solutions were sampled immediately after the preparation and periodically, and after the neutralization with 1 mol/L phosphate buffer (pH 7.5), the bands (10 kDa) and decomposed products of both the reagents were compared on electrophoresis.

As a result, it was confirmed that 5LYS(2UA) was stable at neutral but the band (5 kDa) of single-chain was detected under alkaline conditions and the band became clear with time. On the other hand, in 5CHTM(2EA2), no decomposed product was detected for 1 month in both of the sample under neutral conditions and the sample under alkaline conditions.

The above result indicated that the decomposition from double-chain one to single-chain one may occur under alkaline conditions in the conventional double-chain branched PEG reagent 5LYS(2UA). In general, the modification of a protein with a polyethylene glycol was frequently carried out under alkaline conditions of pH 8 to 11, and thus, it was suggested that the modifying agent is possibly decomposed in the chemical modification reaction when 5LYS(2UA) was used.

<Electrophoresis Conditions>
Gel: NuPAGE 4-12% (manufactured by NOVEX)
Staining: aqueous solution of 0.1 mol/L iodine
Molecular weight marker: PEG5000, PEG10000, PEG20000 (manufactured by Nippon Oil & Fats Co., Ltd.)

TEST EXAMPLE 13

Binding Activity of Chemically Modified Anti-GD3 Chimera Antibody Against Ganglioside GD3

The binding activity of the chemically modified KM-871 prepared in Example 39 was measured based on the method of Kenya. S et al. [*Cancer Immunol. Immunother.*, 36: 373-380 (1993)].

As a result, when the binding activity of unmodified KM-871 against ganglioside GD3 was defined to be 100%, it was confirmed that about 20% of the binding activity toward ganglioside GD3 remained in the chemically modified KM-871.

TEST EXAMPLE 14

Comparison of Conversion into Chemically Modified Polypeptide With Conventional Double-chain Branched Polyethylene Glycol Derivative As the double-chain branched polyethylene glycol derivative of the present invention, the compound obtained by converting the compound 5CHTM(2EA2) obtained in Example 10 into the NHS ester in a similar manner to Example 36 was used.

As a reference, the conventional polyethylene glycol derivative PEG2-NHS (manufactured by Shearwater Polymers, Inc.) having a molecular weight of about 10,000 was used.

To 2.0 mg/ml of bovine Cu/Zn superoxide dismutase and bovine serum albumin (BSA) prepared with a 50 mmol/L phosphate buffer (pH 6), the above NHS ester of the polyethylene glycol derivative was added in an amount of 50 mol per mol of the protein, and the mixture was reacted at 4° C. for 15 hours. Thereafter, the reaction liquid was analyzed by gel filtration HPLC using TSK gel G-4000SW$_{XL}$ column in a similar manner to Example 11. The conversion into the chemically modified compound was calculated from the peak area of the resulting chromatogram.

Table 15 shows the results.

TABLE 15

Conversion (%) of bSOD and BSA into chemically modified compound

| Compound abbreviation | Produced amount of chemically modified compound (%) | |
|---|---|---|
| | bSOD | BSA |
| 5CHTM(2EA2) | 71.2 | 34.5 |
| 5LYS(2UA) | 29.7 | 10.7 |

From Table 15, it was confirmed that, as compared with the conventional double-chain branched polyethylene glycol derivative, the double-chain branched polyalkylene glycol of the present invention could realize increased conversion of the protein into the chemically modified compound under neutral conditions in which the protein was more stable.

TEST EXAMPLE 15

Comparison of the Activities of Chemically Modified Interferon-β and Unmodified Interferon-β in Guinea Pig EAE Model As an animal model of multiple scleroses, experimental autoimmune encephalomyelitis (thereafter, abbreviated as "EAE") has been widely used [*Journal of Neuropathology & Experimental Neurology*, 57: 602-614 (1998)]. In this model, by the sensitization with proteins of whole spinal cord components or myelin constituting components together with an adjuvant, an animal shows acute or recurrent paralysis and also shows the infiltration of T cell of central nervous system and the demyelination lesion as are observed in multiple scleroses. Moreover, from the results of cell transfusion and the like, it becomes apparent that CD4$^+$T cell which specifically reacts with central nerve myelin-constituting proteins plays an important role [*Clinical Neuroscience*, 15: 23-27 (1997)]. Furthermore, it has been reported that human IFN-β is effective in EAE of guinea pig (*72nd Japan Pharmacological Society, Annual Meeting Program*, 292P, P-684, 1999), and thus, guinea pig EAE model has been considered to be useful as a medicinal effect-evaluating system for human IFN-β.

<Used Animal>

Hartley guinea pigs (female, SPF, 3 week-old, Japan SLC, Inasa growing farm, Hamamatsu-city) was purchased and used after rearing them in an animal room under the conditions of a constant temperature (22±3° C.) and a constant humidity (50±20%) for 1 week.

<Preparation of Emulsion> a) Preparation of Fresh Guinea Pig Central Nervous System (CNS) Homogenate

CNS of guinea pig was recovered under Nembutal anesthesia and a physiological saline (manufactured by Otsuka Pharmaceutical, Tokyo) was added thereto in an amount of 1 mL per g of CNS wet weight. The solution was homogenized for 90 seconds using polytron (KINEMATICA, Switzerland) to form a CNS concentrate solution. The solution was diluted four times with physiological saline and the dilute was used.

b) Mycobacterium Tuberculosis H37Ra (Hereinafter Referred to as "H37Ra")

H37Ra (Difco, Detroit, Mich., U.S.A.) was pulverized in an agate mortar and then suspended into Incomplete Freund adjuvant (IFA, Difco, Mich., U.S.A.) to give a concentration of 2.5 mg/mL. Equal amounts of a) and b) were mixed and formed to be a complete emulsion using polytron.

<Drugs and Preparation Method>

Agents used and dose thereof are shown below.
Human IFN-β (IFN-β): 2.4 million international units (MIU)/kg
PEG-modified human IFN-β (PEG-IFN-β): 2.4 MIU/kg PEG-IFN-β was produced using IFN-β in accordance with the method of the following Example 14. The dose of IFN-β or PEG-IFN-β was determined with reference to the report of Yabuuchi et al. (*72nd Japan Pharmacological Society, Annual Meeting Program*, 292P, P-684, 1999). IFN-β and PEG-IFN-β were used in the form of solutions having concentrations of 95.5 MIU/mL and 109.04 MIU/mL, respectively, each dissolved in 60% ethylene glycol (Kanto Chemical Co., Inc., Tokyo), 50 mmol/L phosphate buffer (pH 6) ($KH_2PO_4$, $Na_2HPO_4 1.2H_2O$, manufactured by Wako Pure Chemical Industries, Ltd., Osaka), and 1 mol/L sodium chloride (manufactured by Wako Pure Chemical Industries, Ltd.) solution. Each drug was diluted immediately before use so that the activity was 2.4 MIU/mL in PBS (Dulbecco's phosphate buffered saline without magnesium and calcium (ICN Biomedicals, Calif., U.S.A.) and the amount of the solvent contained was equal.

<Administration Method>

Each drug was administered subcutaneously to the back of guinea pig once per day from day 0 until day 20.

<Grouping and Sensitization>

The body weights of guinea pigs were measured and the animals were grouped so that the average body weight of each group was almost equal. Then, 200 mL of each of the above emulsion was administered subcutaneously at 3 places (600 mL/body) of the neck of each guinea pig under ether anesthesia (neither sensitization nor drug administration was carried out in Normal group). Groups 1 to 4 are shown below.
Group 1 (normal group): "no sensitization and no drug administration"
Group 2 (vehicle control group): "sensitization was carried out and a solution of 60% ethylene glycol, 50 mmol/L phosphate buffer (pH 6), and 1 mol/L sodium chloride solution diluted with PBS was administered"
Group 3 (IFN-β administered group): "sensitization was carried out and IFN-β (2.4 MIU/kg) was administered"
Group 4 (PEG-IFN-β administered group): "sensitization was carried out and PEG-IFN-β (2.4 MIU/kg) was administered"

Scoring on external symptoms was carried out every three days from day 0 until day 6 and every day from day 8 until day 22 according to the following standard, the day when sensitized being day 0.

The scoring standard is as follows:
0: no abnormality
1: abnormality of standing reflex
2: semiparalysis of hindlimbs
3: complete paralysis of hindlimbs
4: paralysis of forelimbs, near-death
5: death <Statistical Analysis>

The analysis was carried out using a statistical analysis software, SAS (Release 6.12, SAS Inc, Carry, N.C., USA). The significant difference was tested according to Wilcoxon rank sum test on each day.

<Results>

FIG. 2 shows the time course of the change in clinical scores (external symptoms) of Groups 1 to 4 in the guinea pig EAE model.

In the guinea pig EAE model, all the guinea pigs showed the symptoms until day 9 to day 13 and were died on 21st day after the sensitization in Group 2 (vehicle control group) wherein only the solvent was administered after CNS sensitization. The change of clinical scores in Group 3 (IFN-β administered group) was almost the same as that in Group 2 (vehicle control group), and no apparent effect was observed. On the other hand, in Group 4 (PEG-IFN-β administered group), all the guinea pigs showed the symptoms but a significant suppress of clinical scores on day 21 and day 22 was observed as compared with Group 3 (vehicle control group).

As described above, it was suggested that the IFN-β chemically modified with PEG was more effective in multiple scleroses than unmodified IFN-β.

Moreover, interferons are known to be useful for diseases such as viral diseases including hepatitis, malignant tumors and the like, and therefore, IFN-β chemically modified with PEG or the like is considered to be useful for diseases such as viral diseases (hepatitis etc.), malignant tumors and the like.

BRIEF DESCRIPTION OF THE DRAWINGS

In FIG. 1, symbols (-♦-, -■-, -▲-, -○-, -□-) have the following meanings:

-♦-: changes of the concentration in the blood when unmodified rhIFN-β was intravenously injected to mice;

-■-: changes of the concentration in the blood when 5CHTO(2UU)-rhIFN-β was intravenously injected to mice;

-▲-: changes of the concentration in the blood when 5CHTM(2EA)—rhIFN-β was intravenously injected to mice;

-○-: changes of the concentration in the blood when 5CHTC(2AA)—rhIFN-β was intravenously injected to mice; and -□-: changes of the concentration in the blood when 10SCM-rhIFN-β was intravenously injected to mice.

Figure 1:
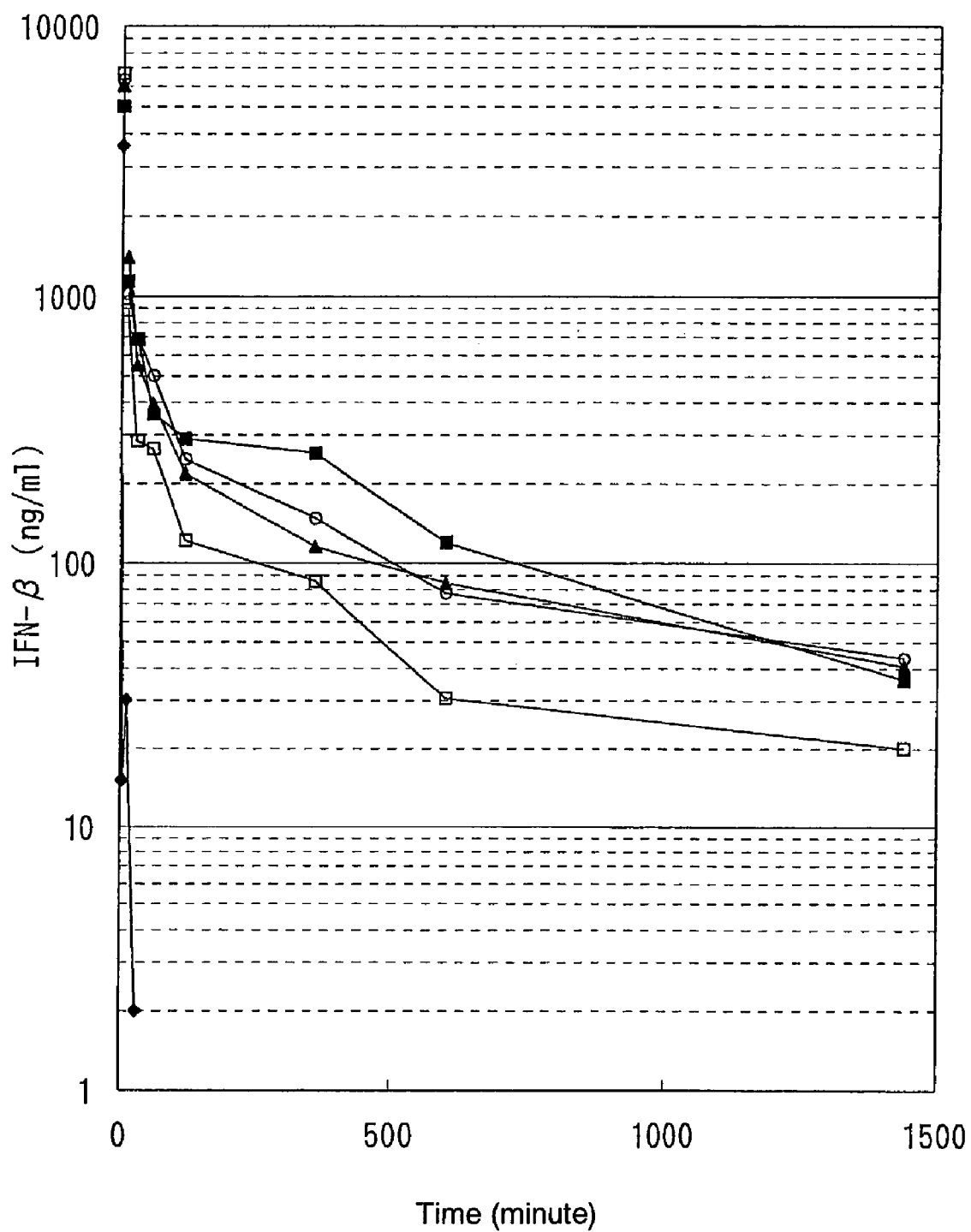
FIG. 1 illustrates changes of the concentration in the blood of each interferon-β when chemically modified interferon-β and unmodified interferon-β were administered.
Figure 2:
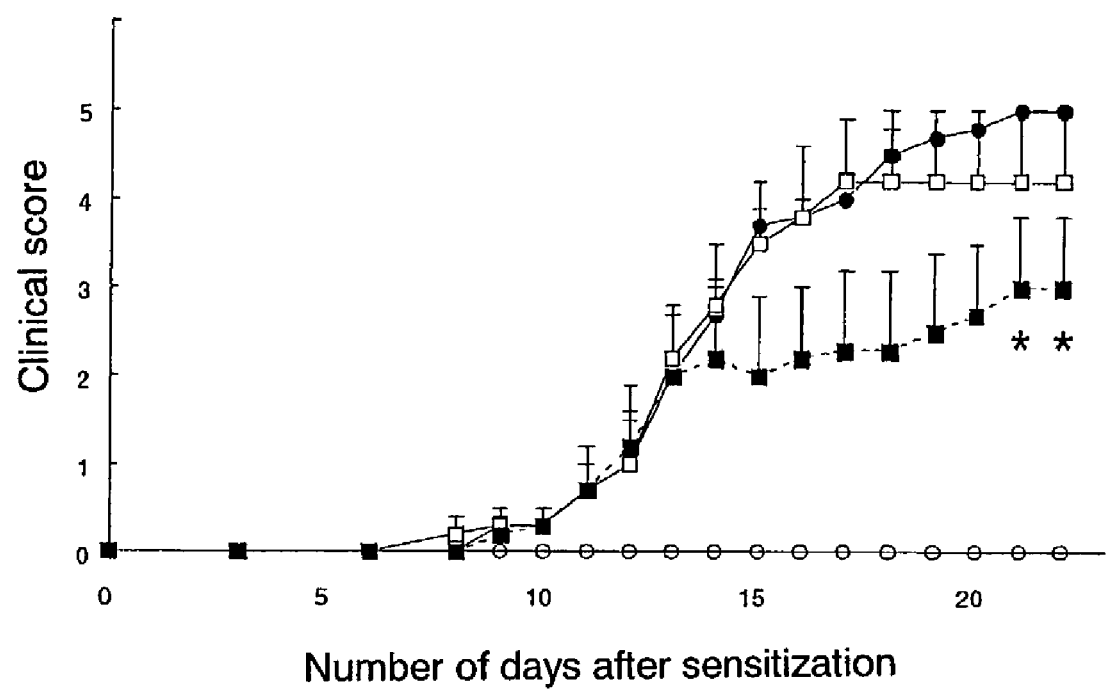

FIG. 2 illustrates changes of clinical scores in Group 1 (normal group), Group 2 (vehicle control group), Group 3 (IFN-β administered group), and Group 4 (PEG-IFN-β administered group) in guinea pig EAE model. In FIG. 2, symbols (-○-, -●-, -□-, -■-) have the following meanings. Moreover, each value means average value±standard error (SE) and * means p<0.05 (in comparison with vehicle group).

-○-: Group 1 (normal group)
-●-: Group 2 (vehicle control group)
-□-: Group 3 (IFN-β administered group)
-■-: Group 4 (PEG-IFN-β administered group)

BEST MODE FOR CARRYING OUT THE INVENTION

The present invention are based on the following Examples in detail, but the scope of the present invention is not limited thereto. The abbreviations in Examples means as follows unless otherwise stated. Also, abbreviations of amino acids and protective groups thereof used herein were used in accordance with the advice of IUPAC-IUB Commission on Biochemical Nomenclature [*Eur. J. Biochem.*, 138: 9 (1984)].

| | |
|---|---|
| ELISA: | enzyme-linked immunosorbent assay |
| SDS-PAGE: | sodium dodecyl sulfate-poly acrylamide gel electrophoresis |
| PEG: | polyethylene glycol |
| mPEG: | monomethoxy polyethylene glycol |
| IFN: | interferon |
| hIFN: | human interferon |
| rhIFN: | recombinant human interferon |
| G-CSF: | granulocyte-colony stimulating factor |
| rhG-CSF: | recombinant human granulocyte-colony stimulating factor |
| SOD: | superoxide dismutase |
| bSOD: | bovine superoxide dismutase |
| hSOD: | human superoxide dismutase |
| DSC: | N,N'-disuccinimidyl carbonate |
| TEA: | triethylamine |
| DMF: | N,N'-dimethylformamide |
| DMSO: | dimethyl sulfoxide |
| NHS: | N-hydroxysuccinimide |
| Ts: | p-toluenesulfonyl |
| TsCl: | p-toluenesulfonyl chloride |
| DMAP: | dimethylaminopyridine |
| PyBOP: | benzotriazol-1-yloxytripyrrolidinophosphonium hexafluorophosphate |
| HOBt: | N-hydroxybenzotriazole |
| DCC: | N,N'-dicyclohexylcarbodiimide |
| LAH: | lithium aluminum hydride |
| NMM: | N-methylmorpholine |
| TFA: | trifluoroacetic acid |

EXAMPLE 1

Synthesis of 5 kDa Double-chain Branched Plyethylene Glycol-Cyclohexane Derivative Abbreviation: 5CHTO(2UU) (Compound No. 1)

In 20 ml of acetonitrile, 420.5 mg (2.5 mmol) of cis,cis-1,3,5-cyclohexanetriol dihydrate (manufactured by Fluka) and 3.2 g (12.5 mmol) of DSC were dissolved in an argon stream, and 2.1 ml (12.5 mmol) of TEA was added thereto, followed by stirring at room temperature for overnight. The solvent was removed under reduced pressure, chloroform and 0.1 mol/L hydrochloric acid were added thereto, and the mixture was extracted. The chloroform layer was dried over anhydrous sodium sulfate and then the solvent was removed under reduced pressure to obtain 357 mg (0.64 mmol) of cis,cis-1,3,5-tris(succinimidyloxycarbonyloxy)cyclohexane (yield:: 25.7%).

Then, 500 mg (0.1 mmol) of monomethoxy polyethylene glycol propylamine (mPEG-NH$_2$) (average molecular weight:: 5,000, manufactured by Nippon Oil & Fats Co., Ltd.) and the trisuccinimidyl carbonate derivative of cyclohexanetriol synthesized in the above were dissolved in 12.5 ml of methylene chloride, and 28 µl of TEA was added thereto, followed by stirring at room temperature for 2 hours. Thereafter, the reaction liquid was added dropwise to diethyl ether and a formed white precipitate was dried under reduced pressure to obtain 472 mg of the residue (yield: 94.4%). From the residue, 372 mg was purified by reversed phase HPLC. TSK gel ODS120-T (30 mm×250 mm) (Tosoh Corporation) was used as a column, an aqueous solution of 0.1% TFA was used as a mobile phase at a flow rate of 10 ml/minute, and elution was carried out by a linear concentration gradient of 0 to 90% acetonitrile. An objective fraction (30 ml) having an average molecular weight of 10,000 was collected, acetonitrile was removed under reduced pressure, and the mixture was extracted with chloroform. The extract was added dropwise to diethyl ether and a white precipitate was collected by filtration and dried under reduced pressure to obtain 121.7 mg of the objective product (recovery 32.7%).

<Gel Filtration HPLC Analysis>

Mobile phase: 150 mmol/ml sodium chloride, 20 mmol/L sodium acetate buffer (pH 4.5)

Flow rate: 0.7 ml/minute

Detection: RI

Separating column: TSK gel G-2000SW$_{XL}$ (7.8 mm×300 mm) (Tosoh Corporation)

Column temperature: room temperature

Retention time: 12.2 minutes

<$^1$H-NMR analysis (CDCl$_3$, 300 MHz)>;

δ (ppm): 3.61 (s, 8 nH), 3.41 (s, 6H), 4.69 (br, 4H), 1.77 (brm, 4H), 5.30 (br, 2H), 0.8-3.4 (m, 9H), 2.84 (s, 4H).

EXAMPLE 2

Synthesis of 5 kDa Double-chain Branched Polyethylene Glycol-cyclohexane Derivative Abbreviation: 5CHTC(2AA) (Compound No. 2)

In 50 ml of DMF, 84.0 mg (0.388 mmol) of cis,cis-1,3,5-cyclohexanetricarboxylic acid (manufactured by Fluka) was dissolved, and 270.2 mg (2.0 mmol) of HOBt and 1.04 g (2.0 mmol) of PyBOP were added thereto, followed by stirring at 0° C. for 30 minutes. Then, 5 g (1.0 mmol) of monomethoxy polyethylene glycol propylamine (average molecular weight:: 5,000, manufactured by Nippon Oil & Fats Co., Ltd.)

and 219.7 μl (1.9 mmol) of NMM were successively added thereto, followed by stirring for overnight. The mixture was adjusted with 1 mol/L hydrochloric acid to pH 1 to 2 and extracted with chloroform. The organic layer was dried over anhydrous sodium sulfate, and then added dropwise to diethyl ether. The resulting white precipitate was collected to obtain 3.78 g (yield: 75.6%) of a crude product containing the objective compound. Then, the product was purified using 300 mg of DEAE-Sepharose F.F. column (Amersham-Pharmacia Biotech). The crude product dissolved in water was added to the column, and the column was further washed with 600 ml of water and eluted with a 0.6 to 1.2 mmol/L aqueous sodium chloride solution. Thereafter, an objective product fraction was extracted with chloroform and the solvent was removed under reduced pressure to obtain 610.4 mg (yield: 65.2%) of the objective product.

<Gel Filtration HPLC Analysis>

Using TSK gel G-2000SW$_{XL}$ column, the product was analyzed in a similar manner to Example 1.

Retention time: 12.0 minutes

<$^1$H-NMR analysis (CDCl$_3$, 300 MHz)>;

δ (ppm): 1.56 (m, 3H), 2.1-2.5 (m, 6H), 1.77 (m, 4H), 2.1-2.3 (br, 4H), 3.38 (br, 4H), 3.64 (s, 8 nH), 3.36 (s, 6H), 6.46 (t, J=5.23 Hz, 2H).

EXAMPLE 3

Synthesis of 5 kDa Double-chain Branched Polyethylene Glycol-cyclohexane Derivative Abbreviation: 5CHTO(2EA) (Compound No. 3)

In 150 ml of toluene, 50 g (10 mmol) of MPEG (average molecular weight:: 5,000, manufactured by Nippon Oil & Fats Co., Ltd.) was dissolved, followed by refluxing for dehydration. Thereto, 3.5 ml (25 mmol) of TEA was added dropwise, and a thionyl bromide/toluene solution (1.55 ml of thionyl bromide was dissolved in 13.6 ml of toluene) was added over 1 hour. After refluxing for 1 hour, the mixture was filtered using celite, and left at room temperature for 4 hours. Then, it was heated to 50° C. and 5 g of active carbon was added. The active carbon was removed using celite and the filtrate was left at 4° C. for overnight. Next day, the supernatant was removed and then the residue was dissolved in 250 ml of ethanol warmed to 60° C. Thereto, 3 g of active carbon was added, the mixture was filtered using celite, and left at room temperature for 4 hours. Next day, the residue was washed with cold ethanol and diethyl ether and dried to obtain 32.87 g (yield: 65.74%) of brominated mPEG (mPEG-Br).

<$^1$H-NMR analysis (CDCl$_3$, 300 MHz)>;

δ (ppm): 3.64 (s, 4 nH), 3.38 (s, 3H), 3.48 (t, J=6.3 Hz, 2H), 3.81 (t, J=6.3 Hz, 2H).

Next, 1.322 g (10 mmol) of cis,cis-1,3,5-cyclohexanetriol dihydrate was thoroughly dried and then dissolved in 25 ml of anhydrous DMF. In an argon stream, the solution was added dropwise to 0.48 g (11 mmol) of sodium hydride, followed by stirring for 30 minutes. Thereto, 10 g (2 mmol) of the above PEG-Br dissolved in 25 ml of DMF was added dropwise, followed by stirring at room temperature for overnight. Thereafter, the reaction liquid was added dropwise to diethyl ether and a precipitate was dried under reduced pressure. Then, the dried powder was dissolved in an appropriate amount of water and the pH was adjusted to 3 with 1 mol/L hydrochloric acid. The solution was extracted with chloroform, the organic layer was dried over anhydrous sodium sulfate, and then the solvent was removed under reduced pressure. The residue was dissolved in a small amount of methylene chloride, the solution was added dropwise to diethyl ether, and the resulting precipitate was dried under reduced pressure to obtain 7.5 g (yield: 75.0%) of a single-chain crude product wherein one molecule of mPEG was linked to cyclohexanetriol.

To 5 g of the crude product, 50 ml of toluene was added, followed by refluxing for dehydration for overnight. Also, 5.5 g (1.1 mmol) of mPEG-Br was dissolved in 50 ml of toluene, followed by refluxing for dehydration at 160° C. for overnight. Then, 144 mg (3.3 mmol) of sodium hydride was added to a toluene solution of the above crude product, followed by stirring for 30 minutes, and a toluene solution of mPEG-Br was added dropwise thereto. After refluxing for dehydration for overnight, an insoluble matter was removed by filtration, followed by drying under reduced pressure. The pH was adjusted to 1 to 2 with 1 mol/L hydrochloric acid, and the mixture was extracted with chloroform. The organic layer was dried over anhydrous sodium sulfate and then the solvent was removed under reduced pressure. The residue was dissolved in a small amount of methylene chloride and then the solution was added dropwise to diethyl ether. The resulting white precipitate was dried under reduced pressure to obtain 7.73 g (yield: 73.6%) of a crude product containing the objective compound.

In an aqueous solution of 8% potassium hydroxide, 1.5 g of the crude product was dissolved and 150 mg (2.11 mmol) of acrylamide was added thereto, followed by stirring at room temperature for 7 hours. Furthermore, 150 mg (2.11 mmol) of acrylamide was added thereto, followed by stirring at room temperature for 4 days. The reaction liquid was adjusted to pH 3 with 1 mol/L hydrochloric acid and extracted with chloroform, and the organic layer was dried over anhydrous sodium sulfate, followed by removal of the solvent under reduced pressure. The residue was dissolved in methylene chloride, and then the solution was added dropwise to diethyl ether. The resulting precipitate was filtered and dried under reduced pressure to obtain 1.017 g (67.8%) of a crude objective product.

The product was loaded to 60 ml of DEAE-Sepharose F.F. column (Amersham-Pharmacia Biotech), and then elution was carried out with a 0.4 to 1.4 mmol/L aqueous sodium chloride solution. A fraction containing the objective product was extracted with chloroform. The chloroform layer was dried over anhydrous sodium sulfate and then the solvent was removed under reduced pressure to obtain 52 mg of the objective product.

<Gel Filtration HPLC Analysis>

Using TSK gel G–2000SW$_{XL}$ column, the product was analyzed under conditions similar to Example 1.

Retention time: 12.7 minutes

<$^1$H-NMR analysis (CDCl$_3$, 300 MHz)>;

δ (ppm): 2.59 (t, J=16.0 Hz, 2H), 0.8-3.4 (m, 9H), 3.64 (s, 8 nH), 3.38 (s, 6H).

EXAMPLE 4

Synthesis of 5 kDa Double-chain Branched Polyethylene glycol-cyclohexane Derivative Abbreviation: 5CHTM(2EA) (Compound No. 4)

In a mixed solvent of 1 L of toluene and 500 ml of methylene chloride, 400 g (80 mmol) of mPEG (average molecular weight:: 5,000, manufactured by Nippon Oil & Fats Co., Ltd.) was dissolved. Thereto, 50 g of TsCl and 46.4 ml of TEA were added successively, followed by stirring at room temperature for 8 hours. Then, 50 g of TsCl was added thereto, followed by stirring for 16 hours. An insoluble matter was filtered off and the filtrate was concentrated under reduced pressure. The resulting residue was dissolved in a small amount of chloroform and the solution was added dropwise into diethyl ether. The resulting white precipitate was collected and dried under reduced pressure to obtain 344 g of tosyl-esterified mPEG (mPEG-OTs) (Yield 86.0%).

<$^1$H-NMR analysis (CDCl$_3$, 300 MHz)>;

δ (ppm): 2.45 (s, 3H), 3.38 (s, 3H), 3.70 (s, 4 nH), 4.16 (t, J=5.0 Hz, 2H), 7.34 (d, J=6.8 Hz, 2H), 7.80 (d, J=8.1 Hz, 2H).

In 1 L of DMF, 344 g of mPEG-OTs was dissolved and 54 g of sodium iodide was added thereto, followed by stirring at 80 to 90° C. for 1 hour. An insoluble matter was filtered off and the filtrate was added dropwise into diethyl ether. The resulting white precipitate was collected by filtration and dried under reduced pressure. The residue was dissolved in 1.5 L of an aqueous solution of 10% sodium thiosulfate, followed by stirring for a while, and the mixture was extracted with chloroform. The solvent was removed under reduced pressure to obtain 314 g of iodinated mPEG (mPEG-I) (yield: 78.5%).

<$^1$H-NMR analysis (CDCl$_3$, 300 MHz)>;

δ (ppm): 3.27 (t, J=6.9 Hz, 2H), 3.38 (s, 3H), 3.67 (s, 4 nH).

In 1 L of 1-propanol and 20 ml of concentrated sulfuric acid, 40 g of cis,cis-1,3,5-cyclohexanetricarboxylic acid (manufactured by Fluka) was dissolved, followed by stirring for 72 hours at room temperature. Then, an appropriate amount of ethyl acetate was added to the reaction liquid, and the mixture was neutralized with an aqueous saturated sodium hydrogen carbonate solution. The reaction liquid was extracted with ethyl acetate and the organic layer was dried over anhydrous sodium sulfate. The solvent was removed under reduced pressure to obtain 72.4 g (quantitative yield) of cis,cis-1,3,5-cyclohexanetricarboxylic acid n-propyl ester.

<$^1$H-NMR analysis (CDCl$_3$, 300 MHz)>;

δ (ppm): 0.94 (t, J=6.4 Hz, 9H), 1.65 (m, 6H), 4.05 (t, J=6.6 Hz, 6H), 1.56, 2.25, 2.40 (each m, total 9H).

In 50 ml of diethyl ether, 1.19 g of LAH was dissolved and 12.5 ml of a diethyl ether solution containing 3.2 g of cis,cis-1,3,5-cyclohexanetricarboxylic acid n-propyl ester was added thereto under an argon atmosphere, followed by further refluxing under stirring for 41 hours. Then, 2.5 ml of water was added thereto, followed by stirring for 15 minutes. Furthermore, 5 ml of ethanol was added dropwise, followed by stirring at room temperature for 3 hours. The reaction liquid was filtered and an insoluble matter was extracted with boiling ethanol. The ethanol solution was combined with the previous filtrate and the solvent was removed under reduced pressure. The resulting residue was extracted with boiling 1,4-dioxane and then the extract was dried over sodium sulfate. The solvent was removed under reduced pressure to obtain 1.50 g (yield: 91.7%) of cis,cis-1,3,5-cyclohexane trimethanol.

<Mass analysis (FAB-MS)>;

Found value: (M+H)$^+$ 175; Calculated value: C$_9$H$_{18}$O$_3$=174;

<H-NMR analysis (CDCl$_3$, 300 MHz)>;

δ (ppm): 3.21 (t, J=5.9 Hz, 6H), 4.35 (t, J=5.1 Hz, 3H), 0.43, 1.40, 1.75 (each m, total 9H).

In 10 ml of dry DMF, 2.5 g (14 mmol) of cis,cis-1,3,5-cyclohexane trimethanol was dissolved and the mixture was added dropwise to 2.28 g (46.2 mmol) of sodium hydride under an argon atmosphere, followed by stirring for 30 minutes. Thereto, 40 g (8 mmol) of mPEG-I dissolved in 50 ml of DMF was added dropwise, followed by stirring at room temperature for overnight. Thereafter, the reaction liquid was added dropwise to diethyl ether and the resulting precipitate was dried under reduced pressure. Then, the dried powder was dissolved in an appropriate amount of water and the pH was adjusted to 3 with 1 mol/L hydrochloric acid. The solution was extracted with chloroform, the organic layer was dried over anhydrous sodium sulfate, and then the solvent was removed under reduced pressure. The residue was dissolved in a small amount of methylene chloride, the solution was added dropwise to diethyl ether, and the resulting precipitate was dried under reduced pressure to obtain 33.0 g (83.0%) of a double-chain crude product wherein two molecules of MPEG were linked to cis,cis-1,3,5-cyclohexane trimethanol.

In an aqueous solution of 8% potassium hydroxide, 14.0 g of the crude product was dissolved and 1.18 g (16.7 mmol) of acrylamide was added thereto, followed by stirring at room temperature for 7 hours. Furthermore, 1.18 g (16.7 mmol) of acrylamide was added thereto, followed by stirring at room temperature for 4 days. The reaction liquid was adjusted to pH 3 with 1 mol/L hydrochloric acid and extracted with chloroform, the organic layer was dried over anhydrous sodium sulfate, and the solvent was removed under reduced pressure. The residue was dissolved in a small amount of methylene chloride, and then the solution was added dropwise to diethyl ether. The resulting precipitate was filtered and dried under reduced pressure to obtain 10.2 g (73%) of a crude product. The product was purified using 1000 ml of DEAE-Sepharose F.F. column (Amersham-Pharmacia Biotech). The elution was carried out with 0.4 to 100 mmol/L sodium chloride solution. A fraction containing the objective product was extracted with chloroform. The solvent was removed from the chloroform layer under reduced pressure and the residue was precipitated with diethyl ether to obtain 500 mg of the objective product.

<Gel Filtration HPLC Analysis>

Using TSK gel G-2000SW$_{XL}$ column, the product was analyzed under conditions similar to Example 1.

Retention time: 12.7 minutes

<$^1$H-NMR analysis (CDCl$_3$, 300 MHz)>;

δ (ppm): 3.38 (s, 6H), 3.64 (s, 8 nH), 0.85, 1.26 (each m, total 9H).

EXAMPLE 5

Synthesis of 5 kDa Double-chain Branched Polyethylene Glycol-cyclohexane Derivative Abbreviation: 5CHTM(2EU) (Compound No. 5)

A double-chain crude product wherein two molecules of mPEG were linked to cyclohexane trimethanol was obtained in a similar manner to Example 4. A fraction containing only double-chain PEG derivative was collected by purifying 2.7 g of the crude product by reversed phase HPLC using TSK gel ODS120-T column. Acetonitrile was removed form the fraction under reduced pressure and the mixture was extracted with chloroform. The chloroform layer was dried over anhydrous sodium sulfate and then dried under reduced pressure to obtain 227 mg of a double-chain PEG derivative (yield from the crude product: 8.4%). Then, 20 mg (2 μmol) of the double-chain PEG derivative was dried under reduced pressure, 1.2 mg (10 μmol) of DMAP and 2.6 mg (10 μmol) of DSC were added thereto, and then 1 ml of methylene chloride were added thereto, followed by stirring in an argon stream at room temperature for 4 days. The reaction. liquid was filtered and the filtrate was added dropwise to diethyl ether. The resulting precipitate was collected and dried under reduced pressure to obtain 15 mg of the objective product (yield: 75%).

<$^1$H-NMR analysis (CDCl$_3$, 300 MHz)>;
δ (ppm): 3.61 (s, 8 nH), 3.41 (s, 6H), 0.5-2.0 (m, 9H), 2.84 (s, 4H).

EXAMPLE 6

Synthesis of 5 kDa Double-chain Branched Polyethylene Glycol-cyclohexane Derivative Abbreviation: 5QNA(2UA) (Compound No. 6)

In 250 µl of dry DMF, 3 mg of (1R,3R,4R,5R)-(−)-quinic acid was dissolved and 17 µl of triethylamine and a catalytic amount of CuCl were added thereto. Furthermore, 344 mg of mPEG-NCO (average molecular weight:: 5,000, manufactured by Shearwater Polymers, Inc.) was added thereto, followed by stirring at room temperature for 1 hour. The mixture was added dropwise to 10-fold amounts of diethyl ether and the resulting precipitate was collected by filtration and dried under reduced pressure to obtain 306 mg (88%) of a crude objective product. Using DEAE-Sepharose F.F. column (Amersham-Pharmacia Biotech), the product was purified in a similar manner to Example 2. The objective fraction was extracted with chloroform and the solvent was removed under reduced pressure to obtain 36 mg (yield: 10.5%) of the objective compound.

<Gel Filtration HPLC Analysis>
Using TSK gel G-2000SW$_{XL}$ column, the product was analyzed under conditions similar to Example 1.

Retention time: 12.4 minutes

<$^1$H-NMR analysis (CDCl$_3$, 300 MHz)>;
δ (ppm): 5.7-4.8 (m, 3H), 3.33 (s, 6H), 3.64 (s, 8 nH).

EXAMPLE 7

Synthesis of 5 kDa Double-chain Branched Polyethylene Glycol-cyclohexene Derivative Abbreviation: 5SKA(2UA) (Compound No. 7)

In 250 µl of dry DMF, 3.2 mg of shikimic acid was dissolved and 15 µl of triethylamine and a catalytic amount of CuCl were added thereto. Furthermore, 300 mg of mPEG-NCO (average molecular weight:: 5,000, manufactured by Shearwater Polymers, Inc.) was added, followed by stirring at room temperature for 1 hour. The mixture was added dropwise to 10-fold amounts of diethyl ether and the resulting precipitate was collected by filtration and dried under reduced pressure to obtain 270 mg (89%) of a crude objective product. Using DEAE-Sepharose F.F. column (Amersham-Pharmacia Biotech), the product was purified in a similar manner to Example 2. An objective fraction was extracted with chloroform and the solvent was removed under reduced pressure to obtain 4 mg (yield: 1.3%) of the objective compound.

<Gel Filtration HPLC Analysis>
Using TSK gel G-2000SW$_{XL}$ column, the product was analyzed under conditions similar to Example 1.

Retention time: 12.4 minutes

<$^1$H-NMR analysis (CDCl$_3$, 300 MHz)>;
δ (ppm): 6.6-5.1 (m, 4H), 3.33 (s, 6H), 3.64 (s, 8 nH).

EXAMPLE 8

Synthesis of 5 kDa Double-chain Branched Polyethylene Glycol-cyclohexane Derivative Abbreviation: 5CHTM(2URa) (Compound No. 8)

In 0.5 ml of dehydrated DMF, 50 mg of cis,cis-1,3,5-cyclohexane trimethanol was dissolved and 17 mg of sodium hydride was added thereto, followed by stirring at 0° C. for 15 minutes. Then, 47 µl of 3-bromopropionaldehyde dimethyl acetal was added thereto, followed by stirring at room temperature for 16 hours. The mixture was purified using a silica gel column to obtain 15 mg of a compound wherein propionaldehyde dimethyl acetal was linked to cis,cis-1,3,5-cyclohexane trimethanol at the 1-position (yield: 38%).

<$^1$H-NMR analysis (DMSO-d$_6$, 300 MHz)>;
δ (ppm): 0.62 (m, 9H), 1.54-1.88 (m, 9H), 1.83 (q, J=6.20 Hz, 2H), 3.27 (d, J=6.30 Hz, 2H), 3.33 (s, 6H), 3.39 (d, J=6.30 Hz, 4H), 3.46 (t, J=6.20 Hz, 2H), 4.51 (t, J=5.70 Hz, 1H).

<Mass analysis (FAB-MS)>;
Found value: (M+H)$^+$ 277; Calculated value: C$_{14}$H$_{28}$O$_5$=276.

In 1 ml of dehydrated DMF, 15 mg of the obtained compound was dissolved and 31 µl of triethylamine and a catalytic amount of CuCl were added thereto. Furthermore, 598 mg of mPEG-NCO (average molecular weight:: 5,000, manufactured by Shearwater Polymers, Inc.) was added, followed by stirring at room temperature for 2 hours. The mixture was added dropwise to 10-fold amounts of diethyl ether and the resulting precipitate was collected by filtration and dried under reduced pressure. The resulting white solid (578 mg) was purified by reversed phase HPLC similar to Example 1 to obtain 383 mg of a purified material. A 100 mg portion thereof was dissolved in an aqueous solution of 70% acetic acid, followed by stirring at 40° C. for 16 hours. The reaction liquid was neutralized with an aqueous saturated sodium hydrogen carbonate solution and extracted with chloroform. After drying over anhydrous sodium sulfate, the reaction liquid was concentrated under reduced pressure. The condensate was added dropwise to 10-fold amounts of diethyl ether, and the resulting white precipitate was collected by filtration and dried under reduced pressure. The precipitate was again purified by reversed phase HPLC to obtain 39 mg of the objective product (yield: 41%).

<Gel Filtration HPLC Analysis>
Using TSK gel G-2000SW$_{XL}$ column, the product was analyzed under conditions similar to Example 1.

Retention time: 12.7 minutes

<$^1$H-NMR analysis (CDCl$_3$, 300 MHz)>; δ (ppm): 3.38 (s, 6H), 9.79 (t, J=1.56 Hz, 1H), 3.64 (s, 8 nH);

EXAMPLE 9

Synthesis of 5 kDa Double-chain Branched Polyethylene Glycol-cyclohexane Derivative Abbreviation: 5CHTM(2UM) (Compound No. 9)

In about 10 ml of acetonitrile, 100 mg of cis,cis-1,3,5-cyclohexane trimethanol synthesized in a similar manner to Example 4 and 735 mg of DSC were dissolved, and then 210 mg of DMAP was added thereto, followed by stirring at room temperature for 5 hours. The solvent was removed under reduced pressure, appropriate amounts of methylene chloride and 0.1 mol/L hydrochloric acid were added thereto, and the mixture was extracted. The organic layer was dried under reduced pressure to obtain 333 mg of cis,cis-1,3,5-tris(succinimidyloxycarbonyloxymethyl)cyclohexane (yield: 97%) [FAB-MS: 598(M+H)+].

In methylene chloride, 30 mg (0.05 mmol) of the compound and 500 mg (0.1 mmol) of mPEG-NH$_2$ (average molecular weight: 5,000, manufactured by Nippon Oil & Fats Co., Ltd.) were dissolved, and 20 µl of TEA was added thereto, followed by stirring for 2 hours. Then, 42 µl (0.5 mmol) of propylene diamine (manufactured by Aldrich) was added thereto, followed by further stirring at room temperature for 2 hours. The reaction liquid was filtered and the filtrate was added dropwise to diethyl ether and the resulting precipitate was dried under reduced pressure to obtain 430 mg of a powder (yield: 86%). A 425 mg portion of the powder was dissolved in 200 ml of water and purified using 20 ml of SP Sepharose F.F. column (Amersham-Pharmacia Biotech), and an objective fraction containing double-chain PEG was extracted with chloroform. The resulting organic layer was added dropwise to diethyl ether and a purified precipitate was dried under reduced pressure. Then, 62.5 mg (6.25 µmol) of the resulting powder was dissolved in 0.5 ml of an aqueous saturated sodium hydrogen carbonate solution and 2.1 mg of ethoxycarbonylmaleimide was added under ice cooling, followed by stirring for 10 minutes. Thereafter, 1.5 ml of water was added thereto, followed by stirring at room temperature for 15 minutes, and the mixture was extracted three times with chloroform. The chloroform layer was dried over anhydrous sodium sulfate and the solvent was removed under reduced pressure to obtain 25 mg of a powder (yield: 40%).

<Gel Filtration HPLC Analysis>

Using TSK gel G-2000SW$_{XL}$ column, the product was analyzed under conditions similar to Example 1.

Retention time: 12.4 minutes

<$^1$H-NMR analysis (CDCl$_3$, 300 MHz)>;

δ (ppm): 0.63-0.75 (m, 3H), 1.75-1.78 (m, 12H), 3.1-3.3 (m, 12H), 3.38 (s, 6H), 3.64 (s, 8 nH), 5.20 (br, 3H), 6.73 (s, 2H).

EXAMPLE 10

Synthesis of 5 kDa Double-chain Branched Polyethylene Glycol-cyclohexane Derivative Abbreviation: 5CHTM(2EA2) (Compound No. 10)

In 23 ml of dehydrated DMSO, 100 mg of cis,cis-1,3,5-cyclohexane trimethanol prepared in a similar manner to Example 4 was dissolved and 958 ml of a tert-butanol solution (1M) of potassium tert-butoxide was added thereto, followed by stirring at room temperature for 1 hour. Then, bromoacetic acid tert-butyl ester was added thereto, followed by stirring at 90° C. for 16 hours. After cooling to room temperature, the mixture was purified using a silica gel column to obtain 22 mg of 1-O-tert-butoxycarbonylmethyl-cys,cys-1,3,5-cyclohexane trimethanol (yield: 13%).

<$^1$H-NMR analysis (DMSO-d$_6$, 300 MHz)>;

δ (ppm): 0.60 (m, 9H), 1.55-1.90 (m, 9H), 1.48 (s, 9H), 3.36 (d, J=6.42 Hz, 2H), 3.39 (d, J=6.15 Hz, 4H), 3.95 (s, 2H).

<Mass analysis (FAB-MS)>;

Found value: (M+H)+ 289; Calculated value: C$_{15}$H$_{28}$O$_5$ 288.

In 200 µl of dehydrated pyridine was dissolved 22 mg of the compound obtained in the above under an argon atmosphere, and 23 mg of tosyl chloride dissolved in 200 µl of dehydrated pyridine was added thereto. After stirring at 0° C. for 3 hours, 20 µl of water was added thereto and then 100 µl was added thereto. The reaction liquid was extracted with ice-cooled chloroform and the extract was washed with ice-cooled 1 mol/L hydrochloric acid, water and an aqueous saturated sodium hydrogen carbonate solution, successively. After drying over anhydrous sodium sulfate, the solvent was removed and the residue was purified using a silica gel column to obtain 22 mg of 1-O-tert-butoxycarbonylmethyl-3-O,5-O-di-tosyl-1,3,5-cyclohexane trimethanol (yield: 48%).

<$^1$H-NMR analysis (CDCl$_3$, 300 MHz)>;

δ (ppm): 1.26 (m, 9H), 1.75 (m, 9H), 1.47 (s, 9H), 2.46 (s, 6H), 3.29 (d, J=6.30 Hz, 2H), 3.80 (m, 4H), 3.89 (s, 2H), 7.36 (d, J=8.10 Hz, 2H), 7.76 (d, J=8.40 Hz, 2H);

<Mass analysis (FAB-MS)>;

Found value: (M-tert-butyl+2H)+ 541 Calculated value: C$_{29}$H$_{40}$O$_9$S$_2$=596.

In 2 ml of dehydrated toluene, 1.4 g of mPEG (average molecular weight: 5,000, manufactured by Nippon Oil & Fats Co., Ltd.) was dissolved, and the mixture was added dropwise to 26 mg of sodium hydride under an argon atmosphere, followed by stirring for 30 minutes. Thereto, 76 mg of 1-O-tert-butoxycarbonylmethyl-3-O,5-O-ditosyl-1,3,5-cyclohexane trimethanol dissolved in 500 µl of dehydrated toluene was added dropwise, followed by stirring at room temperature for overnight. Thereafter, the reaction liquid was added dropwise to diethyl ether and the resulting white precipitate was collected by filtration and dried under reduced pressure. The resulting white solid (1.2 g) was purified using 120 ml of DEAE Sepharose F.F. column in a similar manner to Example 4 to obtain 154 mg of the objective product (yield: 11%).

<Gel Filtration HPLC Analysis>

Using TSK gel G-2000SW$_{XL}$ column, the product was analyzed under conditions similar to Example 1.

Retention time: 12.7 minutes

<$^1$H-NMR analysis (CDCl$_3$, 300 MHz)>;

δ (ppm): 3.38 (s, 6H), 3.64 (s, 8 nH), 0.58 (m, 9H), 1.72-1.93 (m, 9H), 3.38 (s, 6H).

EXAMPLE 11

Production of Recombinant Human Interferon-β Modified With 5 kDa Double-chain Branched Polyethylene Glycol Abbreviation: 5CHTO(2UU)-rhIFN-β

To 1.2 ml of a 1.3 mg/ml rhIFN-β solution obtained in Reference Example 6 which was prepared with a 20 mmol/L phosphate buffer (pH 7.5) containing sodium chloride, 15 mg (20 mol per mol of the protein) of the compound obtained in Example 1 was added, and the mixture was allowed to react at 4° C. for overnight. Then, the reaction liquid was subjected to gel filtration using 24 ml of Sephacryl S300 column (manufactured by Amersham-Pharmacia Biotech). A 20 mmol/L phosphate buffer containing ethylene glycol and 0.1 mol/L sodium chloride was used as an eluent. A fraction (14.5 ml) containing the objective product was collected, diluted with 14.5 ml of water and then purified using 1.5 ml of CM-Sepharose F.F. column (manufactured by Amersham-Pharmacia Biotech). The fraction obtained by gel filtration was applied into the column and, and the column was washed with 3 ml of the buffer and eluted and fractionated with the buffer containing 1 mol/L sodium chloride. Thus, 1.4 ml of a fraction containing 0.24 mg/ml of the objective product was recovered (yield: 21.5%).

<Electrophoresis>

SDS-PAGE was carried out in the presence of 2-mercaptoethanol to confirm the bands of 1 to 5 molecules-linked substances.

<Electrophoresis Conditions>

Gel: PAGEL SPG 520L (manufactured by ATTO) Staining: FAST STAIN™ Molecular weight marker: low molecular weight standard (manufactured by Biorad)

<Gel Filtration HPLC Analysis>

Mobile phase: 150 mmol/ml sodium chloride, 20 mmol/L sodium acetate buffer (pH 4.5) Flow rate: 0.5 ml/minute Detection: UV 280 nm Separating column: TSK gel G-4000SW$_{XL}$ (7.8 mm×300 mm×two columns connected) (manufactured by Tosoh Corporation) Retention time: 40.3 minutes (1 to 4 molecules-linked substances)

EXAMPLE 12

Production of Recombinant Human Interferon-β Modified With 5 kDa Double-chain Branched Polyethylene Glycol Abbreviation: 5CHTC(2AA)-rhIFN-β

In 1.0 ml of methylene chloride, 100 mg (0.01 mmol) of the compound of Example 2 was dissolved and 5.7 mg (0.05 mmol) of NHS and 10.3 mg (0.05 mmol) of DCC were added thereto, followed by stirring in an argon stream at 0° C. for 30 minutes. Thereafter, the mixture was stirred at room temperature for 3 hours and then the reaction liquid was added dropwise to diethyl ether. The resulting white precipitate was dried under reduced pressure to obtain 65.0 mg of the NHS ester of the compound of Example 2 (yield: 65.0%).

To 1.28 ml (1.067 mg/ml) of an rhIFN-β solution obtained in Reference Example 6 which was prepared with 20 mmol/L phosphate buffer (pH 7.5) containing sodium chloride, 17 mg (25 mol per mol of the protein) of the above NHS ester was added, the mixture was allowed to react at 4° C. for overnight. Then, the reaction liquid was subjected to gel filtration using 24 ml of Sephacryl S300 column (manufactured by Amersham-Pharmacia Biotech). A 20 mmol/L phosphate buffer containing ethylene glycol and 0.1 mol/L sodium chloride was used as an eluent. A fraction (24 ml) containing the objective product was collected, diluted with 24 ml of water, and then purified using 1.5 ml of CM-Sepharose F.F. column (manufactured by Amersham-Pharmacia Biotech). The fraction obtained by gel filtration was applied into the column, and the column was washed with 3 ml of the buffer and eluted and fractionated with the buffer containing 1 mol/L sodium chloride. Thus, 1.5 ml of a fraction containing 0.49 mg/ml of the objective product was recovered (yield: 44.5%).

<Electrophoresis>

SDS-PAGE was carried out in a similar manner to Example 11 to confirm the bands of 1 to 4 molecules-linked substances.

<Gel Filtration HPLC Analysis>

Using two TSK gel G-4000SW$_{XL}$ columns, the product was analyzed under conditions similar to Example 11.

Retention time:
  43.9 minutes (1 molecule-linked substance)
  41.0 minutes (2 molecules-linked substance)

EXAMPLE 13

Production of Recombinant Human Interferon-β Modified With 5 kDa Double-chain Branched Polyethylene Glycol Abbreviation: 5CHTO(2EA)-rhIFN-β

In methylene chloride, 20 mg of the thoroughly dried compound of Example 3 was dissolved and 1.15 mg of NHS and 2.06 mg of DCC were added thereto in an argon stream, followed by stirring under ice cooling for 30 minutes and then at room temperature for 2 hours. An insoluble matter was filtered and the filtrate was added dropwise to diethyl ether to form a precipitate. The precipitate was dried under reduced pressure to obtain 14.5 mg of an NHS ester (yield: 72.5%).

To 0.78 ml (0.937 mg/ml) of an rhIFN-β solution obtained in Reference Example 6 which was prepared with a 20 mmol/L phosphate buffer (pH 7.5) containing sodium chloride, 9.1 mg (25 mol per mol of the protein) of the above NHS ester was added, and the mixture was allowed to react at 4° C. for overnight. Then, the reaction liquid was subjected to gel filtration using 24 ml of Sephacryl S300 column (manufactured by Amersham-Pharmacia Biotech). A 20 mmol/L phosphate buffer containing ethylene glycol and 0.1 mol/L sodium chloride was used as an eluent. A fraction (8.5 ml) containing the objective product was collected, diluted with 8.5 ml of water, and then purified using 1.5 ml of CM-Sepharose F.F. column (manufactured by Amersham-Pharmacia Biotech). The fraction obtained by gel filtration was applied into the column, and the column was washed with 3 ml of the buffer and eluted and fractionated with the buffer containing 1 mol/L sodium chloride. Thus, 0.5 ml of a fraction containing 0.067 mg/ml of the objective product was recovered (yield: 4.5%).

<Electrophoresis>

SDS-PAGE was carried out in a similar manner to Example 11 to confirm the bands of 1 to 3 molecules-linked substances.

<Gel Filtration HPLC Analysis>

Using two TSK gel G-4000SW$_{XL}$ columns, the product was analyzed under conditions similar to Example 11.

Retention time: 35.9 minutes (1 to 3 molecules-linked substances)

EXAMPLE 14

Production of Recombinant Human Interferon-β Modified With 5 kDa Double-chain Branched Polyethylene Glycol Abbreviation: 5CHTM(2EA)-rhIFN-β

In methylene chloride, 487 mg (48.7 µmol) of the dried compound of Example 4 was dissolved, and 16.8 mg (146.0 µmol) and 30.1 mg (145.9 µmol) of DCC were added thereto in an argon stream, followed by stirring under ice cooling for 30 minutes and then at room temperature for 2 hours. An insoluble matter was filtered and the filtrate was added dropwise to diethyl ether to form a precipitate. The precipitate was dried under reduced pressure to obtain 260.0 mg of an NHS ester (yield: 53.4%).

To 1.2 ml (1.22 mg/ml) of an rhIFN-β solution obtained in Reference Example 6 which was prepared with 20 mmol/L phosphate buffer (pH 7.5) containing ethylene glycol and sodium chloride, 14.6 mg (20 mol per mol of the protein) of the above NHS ester was added, and the mixture was allowed to react at 4° C. for overnight. Then, the reaction liquid was subjected to buffer exchange into a 20 mmol/L phosphate buffer (pH 6.0) containing ethylene glycol using a gel filtration column of Sephadex-G25 (NAP-10, manufactured by Amersham-Pharmacia Biotech). A fraction obtained by gel filtration was applied into 1.5 ml of CM-Sepharose F.F. column (Amersham-Pharmacia Biotech), and the column was washed with 3 ml of the buffer and eluted and fractionated with the buffer containing 0.2 to 1.0 mol/L sodium chloride. Thus, 3.75 ml of a fraction containing 0.194 mg/ml of the objective product was recovered (yield: 49.7%).

<Electrophoresis>

SDS-PAGE was carried out in a similar manner to Example 11 to confirm the bands of 1 to 2 molecules-linked substances.

<Gel Filtration HPLC Analysis>

Using two TSK gel G-4000SW$_{XL}$ columns, the product was analyzed under conditions similar to Example 11.

Retention time:
  42.9 minutes (1 molecule-linked substance)
  40.2 minutes (2 molecules-linked substance)

EXAMPLE 15

Production of Natural Human Interferon-β Modified With 5 kDa Double-chain Branched Polyethylene Glycol Abbreviation: 5CHTM(2EA)-Natural hIFN-β

In 200 μl of isotonic phosphate buffer, 10 μg of natural hIFN-β (manufactured by STRATHMANN BIOTECH GMBH) was dissolved, 1.5 mg (300 mol per mol of the protein) of the NHS ester of 5CHTM(2EA) obtained in a similar manner to Example 14 was added thereto, and the mixture was allowed to react at 20° C. for overnight. Then, the reaction liquid was subjected to buffer exchange into a 20 mmol/L phosphate buffer containing ethylene glycol using a gel filtration column of Sephadex G-25 (NAP-5, Amersham-Pharmacia Biotech) and purified on 0.5 ml of CM-Sepharose F.F. column (Amersham-Pharmacia Biotech). The reaction liquid (0.5 ml) was added to the column, and the column was washed with 5 ml of the buffer and eluted with the buffer containing 0.35 mol/L sodium chloride. An objective fraction (1.0 ml) was concentrated to obtain 0.19 ml of a solution containing 0.021 mg/ml of the objective product (yield: 39.9%).

EXAMPLE 16

Production of Recombinant Human Interferon-α Modified With 5 kDa Double-chain Branched Polyethylene Glycol Abbreviation: 5CHTC(2AA)-rhIFNα

To 0.1 ml of 1.0 mg/ml rhIFN-α [Immune Biology Laboratory (IBL)] prepared with an isotonic phosphate buffer (pH 7.5), 1.5 mg (30 mol per mol of the protein) of the NHS ester of 5CHTC(2AA) obtained in a similar manner to Example 12 was added, and the mixture was allowed to react at 4° C. for overnight. Then, 80 μl of the reaction liquid was subjected to buffer exchange into a 20 mmol/L sodium acetate buffer (pH 4.5) using Sephadex G-25 column (NAP-5, manufactured by Amersham-Pharmacia Biotech) to recover 0.8 ml. The recovered solution was applied into 1.0 ml of SP-Sepharose F.F. column (manufactured by Amersham-Pharmacia Biotech), and the column was washed with 2.0 ml of 20 mmol/L sodium acetate buffer (pH 4.5) and eluted with the buffer containing 0.1 to 1.0 mol/L sodium chloride. A solution (0.5 ml) containing 80 μg/ml of the objective product was obtained (yield: 40.0%).

<Electrophoresis>

SDS-PAGE was carried out in a similar manner to Example 11 to confirm the bands of 1 to 4 molecules-linked substances.

<Gel Filtration HPLC Analysis>

Using TSK gel G-4000SW$_{XL}$ columns, the product was analyzed under conditions similar to Example 11.

Retention time:
  43.1 minutes (1 molecule-linked substance)
  40.5 minutes (2 molecules-linked substance)

EXAMPLE 17

Production of Recombinant Human Interferon-α Modified With 5 kDa Double-chain Branched Polyethylene Glycol Abbreviation: 5CHTM(2EA)-rhIFN-α

To 0.1 ml of 0.95 mg/ml rhIFN-α (IBL) prepared with an isotonic phosphate buffer (pH 7.5), 1.5 mg (30 mol per mol of the protein) of the NHS ester of 5CHTM(2EA) obtained in a similar manner to Example 14 was added, and the mixture was allowed to react at 4° C. for overnight. Then, 0.1 ml of the reaction liquid was subjected to buffer exchange into a 20 mmol/L sodium acetate buffer (pH 4.5) using Sephadex G-25 column (NAP-5, manufactured by Amersham-Pharmacia Biotech) to recover 0.8 ml. The recovered solution was applied into 1.0 ml of SP-Sepharose F.F. column (manufactured by Amersham-Pharmacia Biotech), and the column was washed with 2.0 ml of a 20 mmol/L sodium acetate buffer (pH 4.5) and eluted with the buffer containing 0.1 to 1.0 mol/L sodium chloride. A solution (0.6 ml) containing 50 μg/ml of the objective product was obtained (yield: 31.6%).

<Electrophoresis>

SDS-PAGE was carried out in a similar manner to Example 11 to confirm the bands of 1 to 2 molecules-linked substances.

<Gel Filtration HPLC Analysis>

Using TSK gel G-4000SW$_{XL}$ columns, the product was analyzed under conditions similar to Example 11.

Retention time:
  42.9 minutes (1 molecule-linked substance)
  41.2 minutes (2 molecules-linked substance)

EXAMPLE 18

Production of Recombinant Human Interferon-γ Modified With 5 kDa Double-chain Branched Polyethylene Glycol Abbreviation: 5CHTC(2AA)-rhIFN-γ

To 0.1 ml of an rhIFN-γ (0.10 mg/ml) obtained in Reference Example 7 which was prepared with 20 mmol/L phosphate buffer (pH 7.8) containing ethylene glycol and sodium chloride, 1.0 mg (200 mol per mol of the protein) of the NHS ester of 5CHTC(2AA) obtained in a similar manner to Example 12 was added, and the mixture was allowed to react at 4° C. for overnight.

<Electrophoresis>

SDS-PAGE was carried out in a similar manner to Example 11 to confirm the bands of 1 to 3 molecules-linked substances.

EXAMPLE 19

Production of Recombinant Human Interferon-γ Modified With 5 kDa Double-chain Branched Polyethylene Glycol Abbreviation: 5CHTM(2EA)-rhIFN-γ

To 0.1 ml of rhIFN-γ (0.8 mg/ml) obtained in Reference Example 7 which was prepared with a 20 mmol/L phosphate buffer (pH 7.8) containing ethylene glycol and sodium chloride, 10.1 mg (30 mol per mol of the protein) of the NHS ester of 5CHTM(2EA) obtained in a similar manner to Example 14 was added, and the mixture was allowed to react at 4° C. for overnight.

<Electrophoresis>

SDS-PAGE was carried out in a similar manner to Example 11 to confirm the bands of 1 to 3 molecules-linked substances.

EXAMPLE 20

Production of Recombinant Human Granulocyte-colony Stimulating Factor Derivative Modified With 5 kDa Double-chain Branched Polyethylene Glycol Abbreviation: 5CHTO(2UU)-rhG-CSF Derivative To 100 μl of rhG-CSF derivative obtained in Reference Example 5 which was adjusted to 3.2 mg/ml with 50 mmol/L phosphate buffer (pH 7.5), 1.7 mg (10 mol per mol of the protein) of the compound of Example 1 was added, and the mixture was allowed to react at 4° C. for overnight. Then, the reaction liquid was diluted ten times with a 20 mmol/L acetate buffer (pH 4.5) and 900 μl of the dilute was applied into Sephadex G-25 column (NAP-10, manufactured by Amersham-Pharmacia Biotech) equilibrated with the buffer to recover 1.3 ml. The recovered solution was applied into 0.7 ml of SP-Sepharose F.F. column (manufactured by Amersham-Pharmacia Biotech), the column was washed with 4.9 ml of a 20 mmol/L sodium acetate buffer (pH 4.5), the buffer containing 75 to 500 mmol/L sodium chloride was applied to elution. Fractions containing the objective product were combined and concentrated. A solution (360 μl) containing 402 μg/ml of the objective product was obtained (yield: 50.3%).

<Electrophoresis>

SDS-PAGE was carried out in a similar manner to Example 11 to confirm the bands of 1 to 4 molecules-linked substances.

<Gel Filtration HPLC Analysis>

Using two TSK gel G-4000SW$_{XL}$ columns, the product was analyzed under conditions similar to Example 11.

Retention time:
  42.8 minutes (1 molecule-linked substance)
  41.3 minutes (2 molecules-linked substance)

EXAMPLE 21

Production of Recombinant Human Granulocyte-colony Stimulating Factor Derivative Modified With 5 kDa Double-chain Branched Polyethylene Glycol Abbreviation: 5CHTC(2AA)-rhG-CSF Derivative To 100 μl of rhG-CSF derivative obtained in Reference Example 5 which was adjusted to 3.9 mg/ml with a 50 mmol/L phosphate buffer (pH 7.5), 5.1 mg (25 mol per mol of the protein) of the NHS ester of 5CHTC(2AA) obtained in a similar manner to Example 12 was added, and the mixture was allowed to react at 4° C. for overnight. Then, the reaction liquid was diluted ten times and 900 μl of the dilute was subjected to buffer exchange into a 20 mmol/L sodium acetate buffer (pH 4.5) using Sephadex G-25 column (NAP-10, manufactured by Amersham-Pharmacia Biotech) to recover 1.3 ml. The recovered solution was applied into 0.7 ml of SP-Sepharose F.F. column (manufactured by Amersham-Pharmacia Biotech), and the column was washed with 4.9 ml of a 20 mmol/L sodium acetate buffer (pH 4.5) and eluted with the buffer containing 100 mmol/L sodium chloride. An objective fraction was concentrated to obtain a solution (500 μl) containing 179 μg/ml of the objective product (yield: 25.8%).

<Electrophoresis>

SDS-PAGE was carried out in a similar manner to Example 11 to confirm the bands of 1 to 3 molecules-linked substances.

<Gel Filtration HPLC Analysis>

Using two TSK gel G-4000SW$_{XL}$ columns, the product was analyzed under conditions similar to Example 11.

Retention time:
  42.8 minutes (1 molecule-linked substance)
  40.3 minutes (2 molecules-linked substance)

EXAMPLE 22

Production of Recombinant Human Granulocyte-colony Stimulating Factor Derivative Modified With 5 kDa Double-chain Branched Polyethylene Glycol Abbreviation: 5CHTO(2EA)-rhG-CSF Derivative To 100 μl of rhG-CSF derivative obtained in Reference Example 5 which was adjusted to 3.8 mg/ml with a 50 mmol/L phosphate buffer (pH 7.5), 6.0 mg (25 mol per mol of the protein) of the NHS ester of 5CHTO(2EA) obtained in a similar manner to Example 13 was added, and the mixture was allowed to react at 4° C. for overnight. Then, the reaction liquid was diluted ten times and 900 μl of the dilute was subjected to buffer exchange into a 20 mmol/L sodium acetate buffer (pH 4.5) using Sephadex G-25 column (NAP-10, manufactured by Amersham-Pharmacia Biotech) to recover 1.3 ml. The recovered solution was applied into 0.7 ml of SP-Sepharose F.F. column (manufactured by Amersham-Pharmacia Biotech), and the column was washed with 4.9 ml of a 20 mmol/L sodium acetate buffer (pH 4.5) and eluted with the buffer containing 100 to 500 mmol/L sodium chloride. Fractions containing the objective product were combined and concentrated. A solution (450 tl) containing 335 μg/ml of the objective product was obtained (yield: 44.2%).

<Electrophoresis>

SDS-PAGE was carried out in a similar manner to Example 11 to confirm the bands of 1 to 3 molecules-linked substances.

<Gel Filtration HPLC Analysis>

Using TSK gel G-4000SW$_{XL}$ column, the product was analyzed under conditions similar to Example 11.

Retention time:
  42.6 minutes (1 molecule-linked substance)
  39.5 minutes (2 molecules-linked substance)

EXAMPLE 23

Production of Recombinant Human Granulocyte-colony Stimulating Factor Derivative Modified With 5 kDa Double-chain Branched Polyethylene Glycol Abbreviation: 5CHTM(2EA)-rhG-CSF Derivative In methylene chloride, 487 mg (48.7 μmol) of the thoroughly dried compound of Example 4 was dissolved, and 16.8 mg (146.0 µmol) of NHS and 30.1 mg (145.9 µmol) of DCC were added thereto in an argon stream, followed by stirring under ice cooling for 30 minutes and then at room temperature for 2 hours. An insoluble matter was filtered and the filtrate was added dropwise to diethyl ether. A precipitate was collected and dried under reduced pressure to obtain 260.0 mg of the NHS ester of the compound 4 (yield: 53.4%).

To 1.25 ml (4.0 mg/ml) of rhG-CSF derivative obtained in Reference Example 5 which was prepared with a 50 mmol/L phosphate buffer (pH 7.4), 26.6 mg (25 mol per mol of the protein) of the above NHS ester was added, and the mixture was allowed to react at 4° C. for overnight. Then, 1.0 ml of the reaction liquid was subjected to buffer exchange into a 20 mmol/L sodium acetate buffer (pH 4.5) using Sephadex G-25 column (NAP-10, Amersham-Pharmacia Biotech) to recover 1.5 ml. The recovered solution was purified using 5.0 ml of SP-Sepharose F.F. column (Amersham-Pharmacia Biotech). After washing unadsorbed components with 10 ml of the buffer, the column was eluted with the buffer containing 0.1 to 0.5 mol/L sodium chloride. A fraction containing the objective product was diluted three times and again purified similarly on SP-Sepharose F.F. column. A fraction (15 ml) containing the objective product was recovered and then concentrated to obtain a solution (0.7 ml) containing 1.86 mg/ml of the objective product (yield: 32.5%).

<Electrophoresis>
SDS-PAGE was carried out in a similar manner to Example 11 to confirm the bands of 1 to 3 molecules-linked substances.

<Gel Filtration HPLC Analysis>
Using two TSK gel G-4000SW$_{XL}$ columns, the product was analyzed under conditions similar to Example 11.

Retention time:
48.7 minutes (1 molecule-linked substance)
46.9 minutes (2 molecules-linked substance)

EXAMPLE 24

Production of Recombinant Human Granulocyte-colony Stimulating Factor Derivative Modified With 5 kDa Double-chain Branched Polyethylene Glycol Abbreviation: 5CHTM(2EU)-rhG-CSF Derivative To 50 µl of rhG-CSF derivative obtained in Reference Example 5 which was adjusted to 3.9 mg/ml with a 50 mmol/L phosphate buffer (pH 7.3), 1.0 mg (10 mol per mol of the protein) of the compound of Example 5 was added, and the mixture was allowed to react at 4° C. for overnight.

<Electrophoresis>
SDS-PAGE was carried out in a similar manner to Example 11 to confirm the bands of 1 to 2 molecules-linked substances.

EXAMPLE 25

Production of Recombinant Human Granulocyte-Stimulating Factor Modified With 5 kDa Double-Chain Branched Polyethylene Glycol Abbreviation: 5CHTM(2EA)-rhG-CSF To 0.9 ml of an rhG-CSF solution at 3.9 mg/ml adjusted with an isotonic phosphate buffer (pH 7.4), 28.0 mg (15 equivalents per mol of the protein) of the NHS ester of 5CHTM(2EA) obtained in a similar manner to Example 14 was added, and the mixture was allowed to react at 4° C. for overnight. Then, 0.8 ml of the reaction liquid was subjected to buffer exchange into a 20 mmol/L sodium acetate buffer (pH 4.5) using Sephadex G-25 column (NAP-10, Amersham-Pharmacia Biotech) to recover 1.5 ml. The recovered solution was added to 5.0 ml of SP-Sepharose F.F. column (Amersham-Pharmacia Biotech). After flowing 10 ml of a sodium acetate buffer, the column was eluted and fractionated with the buffer containing 0.05 to 0.3 mol/L sodium chloride. An objective fraction (10 ml) was collected and then concentrated to obtain a solution (1.0 ml) containing 1.3 mg/ml of the objective product (yield: 33.0%).

<Electrophoresis>
SDS-PAGE was carried out in a similar manner to Example 11 to confirm the bands of 1 to 3 molecules-linked substances.

<Gel Filtration HPLC Analysis>
Using two TSK gel G-4000SW$_{XL}$ columns, the product was analyzed under conditions similar to Example 11.

Retention time:
42.8 minutes (1 molecule-linked substance)
40.1 minutes (2 molecules-linked substance)

EXAMPLE 26

Production of Recombinant Human Granulocyte-Colony Stimulating Factor Modified With 5 kDa Double-Chain Branched Polyethylene Glycol Abbreviation: 5CHTC(2AA)-rhG-CSF To 0.2 ml of an rhG-CSF solution adjusted to 3.9 mg/ml with an isotonic phosphate buffer (pH 7.4), 10.0 mg (25 equivalents per mol of the protein) of the NHS ester of 5CHTC(2AA) obtained in a similar manner to Example 12 was added, and the mixture was allowed to react at 4° C. for overnight.

Then, 0.2 ml of the reaction liquid was subjected to buffer exchange into a 20 mmol/L sodium acetate buffer (pH 4.5) using Sephadex G-25 column (NAP-5, Amersham-Pharmacia Biotech) to recover 1.0 ml. The recovered solution was added to 1.0 ml of SP-Sepharose F.F. column (Amersham-Pharmacia Biotech). After flowing 2.5 ml of a sodium acetate buffer, the column was washed and fractionated with the buffer containing 0.05 to 0.3 mol/L sodium chloride. An objective fraction (3.5 ml) was collected and then concentrated to obtain a solution (0.3 ml) containing 0.7 mg/ml of the objective product (yield: 26.8%).

<Electrophoresis>
SDS-PAGE was carried out in a similar manner to Example 11 to confirm the bands of 1 to 3 molecules-linked substances.

<Gel Filtration HPLC Analysis>
Using two TSK gel G-4000SW$_{XL}$ columns, the product was analyzed under conditions similar to Example 11.

Retention time:
42.9 minutes (1 molecule-linked substance)
40.4 minutes (2 molecules-linked substance)

EXAMPLE 27

Production of Bovine Cu/Zn Superoxide Dismutase Modified With 5 kDa Double-Chain Branched Polyethylene Glycol Abbreviation: 5CHTC(2AA)-bSOD In 1 ml of methylene chloride, 30 mg (3 µmol) of the thoroughly dried compound of Example 2 was dissolved, and 1.7 mg (0.015 mM) of NHS and 3.1 mg (0.015 mM) of DCC were added thereto, followed by stirring at 0° C. for 30 minutes. Then, the mixture was stirred at room temperature for 3 hours and the reaction liquid was added dropwise to diethyl ether. The resulting white precipitate was dried under reduced pressure to obtain 21 mg of the NHS ester of the compound of Example 2 (yield: 70%).

To 50 µl of a bovine Cu/Zn superoxide dismutase solution (2 mg/ml, pH 9 borate buffer, manufactured by Wako Pure Chemical Industries, Ltd.), 10 µl (50 mol per mol of the protein) of an aqueous solution (156 mg/mL) of the above NHS ester prepared immediately before use was added, and the mixture was allowed to react at 4° C. for overnight.

<Electrophoresis>

SDS-PAGE was carried out in a similar manner to Example 11 to confirm the bands of 1 to 2 molecules-linked substances.

EXAMPLE 28

Production of Bovine Cu/Zn Superoxide Dismutase Modified With 5 kDa Double-Chain Branched Polyethylene Glycol Abbreviation: 5CHTO( 2EA)-bSOD A 20 mg portion of the compound of Example 3 was activated under conditions similar to Example 13 to obtain 13 mg of an NHS ester (yield: 65%).

Then, to 50 µl of a bovine Cu/Zn superoxide dismutase solution (2 mg/ml, pH 9 borate buffer, manufactured by Wako Pure Chemical Industries, Ltd.), 10 µl (50 mol per mol of the protein) of an aqueous solution (156 mg/ml distilled water) of the above NHS ester prepared immediately before use was added, and the mixture was allowed to react at 4° C. for overnight.

<Electrophoresis>

SDS-PAGE was carried out in a similar manner to Example 11 to confirm the bands of 1 to 2 molecules-linked substances.

EXAMPLE 29

Production of Bovine Cu/Zn Superoxide Dismutase Modified With 5 kDa Double-Chain Branched Polyethylene Glycol Abbreviation: 5CHTO(2UU)-bSOD To 50 µl of a bovine Cu/Zn superoxide dismutase solution (2 mg/ml, pH 9 borate buffer, manufactured by Wako Pure Chemical Industries, Ltd.), 10 µl (50 mol per mol of the protein) of an aqueous solution (156 mg/ml distilled water) of the compound obtained in Example 1 was added, and the mixture was allowed to react at 4° C. for overnight.

<Electrophoresis>

SDS-PAGE was carried out in a similar manner to Example 11 to confirm the bands of 1 to 3 molecules-linked substances.

EXAMPLE 30

Production of Bovine Cu/Zn Superoxide Dismutase Modified With 5 kDa Double-Chain Branched Polyethylene Glycol Abbreviation: 5CHTM(2EA)-bSOD The compound (487 mg, 48.7 µmol) of Example 4 was activated under conditions similar to Example 14 to obtain 260 mg of an NHS ester (yield: 53.4%).

To 50 µl of a bovine Cu/Zn superoxide dismutase solution (2 mg/ml, pH 9 borate buffer, manufactured by Wako Pure Chemical Industries, Ltd.), 10 µl (50 mol per mol of the protein) of an aqueous solution (156 mg/ml distilled water) of the above NHS ester prepared immediately before use was added, and the mixture was allowed to react at 4° C. for overnight.

<Electrophoresis>

SDS-PAGE was carried out in a similar manner to Example 11 to confirm the bands of 1 to 3 molecules-linked substances.

EXAMPLE 31

Production of Bovine Cu/Zn Superoxide Dismutase Modified With 5 kDa Double-Chain Branched Polyethylene Glycol Abbreviation: 5CHTM(2EA)-bSOD (purified)

The compound (360 mg, 36.0 µmol) of Example 4 was activated under conditions similar to Example 14 to obtain 181.9 mg of an NHS ester (yield: 50.5%).

To 2.2 ml of a bovine Cu/Zn superoxide dismutase solution (2 mg/ml, pH 9 borate buffer, manufactured by Wako Pure Chemical Industries, Ltd.), 33.9 mg (25 mol per mol of the protein) of the above NHS ester was added, and the mixture was allowed to react at 4° C. for overnight. Then, the reaction liquid was purified using 4.3 ml of SP-Sepharose F.F. column (Amersham-Pharmacia Biotech). The reaction liquid was applied to the column, and the column was washed with a 20 mmol/L sodium acetate buffer (pH 3.5) and eluted and fractionated with the buffer containing 0.1 to 1.0 mol/L sodium chloride. Thereafter, an objective fraction which was free of unmodified SOD was concentrated to obtain a solution (200 µl) of 3.73 mg/ml (yield: 17.2%). Furthermore, an aqueous $CUSO_4$ solution and an aqueous $ZnSO_4$ solution were added thereto to give 10 mmol/L respectively to thereby restore the activity.

<Electrophoresis>

SDS-PAGE was carried out in a similar manner to Example 11 to confirm the bands of 1 to 3 molecules-linked substances.

EXAMPLE 32

Production of Human Cu/Zn Superoxide Dismutase Modified With 5 kDa Double-Chain Branched Polyethylene Glycol Abbreviation: 5CHTM(2EA)-hSOD The compound (487 mg, 48.7 µmol) of Example 4 was activated under conditions similar to Example 14 to obtain 260 mg of an NHS ester (yield: 53.4%).

To 50 µl of a human Cu/Zn superoxide dismutase solution (1.9 mg/ml, pH 9 borate buffer, manufactured by CELLULAR PRODUCTS, INC.), 10 µl (50 mol per mol of the protein) of an aqueous solution (156 mg/ml distilled water) of the above NHS ester prepared immediately before use was added, and the mixture was allowed to react at 4° C. for overnight.

<Electrophoresis>

SDS-PAGE was carried out in a similar manner to Example 11 to confirm the bands of 1 to 3 molecules-linked substances.

EXAMPLE 33

Production of Recombinant Human Interferon-β Modified With 5 kDa Double-Chain Ranched Polyethylene Glycol Abbreviation:5CHTM(2EA)-$^{17}$Ser rhIFN-β

To 0.1 ml (1.0 mg/ml) of a $^{17}$Ser rhIFN-β (manufactured by Chiron) solution prepared with a 20 mmol/L phosphate buffer (pH 7.6) containing ethylene glycol and sodium chloride, 1.3 mg (25 mol per mol of the protein) of the NHS ester of 5CHTM(2EA) obtained in a similar manner to Example 14 was added, and the mixture was allowed to react at 4° C. for overnight. Then, the reaction liquid was subjected to buffer exchange into a 20 mmol/L phosphate buffer (pH 6.0) using Sephadex G-25 column (NAP-5, Amersham-Pharmacia Biotech). The fraction obtained by gel filtration was applied into 0.25 ml of CM Sepharose F.F. column (Amersham-Pharmacia Biotech), the column was washed with 4.0 ml of the buffer and eluted and fractionated with the buffer containing 0.2 to 0.35 mol/L sodium chloride. A fraction (0.75 ml) containing 39 µg/ml of the objective product was recovered (yield: 39%).

<Electrophoresis>
SDS-PAGE was carried out in a similar manner to Example 11 to confirm the bands of 1 to 3 molecules-linked substances.

<Gel Filtration HPLC Analysis>
Using two TSK gel G-4000SW$_{XL}$ columns, the product was analyzed under conditions similar to Example 11.

Retention time: 41.3 minutes (1 to 3 molecules-linked substances)

EXAMPLE 34

Production of Human Cu/Zn Superoxide Dismutase Modified With 5 kDa Double-Chain Branched Polyethylene Glycol Abbreviation: 5CHTM(2UM)-hSOD To 0.6 ml of a human Cu/Zn superoxide dismutase solution [2.63 mg/ml, phosphate buffer (pH 7.5), manufactured by CELLULAR PRODUCTS, INC.] was added 3.13 mg (10 mol per mol of the protein) of the compound of Example 9 [5CHTM(2UM)], and the mixture was allowed to react at 4° C. for overnight. Then, the reaction liquid was purified using 20 ml of Sephacryl S-300 gel filtration column (Amersham-Pharmacia Biotech) with an acetate buffer (pH 4.5) containing 150 mmol/L sodium chloride. A fraction of the modified compound which was free of unreacted SOD was collected and concentrated to 0.5 ml. The solution was subjected to buffer exchange into a 20 mmol/L acetate buffer (pH 3.5) using Sephadex G-25 column (NAP-5, Amersham-Pharmacia Biotech) to recover 0.8 ml. The recovered solution was applied to 0.7 ml of SP-Sepharose F.F. column (Amersham-Pharmacia Biotech). After flowing 3.5 ml of the buffer, the buffer containing 0.5 to 1.0 mol/L sodium chloride was eluted. An objective fraction was collected and then concentrated. Furthermore, an aqueous CuSO$_4$ solution and an aqueous ZnSO$_4$ solution were added to give 10 mmol/L respectively to thereby restore the activity of SOD. A solution (180 µl) containing 0.25 mg/ml of the objective product was obtained (yield: 4.5%).

<Electrophoresis>
SDS-PAGE was carried out in a similar manner to Example 11 to confirm the band of 1 molecule-linked substance.

EXAMPLE 35

Preparation of Recombinant Human Granulocyte-Colony Stimulating Factor Derivative Modified With 5 kDa Double-Chain Branched Polyethylene Glycol Abbreviation: 5CHTM(2URa)-rhG-CSF Derivative To 50 µl of rhG-CSF derivative obtained in Reference Example 5 which was adjusted to 3.9 mg/ml with a 50 mmol/L phosphate buffer (pH 7.5), 5.2 mg (50 mol per mol of the protein) of the PEG derivative [5CHTM(2URa)] obtained in Example 8 and 10 µl of sodium borohydride solution (120 mmol/l) were added successively, and the mixture was allowed to react at room temperature for 18 hours.

<Electrophoresis>
SDS-PAGE was carried out in a similar manner to Example 11 to confirm the band of 1 molecule-linked substance.

EXAMPLE 36

Production of Recombinant Human Granulocyte-Colony Stimulating Factor Derivative Modified With 5 kDa Double-Chain Branched Polyethylene Glycol Abbreviation: 5CHTM(2EA2)-rhG-CSF Derivative In 1.0 ml of methylene chloride, 100 mg (0.01 mmol) of the compound of Example 10 was dissolved, and 3.5 mg (0.03 mmol) of NHS and 6.2 mg (0.03 mmol) of DCC were added thereto, followed by stirring under 0° C. for 90 minutes and then at room temperature for 2 hours in an argon stream. The reaction liquid was added dropwise to diethyl ether. The resulting white precipitate was dried under reduced pressure to obtain 56.5 mg of an NHS ester (yield: 56.5%).

To 210 µl of the rhG-CSF derivative obtained in Reference Example 5 which was adjusted to 3.9 mg/ml with a 50 mmol/L phosphate buffer (pH 7.5), 4.2 mg (10 mol per mol of the protein) of the above NHS ester was added, and the mixture was allowed to react at 4° C. for overnight. Then, the reaction liquid was subjected to buffer exchange into a 20 mmol/L acetate buffer (pH 4.5) using Sephadex G-25 column (NAP-5, Amersham-Pharmacia Biotech) and the product was successively purified using 0.7 ml of SP Sepharose F.F. column (Amersham-Pharmacia Biotech). The column was eluted with the buffer containing 75 mmol/L to 1 mol/L sodium chloride. A fraction containing 0.31 mg/ml of the objective product was obtained in an amount of 965 µl (yield: 39.6%).

<Electrophoresis>
SDS-PAGE was carried out in a similar manner to Example 11 to confirm the bands of 1 to 3 molecules-linked substances.

<Gel Filtration HPLC Analysis>
Using TSK gel G-4000SW$_{XL}$ column, the product was analyzed under conditions similar to Example 11.

Retention time:
42.2 minutes (1 molecule-linked substance)
40.6 minutes (2 molecules-linked substance)

EXAMPLE 37

Synthesis of 5 kDa Double-Chain Branched Polyethylene Glycol-Cyclohexane Derivative Abbreviation: 5CHTM(2UA) (Compound No. 37)

In 23 ml of anhydrous DMSO, 100 mg of cis,cis-1,3,5-cyclohexane trimethanol was dissolved and then 958 µl of a tert-butanol solution of potassium tert-butoxide (1 mol/L) was added thereto, followed by stirring at room temperature for 1 hour. Bromoacetic acid tert-butyl ester was added thereto, followed by stirring at 90° C. for 16 hours. After cooling to room temperature, the mixture was purified using a silica gel column to obtain 22 mg of the following compound (yield: 13%).

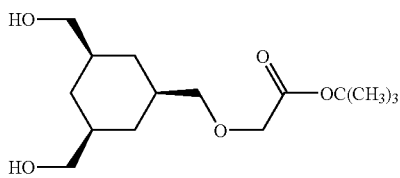

<$^1$H-NMR analysis (DMSO-d$_6$, 300 MHz)>;
δ (ppm): 0.5-1.9 (m, 9H), 1.48 (s, 9H), 3.36 (d, J=6.4 Hz, 2H), 3.39 (d, J=6.4 Hz, 4H), 3.95 (s, 2H);

<Mass analysis (FAB-MS)>;
Found value: (M+H)$^+$ 289 Calculated value: C$_{15}$H$_{28}$O$_5$=288.

Under an argon atmosphere, 867 mg of the above compound was dissolved in 5 ml of dehydrated acetonitrile and 1.95 g of DSC and 526 mg of DMAP were successively added thereto, followed by stirring at room temperature overnight. The reaction liquid was ice-cooled, similarly ice-cooled 0.1 mol/L hydrochloric acid was added thereto, and the mixture was extracted with methylene chloride. After drying over anhydrous sodium sulfate, the solvent was removed under reduced pressure to obtain 1.84 g of the following compound (quantitative).

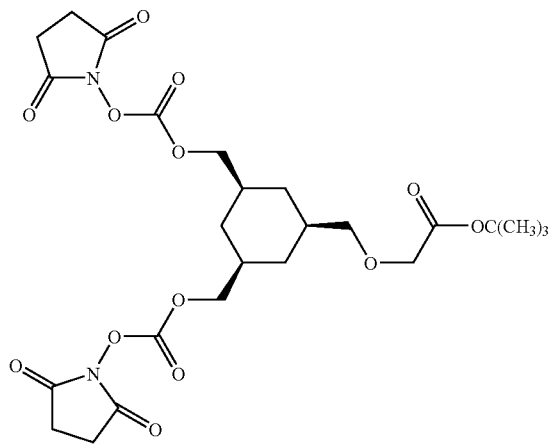

<$^1$H-NMR analysis (CDCl$_3$, 300 MHz)>;
δ (ppm): 0.7-1.9 (m, 9H), 1.47 (s, 9H), 2.82 (s, 8H), 3.37 (d, J=6.0 Hz, 2H), 3.93 (s, 2H), 4.17 (d, J=5.9 Hz, 4H)

<Mass analysis (FAB-MS)>
Found value: (M-tert-butyl+2H)$^+$ 515 Calculated value: C$_{25}$H$_{34}$N$_2$O$_{13}$=570

In 36 ml of methylene chloride, 1.84 g of the above compound was dissolved. Thereto, 36 ml of a methylene chloride solution containing 33 g of mPEG-NH$_2$ (manufactured by Nippon Oil & Fats Co., Ltd.) was added dropwise and then 935 μl of TEA was added, followed by stirring at room temperature for 4 hours. Thereafter, the reaction liquid was added dropwise to diethyl ether, the resulting white precipitate was collected by filtration and dried under reduced pressure. The resulting white solid was dissolved in 173 ml of a mixed solution of trifluoroacetic acid/methylene chloride/water (500/500/1), followed by stirring at room temperature for 4 hours. The reaction liquid was neutralized with an aqueous saturated sodium hydrogen carbonate solution and extracted with chloroform. After drying over anhydrous sodium sulfate, the solvent was removed under reduced pressure to obtain 33 g of a white solid. The solid was purified using 1000 ml of DEAE-Sepharose F.F. column (Amersham-Pharmacia Biotech) in a similar manner to Example 3 to obtain 13 g of the objective product.

<$^1$H-NMR analysis (CDCl$_3$, 300 MHz)>
δ (ppm): 0.6-2.0 (m, 9H), 1.75 (m, 6H), 3.28 (m, 4H), 3.38 (s, 6H), 3.62 (s, 8 nH), 4.02 (s, 2H), 5.28 (t, J=4.8 Hz, 2H)

<Gel Filtration HPLC Analysis>
Using TSK gel G-2000SW$_{XL}$ column, the product was analyzed under conditions similar to Example 1.

Retention time: 11.4 minutes

EXAMPLE 38

Production of Recombinant Human Interferon-β Modified With 5 kDa Double-Chain Branched Polyethylene Glycol Abbreviation: 5CHTM(2UA)-rhIFN-β

In 10.0 ml of methylene chloride, 1 g (0.1 mmol) of the compound of Example 37 was dissolved and 34.5 mg (0.3 mmol) of NHS and 62 mg (0.3 mmol) of DCC were added thereto, followed by stirring at 0° C. for 1 hour and then at room temperature for 2 hours. The reaction liquid was added dropwise to diethyl ether. The resulting white precipitate was dried under reduced pressure to obtain 650 mg of the NHS ester of the compound of Example 37 (yield: 65%).

Then, 147.3 mg (25 mol per mol of the protein) of the above NHS ester was added to 10 ml (1.18 mg/ml) of the rhIFN-β solution obtained in Reference Example 6 which was prepared with a 20 mmol/L phosphate buffer (pH 7.8) containing ethylene glycol and sodium chloride, and the mixture was allowed to react at 4° C. for overnight. Then, 10 ml of the reaction liquid was subjected to buffer exchange into a 20 mmol/L phosphate buffer (pH 6) containing ethylene glycol using Sephadex G-25 column (Amersham-Pharmacia Biotech) to recover 12 ml. The product was purified using 10 ml of CM-Sepharose F.F. column (Amersham-Pharmacia Biotech) to obtain 1.1 ml of a solution containing 2.3 mg/ml of the objective product (yield: 21.4%).

<Electrophoresis>
SDS-PAGE was carried out in a similar manner to Example 11 to confirm the bands of 1 to 4 molecules-linked substances.

<Gel Filtration HPLC Analysis>
Using TSK gel G-4000SW$_{XL}$ column, the product was analyzed under conditions similar to Example 11.

Retention time:
43.0 minutes (1 molecule-linked substance)
40.2 minutes (2 molecules-linked substance)

EXAMPLE 39

Production of Anti-GD3 Chimera Antibody Modified With 5 kDa Double-Chain Branched Polyethylene Glycol Abbreviation: 5CHTM(2EA2)-KM-871

To 0.5 ml of a KM-871 solution (prepared according to Japanese Published Unexamined Patent Application No. 304989/93) adjusted to 2.6 mg/ml with 20 mmol/L phosphate buffer (pH 7.5), 1.0 mg (10 mol per mol of the protein) of the NHS ester of the compound 5CHTM(2EA2) obtained in Example 36 was added, and the mixture was allowed to react at 4° C. for overnight. Then, 0.5 ml of the reaction liquid was purified using 1.2 ml of CM-Sepharose F.F. column (Amersham-Pharmacia Biotech) to obtain 0.38 ml of a solution containing 0.59 mg/ml of the objective product (yield: 17.1%).

<Electrophoresis>
SDS-PAGE was carried out in a similar manner to Example 11 to confirm the bands of 1 to 2 molecules-linked substances.

REFERENCE EXAMPLE 1

Synthesis of 10 kDa Single-Chain Polyethylene Glycol Derivative

Abbreviation: 10SCM

Structure: $CH_3(OCH_2CH_2)_nOCH_2COOH$

The compound was produced by the following process in accordance with the method of S. Zalipsky and G. Barany [*Journal of Bioactive and Compatible Polymers*, 5: 227 (1990)].

In 50 ml of dry toluene, 10 g of dried monomethoxy polyethylene glycol (average molecular weight: 10,000, SUNBRIGHT VFM-3010M, manufactured by Nippon Oil & Fats co., Ltd.) was dissolved, 1.12 g of potassium tert-butoxide was added thereto, the mixture was evaporated to remove 30 ml of initial fraction. In an argon stream, after cooling to 50° C., 1.1 ml of ethyl a-bromoacetate was added thereto, followed by stirring for overnight. The reaction mixture was added to 500 ml of diethyl ether and the resulting precipitate was collected by filtration and dried under reduced pressure. Subsequently, 9.2 g of the resulting dried powder was dissolved in 150 ml of an aqueous solution of 1 mol/L sodium hydroxide, followed by stirring at room temperature for 1 hour. Then, 160 ml of 1 mol/L hydrochloric acid was added and the mixture was extracted with 500 ml of chloroform. The chloroform layer was dried over anhydrous sodium sulfate. After concentration under reduced pressure to 10 ml, the residue was added dropwise into 300 ml of diethyl ether and the resulting precipitate was dried under reduced pressure to obtain 7.5 g of a white powder (yield: 75%).

<$^1$H-NMR analysis ($CDCl_3$, 300 MHz)>
δ (ppm): 3.64 (s, 4 nH), 3.38 (s, 3H), 4.15 (s, 2H)

REFERENCE EXAMPLE 2

Production of Recombinant Human Interferon-β Modified With 10 kDa Single-Chain Polyethylene Glycol Abbreviation: 10SCM-rhIFN-β

In methylene chloride, 1.0 g (0.1 mmol) of the thoroughly dried compound of Reference Example 1 was dissolved and 21.8 mg (0.19 mmol) of NHS and 39.0 mg (0.19 mmol) of DCC were added thereto in an argon stream, followed by stirring under ice cooling for 30 minutes and then at room temperature for 2 hours. An insoluble matter was filtered and the filtrate was added dropwise to diethyl ether to form a precipitate. The precipitate was dried under reduced pressure to obtain 506.8 mg of an NHS ester (yield: 50.7%).

Subsequently, 16.2 mg of the above NHS ester was added to 3.0 ml (0.81 mg/ml) of the rhIFN-β solution obtained in Reference Example 6 which was prepared with a 20 mmol/L phosphate buffer (pH 7.8) containing ethylene glycol and sodium chloride, and the mixture was allowed to react at 4° C. for overnight. Then, the reaction liquid was desalted using Sephadex-G25 gel filtration column (NAP-10, manufactured by Amersham-Pharmacia Biotech). A fraction (4.5 ml) obtained by gel filtration was applied into 2.0 ml of CM Sepharose F.F. column (Amersham-Pharmacia Biotech) and the column was eluted with the buffer containing 0.05 to 1.0 mol/L sodium chloride. Thus, 4.0 ml of a fraction containing 0.22 mg/ml of the objective product was recovered (yield: 36.2%).

<Electrophoresis>
The product was analyzed in a similar manner to Example 11 to confirm the modified substances wherein 1 to 3 molecules of polyethylene glycol were linked.

<Gel Filtration HPLC Analysis>
Using two TSK gel G-4000SW$_{XL}$ columns, the product was analyzed under conditions similar to Example 11.

Retention time:
44.2 minutes (1 molecule-linked substance)
41.0 minutes (2 molecules-linked substance)

REFERENCE EXAMPLE 3

Production of Recombinant Human Granulocyte-Colony Stimulating Factor Derivative Modified With 10 kDa Single-Chain Polyethylene Glycol Abbreviation: 10SCM-rhG-CSF Derivative To 2.5 ml of rhG-CSF derivative obtained in Reference Example 5 which was adjusted to 4.0 mg/ml with 50 mmol/L phosphate buffer (pH 7.5), 21.3 mg (4 mol per mol of the protein) of the NHS ester of 10SCM obtained in a similar manner to Reference Example 2 was added, and the mixture was allowed to react at 4° C. for overnight. The reaction liquid was applied into Sephadex G-25 column (NAP-10, manufactured by Amersham-Pharmacia Biotech) equilibrated with a 20 mmol/L acetate buffer (pH 4.5) to recover 4.0 ml. The recovered solution was applied into 10.0 ml of SP-Sepharose F.F. column (manufactured by Amersham-Pharmacia Biotech) and the column was washed with the buffer containing 50 to 300 mmol/L sodium chloride. Objective fractions were combined to thereby recover 22.5 ml, a 11 ml portion thereof was concentrated to obtain 860 μl of a solution containing 2.0 mg/ml of the objective product (yield: 34.4%).

<Electrophoresis>
SDS-PAGE was carried out in a similar manner to Example 11 to confirm the bands of 1 to 3 molecules-linked substances.

<Gel Filtration HPLC Analysis>
Using TSK gel G-4000SW$_{XL}$ column, the product was analyzed under conditions similar to Example 11.

Retention time:
42.0 minutes (1 molecule-linked substance)
39.5 minutes (2 molecules-linked substance)

REFERENCE EXAMPLE 4

Production of Bovine Cu/Zn Superoxide Dismutase Modified With 10 kDa Single-Chain Polyethylene Glycol Abbreviation: 10SCM-bSOD To 1.0 ml of the bovine Cu/Zn superoxide dismutase solution (2.0 mg/ml, 50 mmol/L borate buffer (pH 9.0), manufactured by Wako Pure Chemical Industries, Ltd.), 18.8 mg (15 mol per mol of the protein) of the NHS ester of 10SCM obtained in a similar manner to Reference Example 2 was added, and the mixture was allowed to react at 4° C. for overnight. Then, the reaction liquid was purified using 2.0 ml of SP-Sepharose F.F. column (Amersham-Pharmacia Biotech). The column was eluted with the buffer containing 0.1 to 1.0 mol/L sodium chloride and an objective fraction which was free of unmodified SOD was concentrated to obtain a solution (120 µl) of 5.9 mg/ml (yield: 35.4%). Furthermore, an aqueous CuSO$_4$ solution and an aqueous ZnSO$_4$ solution were added to give 10 mmol/L respectively to thereby restore the activity.

<Electrophoresis>

SDS-PAGE was carried out in a similar manner to Example 11 to confirm the bands of 1 to 3 molecules-linked substances.

REFERENCE EXAMPLE 5

Preparation of Recombinant Human Granulocyte-Colony Stimulating Factor (rhG-CSF) Derivative An rhG-CSF derivative wherein 1st threonine was replaced with alanine, 3rd leucine was replaced with threonine, 4th glycine was replaced with tyrosine, 5th proline was replaced with arginine and 17th cysteine was replaced with serine in hG-CSF having the amino acid sequence shown by SEQ ID NO:3 was obtained by the method described in Japanese Published Examined Patent Application No. 96558/95.

*Escherichia coli* W3110strA having a plasmid pCfBD28 containing DNA encoding the above rhG-CSF derivative (*Escherichia coli* ECfBD28 FERM BP-1479) was cultured in LG medium (10 g of bactotrypton, 5 g of yeast extract, 5 g of sodium chloride, and 1 g of glucose was dissolved in 1 L of water and the pH was adjusted to 7.0 with NaOH) at 37° C. for 18 hours. The culture liquid (5 ml) was coated on 100 ml of MCG medium (0.6% Na$_2$HPO$_4$, 0.3% KH$_2$PO$_4$, 0.5% sodium chloride, 0.5% Casamino acid, 1 mmol/L MgSO$_4$, 14 µg/ml vitamin B, pH 7.2) containing 25 µg/ml tryptophan and 50 µg/ml ampicillin. After culturing for 4 to 8 hours at 30° C., 10 µg/ml of an derivative of tryptophan, 3β-indolacrylic acid (hereinafter abbreviated as IAA) was added, followed by further culturing for 2 to 12 hours. The culture liquid was centrifuged at 8,000 rpm for 10 minutes to collect the fungi and they were washed with a 30 mmol/L aqueous sodium chloride solution and a 30 mmol/L tris-hydrochloride buffer (pH 7.5). The washed fungi were suspended into 30 ml of the above buffer and disrupted with ultrasonication at 0° C. for 10 minutes (BRANSON SONIC POWER COMPANY, SONIFIER CELL DISRUPTOR 200, OUTPUT CONTROL 2). The ultrasonic disrupted matter was centrifuged at 9,000 rpm for 30 minutes to obtain a fungus residue.

From the fungus residue, an rhG-CSF derivative was extracted, purified, solubilized and regenerated in accordance with the method of Marsto et al. [*BIO/TECHNOLOGY*, 2: 800 (1984)].

REFERENCE EXAMPLE 6

Production of Recombinant Human Interferon-β (Unmodified rhIFN-β)

rhIFn-β was produced according to the method of Mizukami et al. [*Biotechnology Letter*, 8: 605 (1986)] and the method of Kuga et al. [*Chemistry Today*, extra number 12: Gene Engineering in Medical Science, p. 135 (1986), Tokyo Kagaku Dojin].

*Escherichia coli* K-12 comprising a plasmid pMG-1 containing DNA encoding rhIFn-β was seed-cultured in LGTrpAp medium (10 g/l bactotrypton, 5 g/l yeast extract, 5 g/l sodium chloride, 1 g/l glucose, 50 mg/l L-tryptophan and 50 µg/l ampicillin). For the production of rhIFn-β, cell culture was carried out at 20° C. for several days in a 2-liter jar fermenter using MCGAp medium (0.5% casamino acid and 50 µg/ml ampicillin were added to M9 medium) while maintaining the glucose concentration of 1% and the pH of 6.5. Also, the culture liquid was shaken at 750 rpm and aerated at 1 L per minute. From the culture liquid, an extract liquid was prepared according to the freezing and thawing method [DNA, 2: 265 (1983)]. From the fungus residue, rhIFN-β was obtained according to the method described in Japanese Published Unexamined Patent Application No. 69799/86.

REFERENCE EXAMPLE 7

Production of Recombinant Human Interferon-γ rhIFn-γ was produced according to the method of Ito et al. [*Medical Molecular Biology*, p. 355 (1987), Nankodo] and the method of Kuga et al. [*Chemistry Today*, extra number 12: Gene Engineering in Medical Science, p. 135 (1986), Tokyo Kagaku Dojin] in accordance with the production of the above rhIFN-β.

*Escherichia coli* pGKA2 comprising a plasmid pKYP10 containing DNA encoding rhIFn-γ was seed-cultured in LGTrpAp medium (10 g/l bactotrypton, 5 g/l yeast extract, 5 g/l sodium chloride, 1 g/l glucose, 50 mg/l L-tryptophan and 50 µg/l ampicillin). For the production of rhIFn-γ, cell culture was carried out at 37° C. for 1 to 2 days in a 2-liter jar fermenter using MCGAp medium (0.5% Casamino acid and 50 µg/ml ampicillin were added to M9 medium) while maintaining the glucose concentration of 1% and the pH of 6.5. Also, the culture liquid was shaken at 750 rpm and aerated at 1 L per minute. The culture liquid was centrifuged at 8,000 rpm for 10 minutes to collect the fungi and they were washed with a 30 mmol/L aqueous sodium chloride solution and a 30 mmol/L tris-hydrochloride buffer (pH 7.5). The washed fungi were suspended into 30 ml of the above buffer and disrupted with ultrasonication at 0° C. for 10 minutes (BRANSON SONIC POWER COMPANY, SONIFIER CELL DISRUPTOR 200, OUTPUT CONTROL 2). The ultrasonic disrupted matter was centrifuged at 9,000 rpm for 30 minutes to obtain a fungus residue.

After the dissolution of rhIFN-γ by adding a potent protein-denaturing agent such as urea, guanidine hydrochloride or the like to the fungus residue, rhIFN-γ was extracted, purified, solubilized and regenerated in accordance with the method of Marsto et al. [*BIO/TECHNOLOGY*, 2: 800 (1984)].

REFERENCE EXAMPLE 8

Preparation of Conventional Double-Chain Branched PEG Reagent

Abbreviation: 5PEG$_2$GABA

Structure:

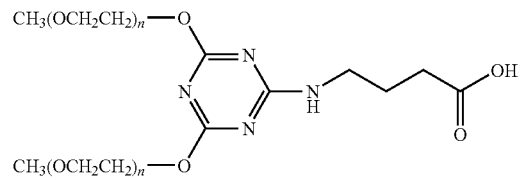

In a flask, 2.0 g of monomethoxy polyethylene glycol having an average molecular weight of 5,000 (manufactured by Nippon Oil & Fats Co., Ltd.), 444 mg of zinc oxide and 10 ml of dry benzene were placed, followed by heating to 90 to 95° C. in an oil bath to thereby remove 4 ml of initial fraction. After further refluxing for 5 hours and cooling to room temperature, 36 mg of cyanuric chloride and 1 g of molecular sieves 4A were added thereto, followed by dehydration under refluxing for 3 days. The reaction liquid was cooled and then centrifuged at 3,000 rpm. The supernatant was added dropwise to diethyl ether and the resulting precipitate was collected and dried under reduced pressure. The resulting white powder (1 g) was dissolved in 10 ml of a 0.1 mol/L borate buffer (pH 10.0) containing 30 mg of aminobutyric acid, and the mixture was allowed to react at 4° C. for 3 days. The pH was adjusted to 1 to 2 by adding 1 mol/L hydrochloric acid and the mixture was extracted with chloroform. The chloroform layer was concentrated and added dropwise to diethyl ether to collect 930 mg of the resulting precipitate. The precipitate was dissolved in 930 ml of water and purified on 80 ml of DEAE Sepharose F.F. column (Amersham-Pharmacia Biotech). An objective fraction was collected and, after adjusting the pH to 1 to 2 with 1 mol/L hydrochloric acid, extracted with an appropriate amount of chloroform, followed by concentration under reduced pressure. The concentrate was added to diethyl ether and the resulting precipitate was dried under reduced pressure to obtain 618 mg of the objective product (yield: 62%).

<Gel Filtration HPLC Analysis>

Using TSK gel G-2000SW$_{XL}$ column, the product was analyzed in a similar manner to Example 1.

Retention time: 12.4 minutes

<LH-NMR analysis (300 MHz)>

δ (ppm): 2.38 (t, 2H, J=6.92), 1.95 (m, 2H), 5.66 (brt, J=6.33 Hz, 1H), 4.43 (brm, 2H), 3.38 (s, 6H), 3.64 (brs, 8 nH)

REFERENCE EXAMPLE 9

Preparation of Recombinant Human Granulocyte-Colony Stimulating Factor rhG-CSF having the amino acid sequence shown by SEQ ID NO:3 was prepared in accordance with the method described in Reference Example 5.

INDUSTRIAL APPLICABILITY

The polyalkylene glycol of the present invention having a novel branched structure is useful as a chemically modifying agent for physiologically active polypeptides. Furthermore, a physiologically active peptide modified with the polyalkylene glycol not only has a biological activity similar to the unmodified peptide but also exhibits the physiological activity for a long period of time when it is administered in the living body, so that it is useful as an agent for improving or treating the symptoms relating to the physiological activity.

The invention claimed is:

1. A branched polyalkylene glycol represented by formula (I):

wherein L represents a nonplanar cyclic group represented by formula (II) or (III):

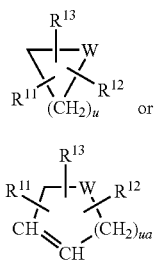

of which 3 to 5 hydrogen atoms are removed from the moiety represented by following formula (II-a) or (III-a) to form binding group(s),

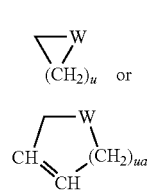

wherein u represents an integer of 1 to 10 and ua represents an integer of 0 to 8; $R^{11}$, $R^{12}$ and $R^{13}$ independently represent a hydrogen atom, a hydroxyl group, substituted or unsubstituted lower alkyl, lower alkoxy, amino, carboxy, cyano or formyl; and W represents $CH_2$;

M represents $OCH_2CH_2$, $OCH_2CH_2CH_2$, $OCH(CH_3)CH_2$, $(OCH_2CH_2)_r$—$(OCH_2CH_2CH_2)_s$ in which r represents an integer of 1 to 100,000, and s represents an integer of 1 to 100,000, or $(OCH_2CH_2)_{ra}$—$(OCH(CH_3)CH_2)_{sa}$ in which ra and sa have the same meanings as r and s, respectively;

n represents an integer of 10 to 100,000;

q represents an integer of 1 to 3;

$R^1$ represents a hydrogen atom, lower alkyl or lower alkanoyl;

$R^2$ represents a hydroxyl group, carboxy, formyl, amino, vinylsulfonyl, mercapto, cyano, carbamoyl, halogenated carbonyl, halogenated lower alkyl, isocyanato, isothiocyanato, oxiranyl, lower alkanoyloxy, maleimido, succinimidooxycarbonyl, substituted or unsubstituted aryloxycarbonyl, benzotriazolyloxycarbonyl, phthalimidooxycarbonyl, imidazolylcarbonyl, substituted or unsubstituted lower alkoxycarbonyloxy, substituted or unsubstituted aryloxycarbonyloxy, tresyl, lower alkanoyloxycarbonyl, substituted or unsubstituted aroyloxycarbonyl, substituted or unsubstituted aryldisulfido or azido, $X^1$ represents a bond; O; S; alkylene; $O(CH_2)_{ta}$ in which ta represents an integer of 1 to 8; $(CH_2)_{tb}O$ in which tb has the same meaning as ta; $NR^3$ in which $R^3$ represents a hydrogen atom or lower alkyl; $R^4$—NH—C(=O)—$R^5$ wherein $R^4$ represents a bond, alkylene or $O(CH_2)_{tc}$ in which tc has the same meaning as ta, and $R^5$ represents a bond, alkylene or $OR^{5a}$ in which $R^{5a}$ represents a bond or alkylene; $R^6$—C(=O)—NH—$R^7$ wherein $R^6$ represents a bond, alkylene or $R^{6a}$O in which $R^{6a}$ has the same meaning as the above $R^{5a}$, and $R^7$ represents a bond, alkylene or $(CH_2)_{td}$O in which td has the same meaning as ta; $R^8$—C(=O)—O in which $R^8$ has the same meaning as $R^{5a}$; or O—C(=O)—$R^9$ in which $R^9$ has the same meaning as $R^{5a}$;

$X^2$ represents a bond, O or $(CH_2)_{te}$O in which te has the same meaning as ta;

$X^3$ represents a bond or alkylene; and

2 $R^1$-$M_n$-$X^1$'s and 1 to 3 $X^2$—$X^3$—$R^2$'s are independently the same or different.

2. The branched polyalkylene glycol according to claim 1, wherein u is 4.

3. The branched polyalkylene glycol according to claim 2, wherein q is 1.

4. The branched polyalkylene glycol according to claim 1, wherein the molecular weight is 500 to 1,000,000.

5. A compound, comprising a branched polyalkylene glycol represented by formula (I):

wherein L represents a nonplanar cyclic group represented by formula (II) or (III):

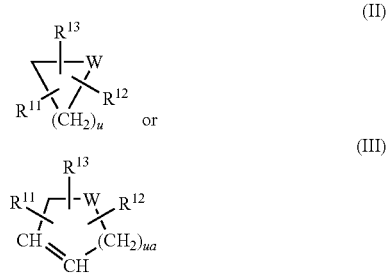

of which 3 to 5 hydrogen atoms are removed from the moiety represented by following formula (II-a) or (III-a) to form binding group(s),

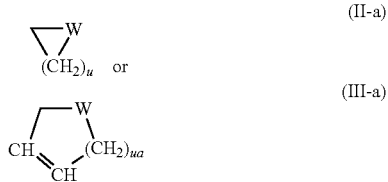

wherein u represents an integer of 1 to 10 and ua represents an integer of 0 to 8; $R^{11}$, $R^{12}$ and $R^{13}$ independently represent a hydrogen atom, a hydroxyl group, substituted or unsubstituted lower alkyl, lower alkoxy, amino, carboxy, cyano or formyl; and W represents $CH_2$;

M represents $OCH_2CH_2$, $OCH_2CH_2CH_2$, $OCH(CH_3)CH_2$, $(OCH_2CH_2)_r$—$(OCH_2CH_2CH_2)_s$ in which r represents an integer of 1 to 100,000, and s represents an integer of 1 to 100,000, or $(OCH_2CH_2)_{ra}$—$(OCH(CH_3)CH_2)_{sa}$ in which ra and sa have the same meanings as r and s, respectively;

n represents an integer of 10 to 100,000;

q represents an integer of 1 to 3;

$R^1$ represents a hydrogen atom, lower alkyl or lower alkanoyl;

$R^2$ represents a hydroxyl group, carboxy, formyl, amino, vinylsulfonyl, mercapto, cyano, carbamoyl, halogenated carbonyl, halogenated lower alkyl, isocyanato, isothiocyanato, oxiranyl, lower alkanoyloxy, maleimido, succinimidooxycarbonyl, substituted or unsubstituted aryloxycarbonyl, benzotriazolyloxycarbonyl, phthalimidooxycarbonyl, imidazolylcarbonyl, substituted or unsubstituted lower alkoxycarbonyloxy, substituted or unsubstituted aryloxycarbonyloxy, tresyl, lower alkanoyloxycarbonyl, substituted or unsubstituted aroyloxycarbonyl, substituted or unsubstituted aryldisulfido or azido, $X^1$ represents a bond; O; S; alkylene; $O(CH_2)_{ta}$ in which ta represents an integer of 1 to 8; $(CH_2)_{tb}O$ in which tb has the same meaning as ta; $NR^3$ in which $R^3$ represents a hydrogen atom or lower alkyl; $R^4$—NH—C(=O)—$R^5$ wherein $R^4$ represents a bond, alkylene or $O(CH_2)_{tc}$ in which tc has the same meaning as ta, and $R^5$ represents a bond, alkylene or $OR^{5a}$ in which $R^{5a}$ represents a bond or alkylene; $R^6$—C(=O)—NH—$R^7$ wherein $R^6$ represents a bond, alkylene or $R^{6a}O$ in which $R^{6a}$ has the same meaning as the above $R^{5a}$, and $R^7$ represents a bond, alkylene or $(CH_2)_{td}O$ in which td has the same meaning as ta; $R^8$—C(=O)—O in which $R^8$ has the same meaning as $R^{5a}$; or O—C(=O)—$R^9$ in which $R^9$ has the same meaning as $R^{5a}$;

$X^2$ represents a bond, O or $(CH_2)_{te}O$ in which te has the same meaning as ta;

$X^3$ represents a bond or alkylene; and

2 $R^1$-$M_n$-$X^1$'s and 1 to 3 $X^2$—$X^3$—$R^2$'s are independently the same or different, wherein the molecular weight of said branched polyalkylene glycol is 500 to 1,000,000 and said branched polyalkylene glycol is attached directly or through a spacer to a physiologically active polypeptide.

6. The compound according to claim 5, wherein the physiologically active polypeptide is an enzyme, a cytokine or a hormone.

7. A pharmaceutical composition comprising the compound according to claim 5 and a pharmaceutically acceptable excipient.

8. The pharmaceutical composition according to claim 7, wherein the physiologically active polypeptide is an interferon.

9. A method for treating multiple scleroses which comprises administering, to a patient in need thereof, a compound comprising a branched polyalkylene glycol represented by formula (I):

$$(R^1\text{-}M_n\text{-}X^1)_2L(X^2\text{—}X^3\text{—}R^2)_q \quad (I)$$

wherein L represents a nonplanar cyclic group represented by formula (II) or (III):

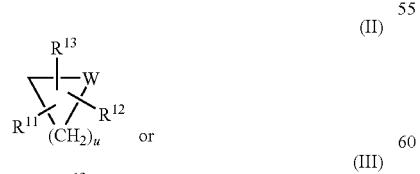

(II)

(III)

of which 3 to 5 hydrogen atoms are removed from the moiety represented by following formula (II-a) or (III-a) to form binding group(s),

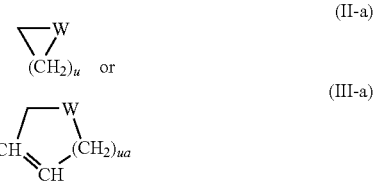

wherein u represents an integer of 1 to 10 and ua represents an integer of 0 to 8; $R^{11}$, $R^{12}$ and $R^{13}$ independently represent a hydrogen atom, a hydroxyl group, substituted or unsubstituted lower alkyl, lower alkoxy, amino, carboxy, cyano or formyl; and W represents $CH_2$;

M represents $OCH_2CH_2$, $OCH_2CH_2CH_2$, $OCH(CH_3)CH_2$, $(OCH_2CH_2)_r$—$(OCH_2CH_2CH_2)_s$ in which r represents an integer of 1 to 100,000, and s represents an integer of 1 to 100,000, or $(OCH_2CH_2)_{ra}$—$(OCH(CH_3)CH_2)_{sa}$ in which ra and sa have the same meanings as r and s, respectively;

n represents an integer of 10 to 100,000;

g represents an integer of 1 to 3;

$R^1$ represents a hydrogen atom, lower alkyl or lower alkanoyl;

$R^2$ represents a hydroxyl group, carboxy, formyl, amino, vinylsulfonyl, mercapto, cyano, carbamoyl, halogenated carbonyl, halogenated lower alkyl, isocyanato, isothiocyanato, oxiranyl, lower alkanoyloxy, maleimido, succinimidooxycarbonyl, substituted or unsubstituted aryloxycarbonyl, benzotriazolyloxycarbonyl, phthalimidooxycarbonyl, imidazolylcarbonyl, substituted or unsubstituted lower alkoxycarbonyloxy, substituted or unsubstituted aryloxycarbonyloxy, tresyl, lower alkanoyloxycarbonyl, substituted or unsubstituted aroyloxycarbonyl, substituted or unsubstituted aryldisulfido or azido, $X^1$ represents a bond; O; S; alkylene; $O(CH_2)_{ta}$ in which ta represents an integer of 1 to 8; $(CH_2)_{tb}O$ in which tb has the same meaning as ta; $NR^3$ in which $R^3$ represents a hydrogen atom or lower alkyl; $R^4$—NH—C(=O)—$R^5$ wherein $R^4$ represents a bond, alkylene or $O(CH_2)_{tc}$ in which tc has the same meaning as ta, and $R^5$ represents a bond, alkylene or $OR^{5a}$ in which $R^{5a}$ represents a bond or alkylene; $R^6$—C(=O)—NH—$R^7$ wherein $R^6$ represents a bond, alkylene or $R^{6a}O$ in which $R^{6a}$ has the same meaning as the above $R^{5a}$, and $R^7$ represents a bond, alkylene or $(CH_2)_{td}O$ in which td has the same meaning as ta; $R^8$—C(=O)—O in which $R^8$ has the same meaning as $R^{5a}$; or O—C(=O)—$R^9$ in which $R^9$ has the same meaning as $R^{5a}$;

$X^2$ represents a bond, O or $(CH_2)_{te}O$ in which te has the same meaning as ta;

$X^3$ represents a bond or alkylene; and

2 $R^1$-$M_n$-$X^1$'s and 1 to 3 $X^2$—$X^3$—$R^2$'s are independently the same or different, wherein the molecular weight of said branched polyalkylene glycol is 500 to 1,000,000 and said branched polyalkylene glycol is attached directly or through a spacer to interferon-β.

10. The branched polyalkylene glycol according to claim 1, wherein the average molecular weight of $M_n$ is 2,000 or more.

11. The branched polyalkylene glycol according to claim 1, wherein the average molecular weight of $M_n$ is 5,000 or more.

12. The branched polyalkylene glycol according to claim 1, wherein the average molecular weight of $M_n$ is 10,000 or more.

13. The branched polyalkylene glycol according to claim 1, wherein the average molecular weight of $M_n$ is 20,000 or more.

14. The branched polyalkylene glycol according to claim 1, wherein the average molecular weight of $M_n$ is 2,000 or more.

15. The branched polyalkylene glycol according to claim 1, wherein the average molecular weight of the moiety of $M_n$ is 5,000 or more.

16. The branched polyalkylene glycol according to claim 1, wherein the average molecular weight of $M_n$ is 10,000 or more.

17. The branched polyalkylene glycol according to claim 1, wherein the average molecular weight of $M_n$ is 20,000 or more.

* * * * *

UNITED STATES PATENT AND TRADEMARK OFFICE
CERTIFICATE OF CORRECTION

| | | |
|---|---|---|
| PATENT NO. | : 7,691,367 B2 | |
| APPLICATION NO. | : 10/168956 | |
| DATED | : April 6, 2010 | |
| INVENTOR(S) | : Motoo Yamasaki et al. | |

It is certified that error appears in the above-identified patent and that said Letters Patent is hereby corrected as shown below:

ON THE TITLE PAGE [30]

FOREIGN APPLICATION PRIORITY DATA, "11/366312" should read --11-366312--.

COLUMN 1

Line 22, "them" should read --it--.

COLUMN 3

Line 6, "glycol" should read --glycols--.

COLUMN 6

Line 27, "formula (1)" should read --formula (I)--.

COLUMN 7

Line 14, "SYNTHSIS," should read --SYNTHESIS,--.

COLUMN 8

Line 18, "SYNTHSIS," should read --SYNTHESIS,--; and
    Line 53, "-20to" should read -- -20 to--.

COLUMN 9

Line 7, "SYNTH-" should read --SYNTHE- --.

Signed and Sealed this

Twenty-ninth Day of June, 2010

David J. Kappos
*Director of the United States Patent and Trademark Office*

COLUMN 10

Line 22, "SYNTHSIS," should read --SYNTHESIS,--; and
Line 57, "can" should read --¶can--.

COLUMN 12

Line 17, "an" should read --a--; and
Line 30, "an" should read --a--.

COLUMN 19

Line 55, "method" should read --methods--.

COLUMN 21

Line 16, "insulin like" should read --insulin-like--;
Line 34, "valuable" should read --variable--;
Line 37, "CH," should read --"CH",--;
Line 38, "C region)" should read --"C region")--;
Line 39, "valuable" should read --variable--; and
Line 40, "an" should read --a--.

COLUMN 22

Line 50, "polypeptides" should read --polypeptide--.

COLUMN 24

Line 17, "subr-" should read --sub- --.

COLUMN 30

Line 10, "rhIFN-αwere" should read --rhIFN-α were--.

COLUMN 33

Line 22, "gel." should read --gel. Table 11 shows one example of the apparent molecular weight obtained by electrophoresis of each chemically modified rhIFN-β.--.

COLUMN 35

Line 6, "SOD" should read --SODs--.

COLUMN 36

Line 4, "glycol" should read --glycols--.

CERTIFICATE OF CORRECTION (continued)
U.S. Pat. No. 7,691,367 B2

COLUMN 38

Line 67, "(thereafter," should read --(hereafter,--.

COLUMN 39

Line 61, "($KH_2PO_4$, $Na_2HPO_4$1.2$H_2O$," should read --($KH_2PO_4$, $Na_2HPO_4$ • 12$H_2O$,--.

COLUMN 40

Line 45, "were died" should read --were killed--.

COLUMN 41

Line 33, "are" should read --is--; and
    Line 35, "means" should read --mean--.

COLUMN 42

Line 21, "weight::" should read --weight:--;
    Line 58, "Abbreviation:" should read --¶Abbreviation:--; and
    Line 67, "weight::" should read --weight:--.

COLUMN 43

Line 34, "weight::" should read --weight:--.

COLUMN 44

Line 66, "weight::" should read --weight:--.

COLUMN 45

Line 62, "<H-NMR" should read --<$^1$H-NMR--.

COLUMN 46

Line 16, "MPEG" should read --mPEG--.

COLUMN 47

Line 19, "weight::" should read --weight:--; and
    Line 49, "weight::" should read --weight:--.

COLUMN 48

Line 27, "weight::" should read --weight:--; and
    Line 52, "δ (ppm):" should read --¶δ (ppm):--.

COLUMN 49

Line 55, "-cys,cys-1,3," should read --cis,cis-1,3,--; and
   Line 64, "$C_{15}H_{28}O_5 288$" should read --$C_{15}H_{28}O_5=288$--.

COLUMN 51

Line 8, "Stain-" should read --¶Stain- --;
   Line 9, "Molecular" should read --¶Molecular--;
   Line 14, "Flow" should read --¶Flow--;
   Line 15, "Separating" should read --¶Separating--; and
   Line 17, "Retention" should read --¶Retention--.

COLUMN 53

Line 51, "5CHTC(2AA)-rhIFNα" should read --5CHTC(2AA-rhIFN-α--.

COLUMN 56

Line 44, "(450 tl)" should read --450 μl)--.

COLUMN 57

Line 7, "compound 4" should read --Compound 4--.

COLUMN 60

Line 63, "Ranched" should read --Branched--.

COLUMN 63

Line 16, "289Calculated" should read --"289 Calculated--.

COLUMN 67

Line 34, "an" should read --a--.

COLUMN 68

Line 37, "rhIFN-γby" should read --rhIFN-γ by--.

COLUMN 70

Line 2, "<LH-NMR analysis (300 MHz)>" should read --<$^1$H-NMR analysis (300 MHz)>--.

COLUMN 73

Line 22, "following" should read --the following--; and
    Line 61, "azido," should read --azido;--.

COLUMN 74

Line 40, "following" should read --the following--.

COLUMN 75

Line 12, "azido," should read --azido;--.

COLUMN 76

Line 2, "following" should read --the following--;
    Line 26, "g represents" should read --q represents--; and
    Line 41, "azido," should read --azido;--.

COLUMN 77

Line 9, "claim 1," should read --claim 2,--.

COLUMN 78

Line 1, "claim 1," should read --claim 2,--;
    Line 4, "claim 1," should read --claim 2,--; and
    Line 7, "claim 1," should read --claim 2,--.